(12) United States Patent
Jasti et al.

(10) Patent No.: US 10,934,290 B2
(45) Date of Patent: Mar. 2, 2021

(54) DONOR-ACCEPTOR NANOHOOP COMPOUNDS AND METHODS OF MAKING AND USING THE SAME

(71) Applicant: University of Oregon, Eugene, OR (US)

(72) Inventors: Ramesh Jasti, Eugene, OR (US); Evan R. Darzi, Eugene, OR (US)

(73) Assignee: University of Oregon, Eugene, OR (US)

( * ) Notice: Subject to any disclaimer, the term of this patent is extended or adjusted under 35 U.S.C. 154(b) by 8 days.

(21) Appl. No.: 15/187,644

(22) Filed: Jun. 20, 2016

(65) Prior Publication Data

US 2016/0372684 A1    Dec. 22, 2016

Related U.S. Application Data

(60) Provisional application No. 62/183,124, filed on Jun. 22, 2015.

(51) Int. Cl.
| | | |
|---|---|---|
| *C07D 471/22* | (2006.01) | |
| *C07D 471/08* | (2006.01) | |
| *C07D 471/18* | (2006.01) | |
| *H01L 51/00* | (2006.01) | |

(52) U.S. Cl.
CPC ......... *C07D 471/22* (2013.01); *C07D 471/08* (2013.01); *C07D 471/18* (2013.01); *H01L 51/005* (2013.01); *H01L 51/0051* (2013.01); *H01L 51/0067* (2013.01); *H01L 51/0071* (2013.01); *H01L 51/0073* (2013.01); *Y02E 10/549* (2013.01)

(58) Field of Classification Search
CPC .................................................. C07D 471/08
See application file for complete search history.

(56) References Cited

U.S. PATENT DOCUMENTS

| | | | |
|---|---|---|---|
| 8,461,403 B2 | 6/2013 | Jasti et al. | |
| 8,895,768 B2 | 11/2014 | Yamago | |
| 9,029,551 B2 | 5/2015 | Itami et al. | |
| 9,090,473 B2 | 7/2015 | Jasti et al. | |
| 9,481,618 B2 | 11/2016 | Itami et al. | |
| 2011/0166390 A1 | 7/2011 | Jasti et al. | |
| 2012/0220790 A1 | 8/2012 | Yamago | |

OTHER PUBLICATIONS

Matsui. Organic Letters, 2012, 14(7), 1888-91 (Year: 2012).*
Kubota. Journal of the American Chemical Society, 2015, 137, 1356-61 (Year: 2015).*
Bandyopadhyay. Physical Chemistry ChemicalPhysics, 2016, 18, 20682-20690 (Year: 2016).*
Jasti. Journal of the American Chemical Society, 2008, 130, 17646-17647 (Year: 2008).*
Darzi, Research Presentation/Slides, Sep. 24, 2014.
Hirst "Synthesis of Nitrogen-Substituted Cycloparaphenylenes," Thesis Defense Presentation, May 13, 2014.
Hirst "Synthesis of Nitrogen-Substituted Cycloparaphenylenes," Dissertation, May 2014.
Ball et al., "Stepping into the Light: Conjugated Macrocycles with Donor-Acceptor Motifs," ACS Cent. Sci., 1, 416-417, Oct. 27, 2015.
Zhang et al., "Giant Cyclo[n]thiophenes with Extended π Conjugation," *Angewandte Chemie Int. Ed.*, 48(36): 6632-6635, Jun. 27, 2009.
Iwamoto et al., "Selective and Random Syntheses of [n]Cycloparaphenylenes (n=8-13) and Size Dependence of Their Electronic Properties," *Journal of the American Chemical Society*, 133(21): 8354-8361, May 4, 2011.
Havinga et al., "A new class of small band gap organic polymer conductors," *Polymer Bulletin*, 29(119): 119-126, Aug. 1992.
Kuwabara et al., "Curved oligophenylenes as donors in shape-persistent donor-acceptor macrocycles with solvatofluorochromic properties," *Angew. Chem. Int. Ed.*, 54(33): 9646-9649, Jul. 3, 2015.
Takase et al., "Donor-acceptor segregated paracyclophanes composed of napthobipyrrole and stacked fluoroarenes," *Organic Letters*, 15(13): 3202-3205, Jun. 21, 2013.

* cited by examiner

*Primary Examiner* — Noble E Jarrell
(74) *Attorney, Agent, or Firm* — Klarquist Sparkman, LLP

(57) ABSTRACT

Disclosed herein are embodiments of nanostructure compounds that exhibit unique shape configurations, such as nanohoops. The compounds disclosed herein exhibit unique chemical and electrochemical properties that can be tuned and modified to facilitate their use in a variety of different applications.

21 Claims, 34 Drawing Sheets

DONOR-ACCEPTOR NANOHOOP COMPOUNDS AND METHODS OF MAKING AND USING THE SAME

CROSS REFERENCE TO RELATED APPLICATION

This application claims the benefit of the earlier filing date of U.S. Provisional Patent Application No. 62/183,124, filed on Jun. 22, 2015, the entirety of which is incorporated by reference herein.

ACKNOWLEDGMENT OF GOVERNMENT SUPPORT

This invention was made with government support under Contract No. CHE-1255219 awarded by the National Science Foundation. The government has certain rights in the invention.

FIELD

The present disclosure concerns donor-acceptor functionalized nanohoop compounds and methods of making and using the same.

BACKGROUND

There is a clear need for alternative energy technologies to address the looming worldwide energy crisis. Organic materials are poised to play a large role in these technologies with emerging research on their ability to harvest (organic photovoltaics OPVs), transport (organic field-effect transistors OFETs), and store energy (batteries and capacitors). Polymeric- and small molecule-based organic electronics have received a dramatic upsurge from the scientific communities in recent years for their potential use as light weight and flexible electronic materials. Organic small molecules are relatively cheap, structurally defined, and can be functionalized to systematically study structure property relationships. With the fundamental phenomena governing charge transport beginning to take shape, a diverse toolbox of organic scaffolds is needed to guide future material research. [n]Cycloparaphenylenes ([n]CPPs) pose a unique architecture of fully conjugated bent benzene rings linked in the pare position to form a nanohoop. This nanohoop architecture imparts several advantageous properties in relation to their linear counterparts. However, there exists a need in the art for nanohoop compounds that include functionality that can be tuned so as to modify the chemical and/or electrochemical characteristics of the nanohoop compounds, thereby facilitating their use in a wide variety photochemical and electrochemical devices and applications.

SUMMARY

Disclosed herein are embodiments of compounds having structures satisfying a formula

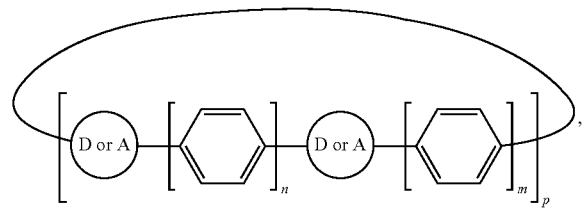

wherein the compound comprises at least one D ring and at least one A ring; wherein each D ring independently can be an aryl ring comprising an electron-donating group or a heteroaryl ring optionally comprising an electron-donating group and each A ring independently can be an aryl ring comprising an electron-accepting group or a heteroaryl ring comprising an electron-accepting group or one or more heteroatoms and/or substituents that are capable of accepting electron density from a core ring to which they are attached. The core ring can be a ring comprising two carbon atoms that each are attached to two different rings of the nanohoop compound. Each of n and m independently can be an integer selected from 0 to 100; and p can be an integer selected from 1 to 100.

In some embodiments, each D ring independently can be selected from phenyl optionally substituted with one or more electron-donating substituents; benzo[1,2-b:4,5-b']dithiophenyl optionally substituted with one or more electron-donating substituents; benzo[1,2-b 4,5-b']difuranyl optionally substituted with one or more electron-donating substituents; 4,4-dimethyl-4H-cyclopenta[2,1-b:3,4-b']dithiophene optionally substituted with one or more electron-donating substituents; or 1,5-dihydropyrrolo[2,3-f]indolyl optionally substituted with one or more electron-donating substituents. In some embodiments, the D ring is phenyl. The one or more electron-donating substituents can be selected from alkoxy, thioether, amide, amine, hydroxyl, thiol, acyloxy, aliphatic (e.g., alkyl, alkenyl, alkynyl), aryl, or combinations thereof.

In some embodiments, each A ring independently can be selected from phenyl substituted with one or more electron-accepting substituents; pyridinyl substituted with an aliphatic or aryl group; benzo[c][1,2,5]thiadiazolyl; benzo[c][1,2,5]oxadiazolyl; or 2H-benzo[d][1,2,3]triazolyl. The electron-accepting substituents can be selected from aldehyde, ketone, ester, carboxylic acid, acyl, acyl halide, cyano, sulfonate, nitro, nitroso, quaternary amine, alkyl halide, or combinations thereof. In some embodiments, the compounds can have any of the other formulas disclosed herein. Representative compounds also are disclosed herein.

In some embodiments, the compound can be a functionalized nanohoop compound that exhibits a LUMO energy level ranging from greater than −2.0 eV to −5 eV. In yet additional embodiments, the compounds can be functionalized nanohoop compounds exhibiting a LUMO energy level ranging from −2.5 eV to −4.0 eV.

In some embodiments, the compound is a functionalized nanohoop compound exhibiting a HOMO energy level ranging from −5.0 eV to −7 eV. In yet additional embodiments, the functionalized nanohoop compound can exhibit a HOMO energy level ranging from −5.2 eV to −6.5 eV.

The compounds can be used in devices, such as organic photovoltaic devices, organic field effect transistors, molecular wires, or organic light emitting diodes. Also disclosed herein are embodiments of making the functionalized nanohoop compounds disclosed herein, comprising exposing a compound having a structure satisfying a Formula V to a reducing agent to produce the compound according to the formulas disclosed herein.

Formula V

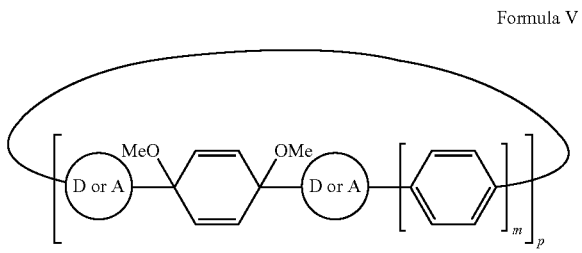

In some embodiments, the reducing agent is an organic salt. In yet additional embodiments, the reducing agent is a metal naphthalenide. In particular disclosed embodiments, the reducing agent is sodium naphthalenide.

The foregoing and other objects, features, and advantages of the present disclosure will become more apparent from the following detailed description, which proceeds with reference to the accompanying figures.

DETAILED DESCRIPTION

I. Explanation of Terms

Figure 1:
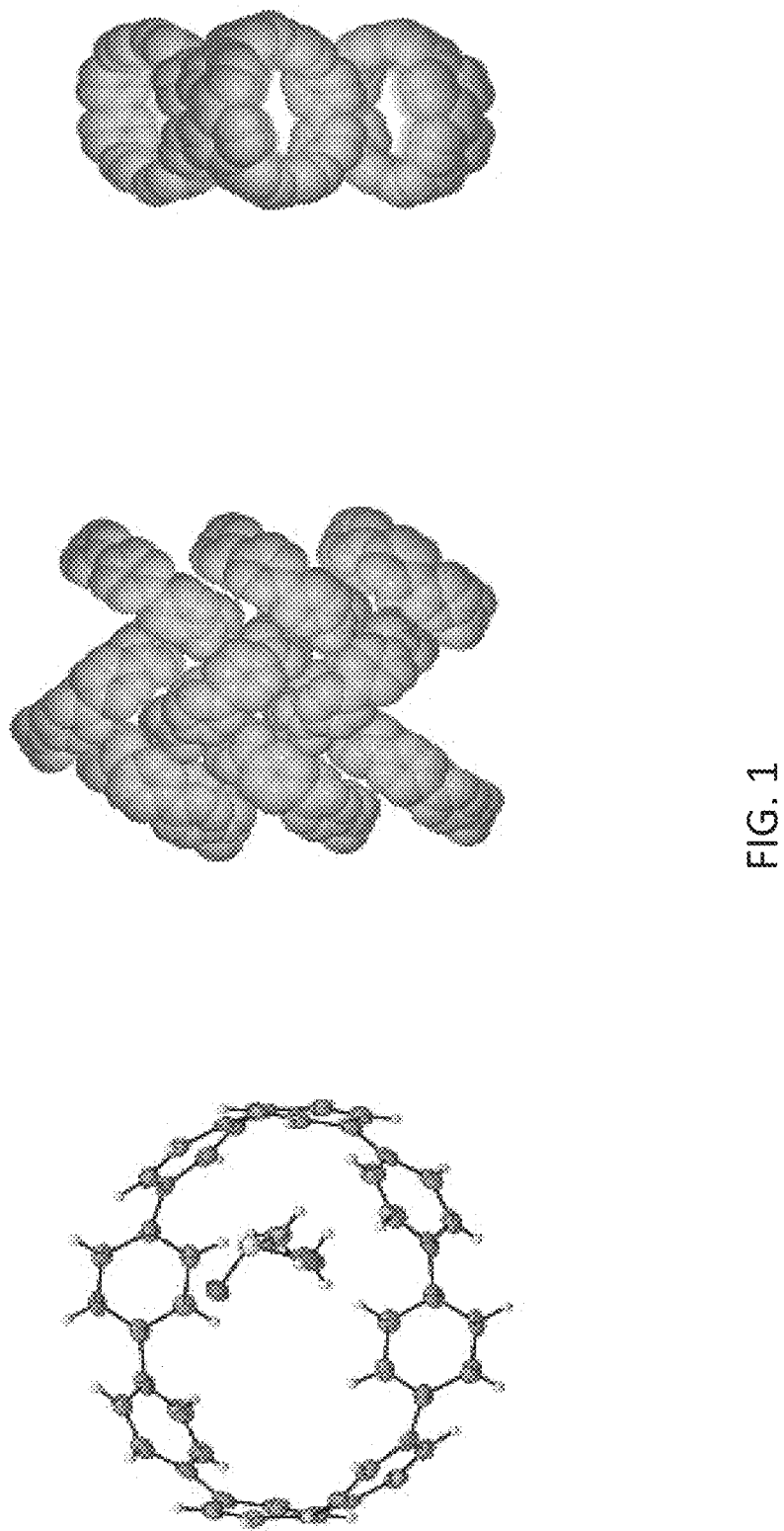
FIG. 1 illustrates different configurations of a non-functionalized nanohoop embodiment illustrating a calculated crystal structure (left); a side-on packing configuration of a plurality of non-functionalized nanohoops (middle); and a top-down packing configuration of a plurality of non-functionalized nanohoops (right).

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a $R^a$ group that, though not part of the defined functional group, indicates how the functional group attaches to the compound to which it is bound.

Acyloxy: $R^aOC(O)R^b$, wherein $R^a$ is the atom of the formulas disclosed herein to which the acyloxy group is attached and $R^b$ is selected from hydrogen, alkyl, alkenyl, alkynyl, aryl, heteroalkyl, heteroalkenyl, heteroalkynyl, or heteroaryl.

Acyl Halide: $R^aC(O)X$, wherein $R^a$ is the atom of the formulas disclosed herein to which the acyl halide group is attached and X is a halogen, such as Br, F, I, or Cl.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkynes (or alkynyl), including cyclic versions thereof, and further including straight- and branched-chain arrangements, and all stereo and position isomers as well.

Aldehyde: $R^aC(O)H$, wherein $R^a$ is the atom of the formulas disclosed herein to which the aldehyde group is attached.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms to 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cylcoalkenyl), cis, or trans (e.g., E or Z).

Alkynyl: An unsaturated monovalent hydrocarbon having at least two carbon atoms to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Alkoxy: —O-alkyl, —O-alkenyl, or —O-alkynyl, with exemplary embodiments including, but not limited to, methoxy, ethoxy, n-propoxy, isopropoxy, n-butoxy, t-butoxy, sec-butoxy, n-pentoxy.

Amide: $R^aC(O)NR^bR^c$ wherein $R^a$ is the atom of the formulas disclosed herein to which the amide is attached, and each of $R^b$ and $R^c$ independently is selected from hydrogen, aliphatic, heteroaliphatic, aryl, heteroaryl, or any combination thereof.

Amine: $R^aNR^bR^c$, wherein $R^a$ is the atom of the formulas disclosed herein to which the amine is attached, and each of $R^b$ and $R^c$ independently is selected from hydrogen, alkyl, alkenyl, alkynyl, aryl, heteroalkyl, heteroalkenyl, heteroalkynyl, heteroaryl, and any combination thereof.

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Carboxyl: $R^aC(O)OR^b$, wherein $R^a$ is the atom of the formulas disclosed herein to which the carboxyl group is attached and wherein $R^b$ is hydrogen.

Electron-Accepting Group (EAG): A functional group capable of accepting electron density from the ring to which it is directly attached, such as by inductive electron withdrawal.

Electron-Accepting Unit: An aryl ring or heteroaryl ring comprising one or more electron-accepting groups or a heteroaryl ring that comprises one or more heteroatoms and/or substituents that are capable of accepting electron density from the core ring to which they are attached. In such embodiments, the core ring comprises two carbon atoms that each are attached to two different rings in the nanohoop.

Electron-Donating Group (EDG): A functional group capable of donating at least a portion of its electron density into the ring to which it is directly attached, such as by resonance.

Electron-Donating Unit: An aryl ring or heteroaryl ring comprising one or more electron-donating groups.

Ester: $R^aC(O)OR^b$, wherein $R^a$ is the atom of the formulas disclosed herein to which the ester group is attached and $R^b$ is selected from alkyl, alkenyl, alkynyl, aryl, heteroalkyl, heteroalkenyl, heteroalkynyl, or heteroaryl.

Functionalized Nanohoop Compound: A nanohoop compound comprising at least one aryl ring comprising at least one electron-accepting group (or an aryl ring that forms an electron-accepting unit) and at least one aryl ring comprising at least one electron-donating group (or an aryl ring that forms an electron-donating unit). In an independent embodiment, a functionalized nanohoop compound does not include a nanohoop consisting of phenyl and pyridinyl rings, wherein the pyridinyl rings lack N-substitution with an aliphatic group. In yet additional independent embodiments, functionalized nanohoop compounds do not include nanohoops consisting of phenyl and pyridinyl rings, wherein the nitrogen atom of each pyridinyl ring is protonated.

Haloaliphatic: An aliphatic group wherein one or more hydrogen atoms, such as one to 10 hydrogen atoms, independently is replaced with a halogen atom, such as fluoro, bromo, chloro, or iodo.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Ketone: $R^aC(O)R^b$, wherein $R^a$ is the atom of the formulas disclosed herein to which the ketone is attached, and $R^b$ is selected from aliphatic, heteroaliphatic, aryl, heteroaryl, and any combination thereof.

Sulfonyl/Sulfonate: A functional group having a structure satisfying a formula $R^aSO_2R^b$, wherein $R^a$ is the atom of the formulas disclosed herein to which the sulfonyl or sulfonate is attached, and $R^b$ is selected from hydrogen, aliphatic, heteroaliphatic, aryl, heteroaryl, and any combination thereof.

Quaternary Amine: $R^aN^+R^bR^cR^d$, wherein $R^a$ is the atom of the formulas disclosed herein to which the quaternary amine is attached, and each of $R^b$, $R^c$, and $R^d$ independently are selected from hydrogen, aliphatic, heteroaliphatic, aryl, heteroaryl, and any combination thereof.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein.

II. Introduction

[n]Cycloparaphenylenes have a narrowing HOMO-LUMO energy gap as the number of benzene units is decreased. This is in stark contrast to conjugated materials, including poly(para-phenylene) (PPP), which have a narrowing HOMO-LUMO energy as the molecule becomes larger. This effect can be very dramatic, as the HOMO-LUMO energy gap for PPP is comparable to [18]CPP and over a full electron volt larger than [5]CPP. This energy level deviation is explained by a strain-induced minimization of the biaryl dihedral angles as the nanohoops become smaller. This effectively increases conjugation around the hoop resulting in the observed HOMO-LUMO energy gaps. Decreasing the dihedral angles is difficult to accomplish outside of the nanohoop architecture and thus offers a powerful new tool for orbital level engineering. An additional advantage includes a unique solid state architecture with long range channels and multiple close π-π close contacts. The curved nature of these nanohoops also affords a significant increase in solubility with solvation possible in both the interior and exterior regions of the hoop.

Significant effort also has been devoted to modifying the electronic properties of carbon materials, better tailoring them to specific applications. Doping of materials with a non-carbon element such as nitrogen, boron, phosphorous, or silicon has been one approach to modify properties. Nitrogen doping in particular has been shown to not only enable tuning of electronics but also introduce novel reactivity into materials; however, conventional methods of obtaining nitrogen-doped compounds utilize top-down syntheses (that is, doping pre-formed/synthesized nanostructures). The top-down synthesis of nitrogen-doped carbon nanotubes (CNTs) has led to significant deviations in chemical and electrochemical behavior and therefore cannot be easily controlled. Top-down nitrogen doping can lead to a number of possible structures, thus making direct structure property relationships difficult to determine and therefore preventing facile manipulation of the electronic properties of such compounds. Bottom-up approaches to obtain nanostructures can prove difficult to control in terms of scale-up and cost-efficiency. The compounds disclosed herein exhibit chemical and electrochemical properties that are superior to those obtained from conventional top-down and/or conventional bottom-up synthetic methods.

III. Functionalized Nanohoop Compounds

Disclosed herein are embodiments of compounds that adopt unique conjugated nanostructures, such as hoop-shaped structures. The compounds disclosed herein exhibit unique electronic characteristics and also exhibit enhanced solubility over conventional linear polymers. The unique hoop-like structures of the disclosed compounds also provide a shape-persistent pore that can be utilized for sensing and/or doping applications. In particular disclosed embodiments, the compounds include para-linked units of aryl rings that exhibit singular aryl ring planes that are perpendicular to the radius of the hoop and therefore the carbon atoms do not all sit in one plane of the aryl ring.

In some embodiments, the compounds can have structures satisfying Formula IA and/or IB, illustrated below.

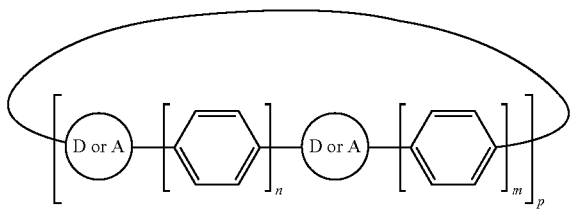

Formula IA

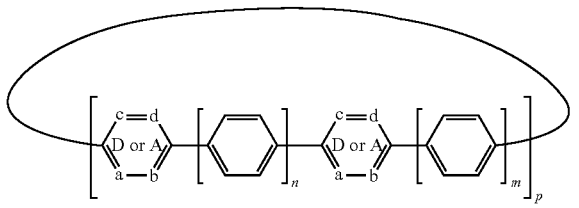

Formula IB

With reference to Formula IA, the "hoop-shaped" nature of the compounds is represented by the solid curved line, which in turn represents a bond formed between a carbon atom of an "A" ring or "D" ring and a pare-positioned carbon atom of another ring to form the hoop structure. Also with reference to Formula IA, each "D" ring independently represents an aryl ring comprising an electron-donating group or a heteroaryl ring optionally comprising an electron-donating group and each "A" ring independently represents an aryl ring comprising an electron-accepting group or a heteroaryl ring comprising an electron-accepting group or one or more heteroatoms and/or substituents that are capable of accepting electron density from a core ring to which they are attached, wherein the core ring is a ring comprising two carbon atoms that each are attached to two different rings of the compound. Each of n and m independently can be integers selected from 0 to 100; p can be an integer selected from 1 to 100; each of a, b, c, and d independently can be selected from carbon or nitrogen. In particular disclosed embodiments, compounds satisfying Formula IA and IB comprise at least one A ring and at least one D ring.

Representative examples of "D" rings include, but are not limited to, phenyl optionally substituted with one or more electron-donating substituents described herein, or D rings can include a ring system having a structure satisfying a formula:

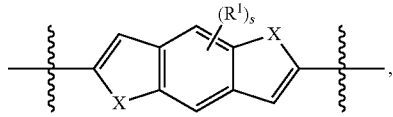

wherein X is selected from O, S, and $NR^b$ (wherein $R^b$ is as defined herein), $R^1$ is selected from an electron-donating group disclosed herein, and s is 0, 1, or 2.

In some embodiments, each D ring independently can be selected from phenyl, benzo[1,2-b:4,5-b']dithiophenyl optionally substituted with one or more electron-donating substituents described herein; benzo[1,2-b:4,5-b']difuranyl optionally substituted with one or more electron-donating substituents described herein; 4,4-dimethyl-4H-cyclopenta[2,1-b:3,4-b']dithiophene optionally substituted with one or more electron-donating substituents described herein; or 1,5-dihydropyrrolo[2,3-f]indolyl optionally substituted with one or more electron-donating substituents described herein.

Representative examples of "A" rings include, but are not limited to, phenyl substituted with one or more electron-accepting substituents described herein; pyridinyl substituted with an aliphatic or aryl group; or a ring system having a structure satisfying a formula:

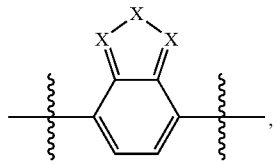

wherein each X independently is selected from O, S, N, or $NR^b$ wherein $R^b$ is as defined herein.

Exemplary species of A rings include, but are not limited to, benzo[c][1,2,5]thiadiazolyl; benzo[c][1,2,5]oxadiazolyl; and 2H-benzo[d][1,2,3]triazolyl. In an independent embodiment, if the A ring is a pyridinyl ring substituted with an aliphatic group and the D ring is a phenyl ring, the aliphatic group is not, or is other than, methyl, when the nanohoop consists of eight total rings.

In some embodiments, and with reference to Formula IB, at least one of a, b, c, and d is a nitrogen atom when the ring containing these variables is an "A" ring. In some embodiments, and with reference to Formula IB each of a, b, c, and d is a carbon atom when the ring containing these variables is a "B" ring.

In some embodiments, each of n and m independently can be selected from 1 to 50, such as 1 to 25, or 1 to 10, or 1 to 5; and p can be selected from 1 to 50, such as 1 to 25, or 1 to 10, or 1 to 5. In particular disclosed embodiments, each of n and m independently can be 0, 1, 2, 3, 4, or 5; and p can be 1, 2, 3, 4, or 5.

In particular disclosed embodiments, the functionalized nanohoop compounds can have a structure satisfying any one or more of Formulas IC-IF illustrated below.

Formula IC

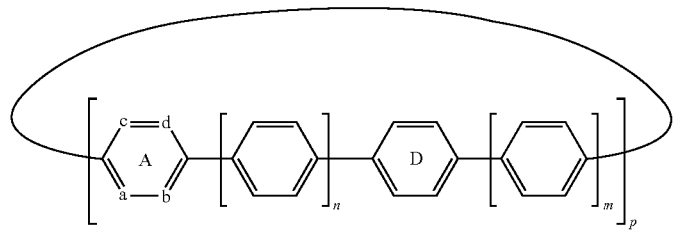

Formula ID

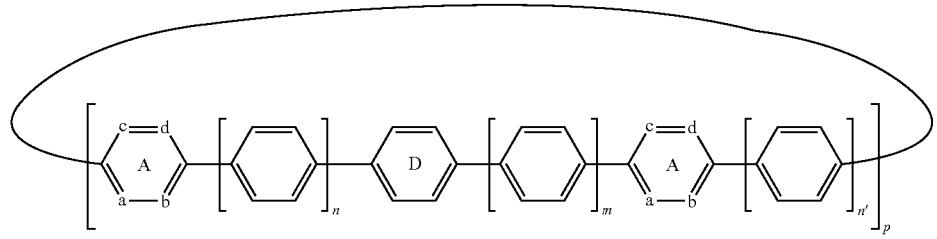

Formula IE

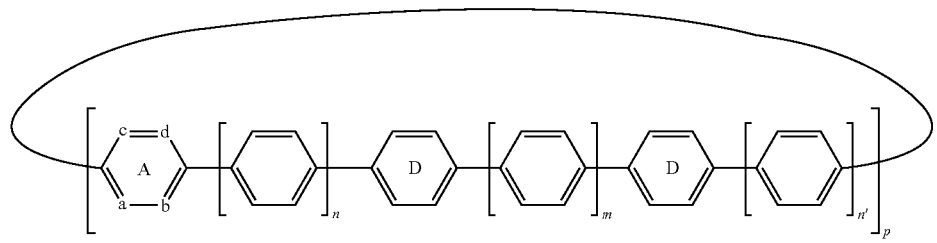

Formula IF

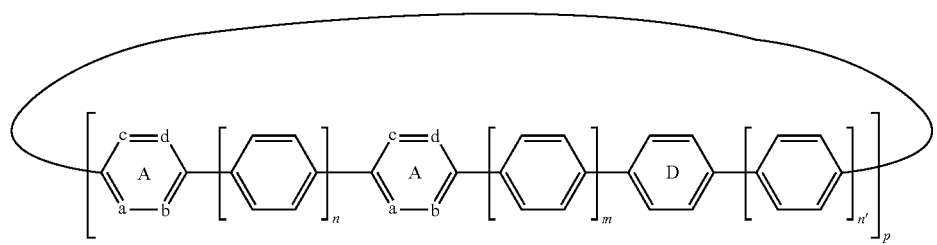

With reference to each of Formulas IC-IF, each of ring A, ring D, a, b, c, d, n, m, and p can be as recited for Formulas IA and/or IB, and each n' independently can be selected from 0 to 100, such as 1 to 50, or 1 to 25, or 1 to 10, or 1 to 5.

In some embodiments, the functionalized nanohoop compounds can have structures satisfying any one or more of Formulas IIA-IIE, illustrated below.

Formula IIA

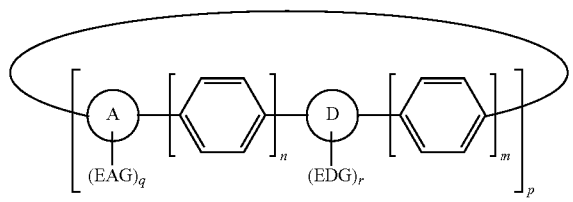

Formula IIB

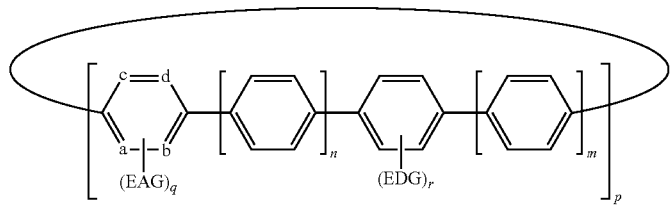

Formula IIC

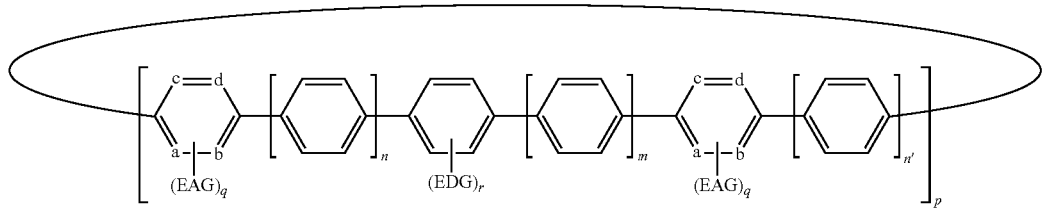

Formula IID

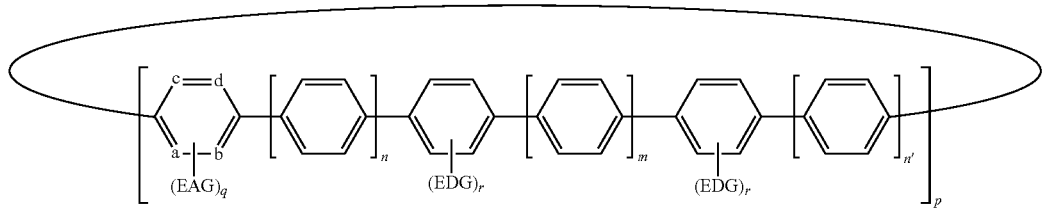

Formula IIE

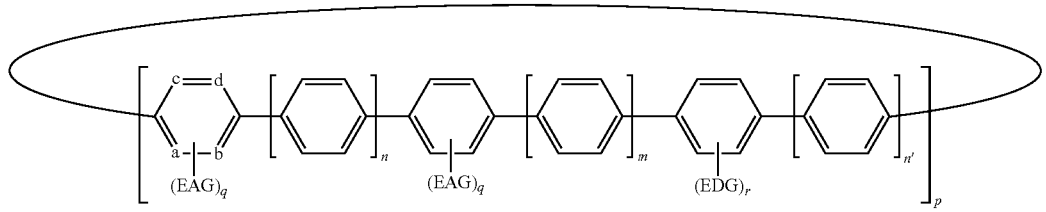

With reference to Formula IIA, the circles comprising the EAG and EDG groups can be aryl or heteroaryl rings. With reference to each of Formulas IIA-IIE, each of a, b, c, d, n, m, n', and p can be as recited above. Also with reference to Formulas IIA-IIE, the "EDG" group represents an electron-donating group and can be selected from functional groups capable of donating at least a portion of its electron density into the ring to which it is directly attached, such as by resonance. Exemplary electron-donating groups can be selected from, but not limited to, one or more of the following: alkoxy, thioether, amide, amine, hydroxyl, thiol, acyloxy, aliphatic (e.g., alkyl, alkenyl, alkynyl), aryl, or combinations thereof; the "EAG" group represents an electron-accepting group and can be selected from functional groups capable of accepting electron density from the ring to which it is directly attached, such as by inductive electron withdrawal. Exemplary electron-accepting groups can be selected from, but not limited to, one or more of the following: aldehyde, ketone, ester, carboxylic acid, acyl, acyl halide, cyano, sulfonate, nitro, nitroso, quaternary amine, pyridinyl (or pyridinyl wherein the nitrogen atom is functionalized with an aliphatic or aryl group), alkyl halide, or combinations thereof. Each variable q can be selected from 0 to 4, such as 1 to 4, or 2 to 4, with particular embodiments being zero or 1. Each variable r can be selected from 0 to 4, such as 1 to 4, or 1 or 2, with exemplary embodiments being 0, 1, or 2.

In yet additional embodiments, the functionalized nano-hoop compounds disclosed herein can have a Formula IIIA, illustrated below, which also can have the topology indicated in Formula IIIB.

Formula IIIA

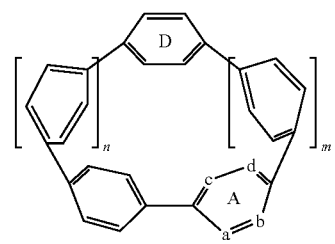

Formula IIIB

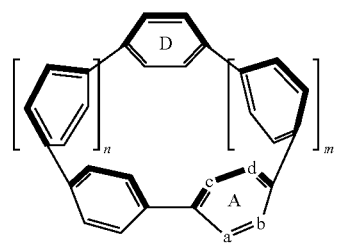

In yet additional embodiments, the functionalized nano-hoop compounds can have structures satisfying any one or more of Formulas IVA or IVB.

Formula IVA
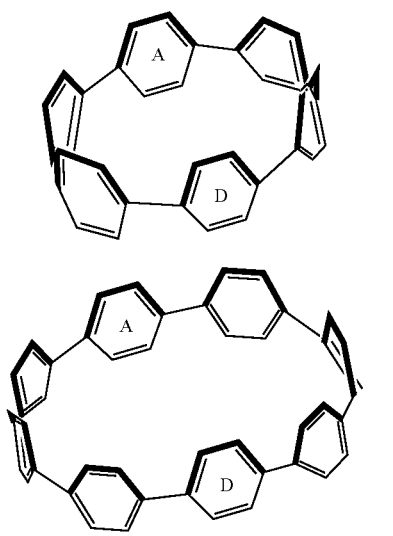
Formula IVB
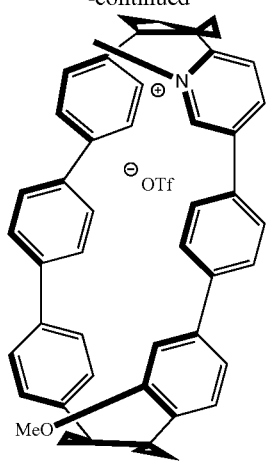
In an independent embodiment, the compound is not (or is other than) the compound illustrated below
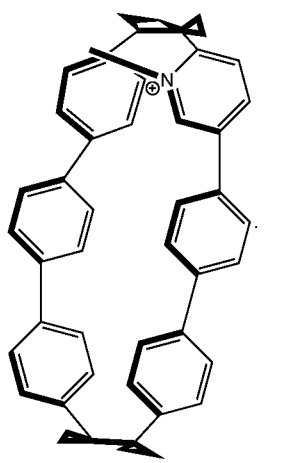
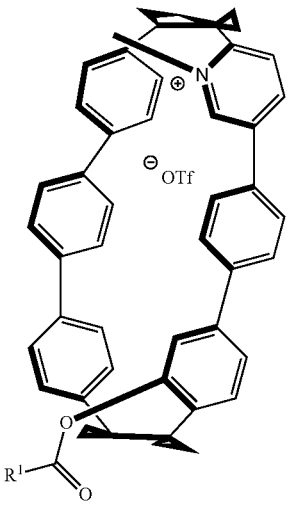
A non-limiting number of representative nanohoop compounds satisfying formulas described herein are illustrated below.
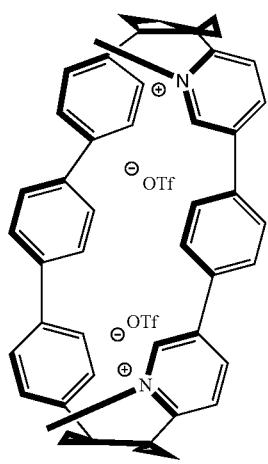
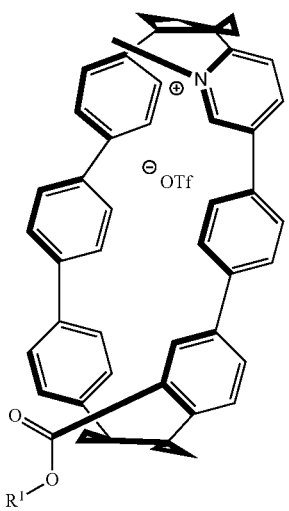

-continued
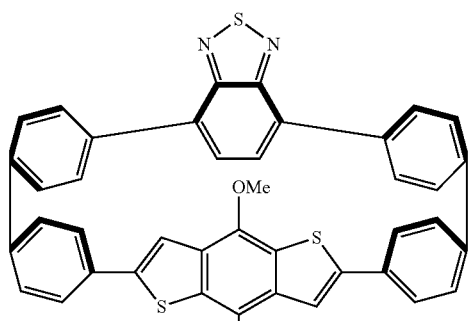
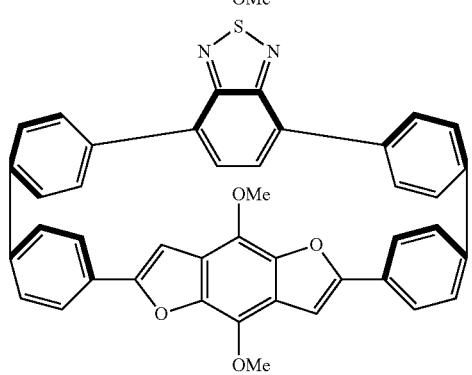
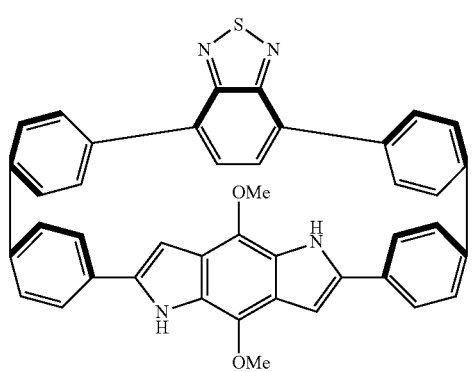
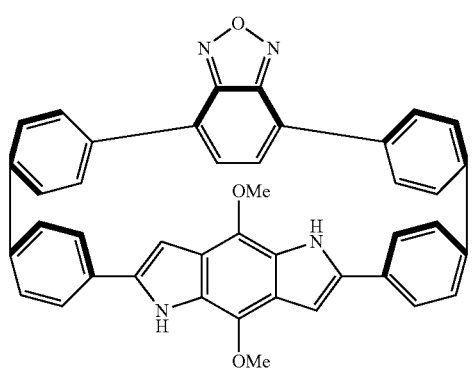
-continued
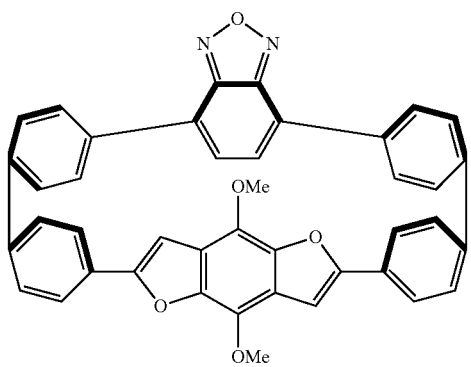
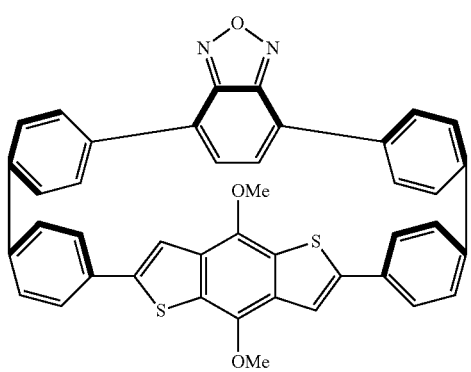
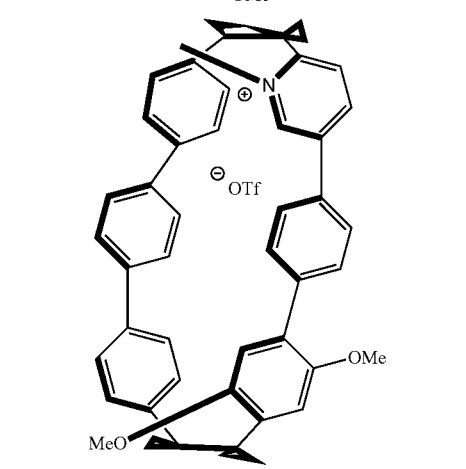
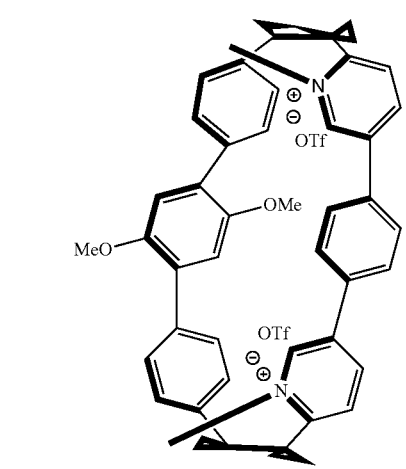

-continued
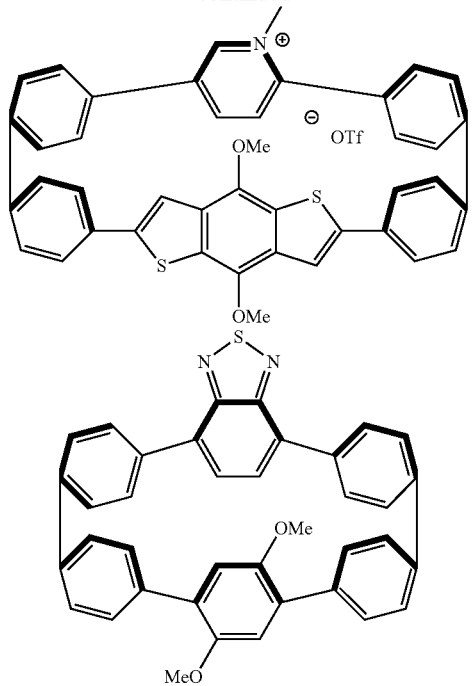
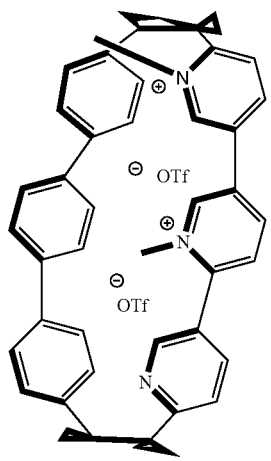
-continued
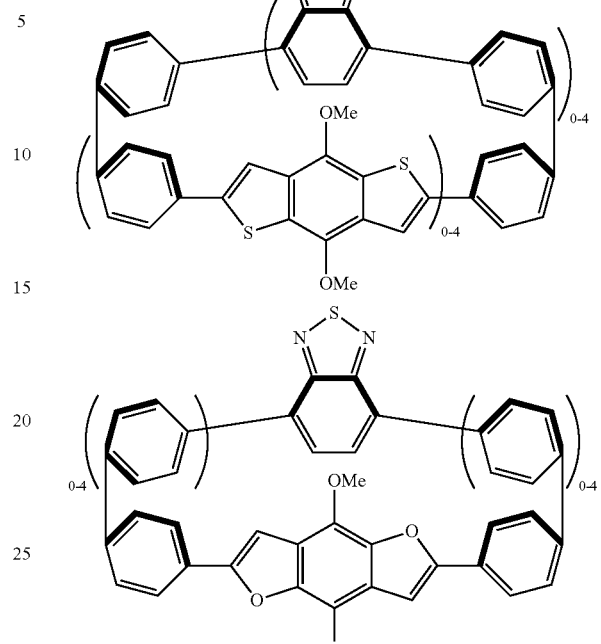
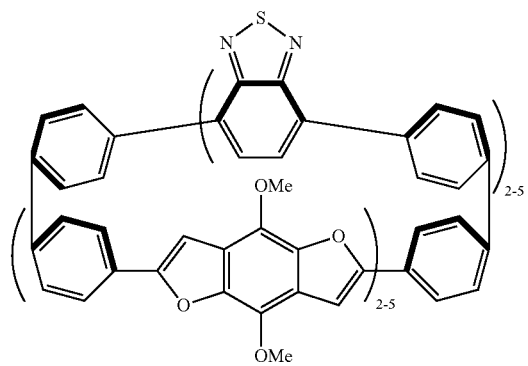
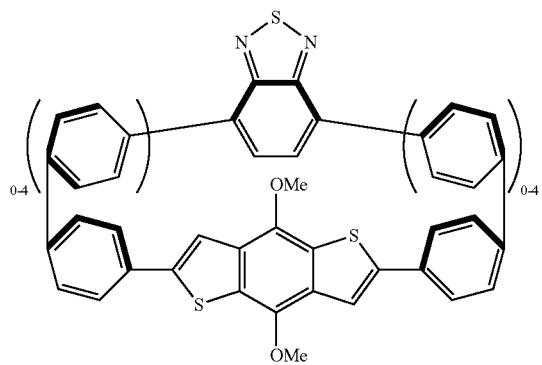
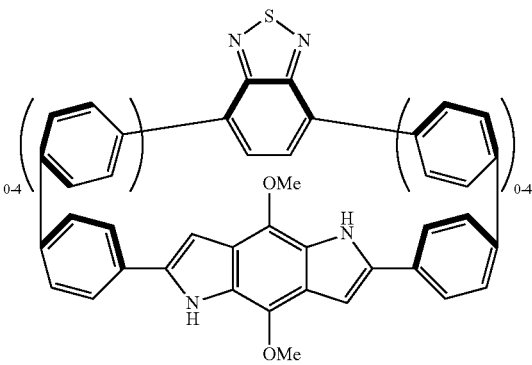

-continued

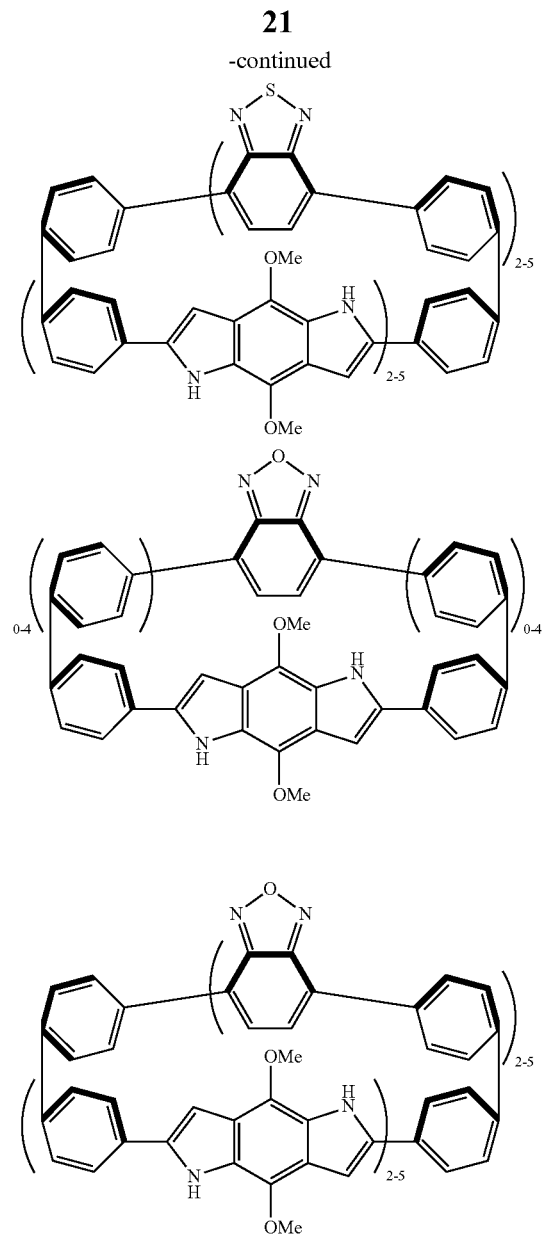

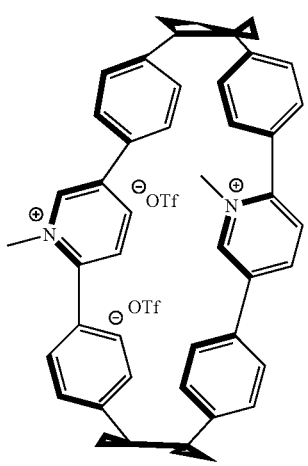

-continued

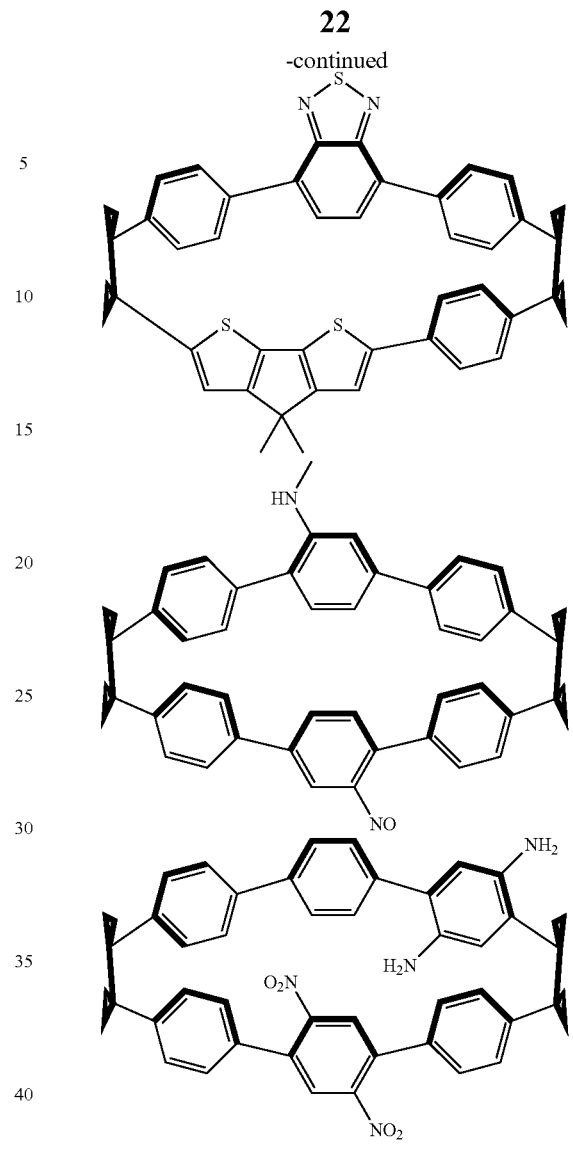

IV. Methods of Making Functionalized Nanohoop Compounds

Methods of making functionalized nanohoop compounds are disclosed herein. Functionalized nanohoop compounds can be made using embodiments of a scalable and modular method of synthesis, which utilizes the orthogonality of aryl halides to halogen-metal exchange.

Methods of making functionalized nanohoop compounds disclosed herein are illustrated below in the following schemes. In some embodiments, the synthesis of the disclosed functionalized nanohoop compounds utilizes a dihalo or diboronate macrocyclic precursor containing alternating oxidatively dearomatized cyclohexadiene moieties and arenes. Macrocylization can then be achieved either by using boron-mediated cross coupling reactions (e.g., Suzuki-Miyaura cross-coupling) or oxidative homocoupling reactions. In some embodiments, macrocycles with varying nitrogen content can be assembled by selective Suzuki-Miyaura cross-coupling between appropriately designed coupling partners (Scheme 1). Such methods also may be adapted or modified to incorporate exemplary electron donor units and/or electron acceptor units described herein.

Scheme 1

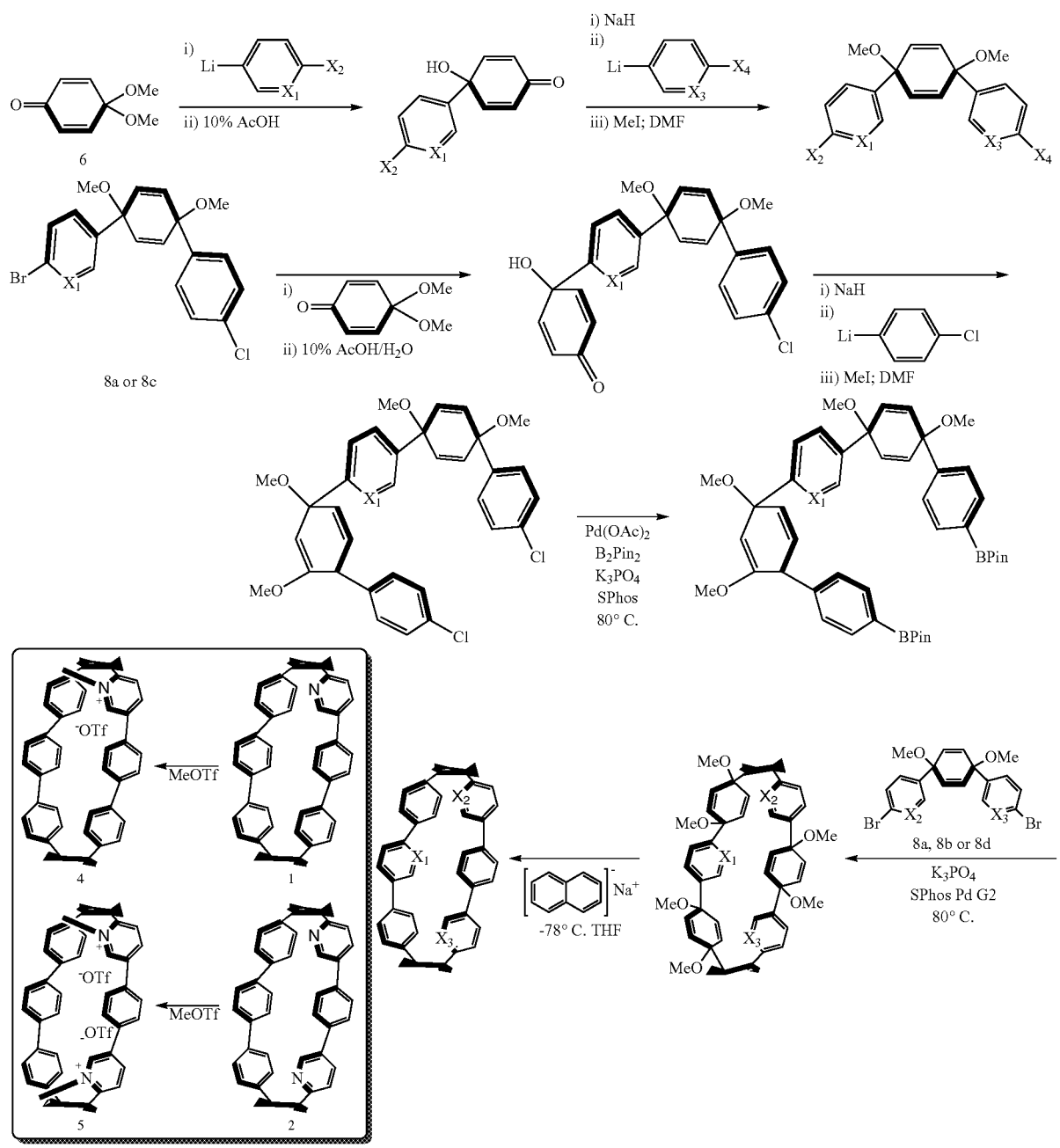

With reference to Scheme 1, each of $X_1$, $X_2$, and $X_3$ independently can be selected from carbon or nitrogen.

In some embodiments, compounds having a structure satisfying Formula V (illustrated below) can be made according to the methods described in Scheme 1 (and with specific embodiments being illustrated in Scheme 2). Compounds having structures satisfying Formula V can be exposed to a reducing agent to provide a compound according to any one of the formulas described herein. The reducing agent can be an organic salt, such as a metal naphthalenide. In some embodiments, the reducing agent can be sodium naphthanelide.

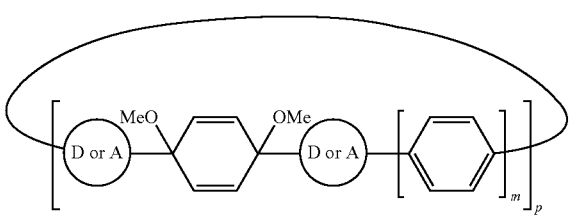

Formula V

In some embodiments, the methods of making the nanohoop compounds disclosed herein are modular and therefore can easily be modified to include different combinations of electron-acceptor units and electron-donating units. For example, any of the aryl rings described above in Scheme 1 (and described below in Scheme 2), can be substituted with one or more electron-accepting groups or one or more electron-donating groups. Also, each aryl ring also can replaced with an electron-accepting unit or an electron-donating unit. Solely by way of example and with reference to Schemes 1 or 2, each ring comprising an "X" group can be substituted with an electron-donating group or an electron-accepting group in any of the available positions on the ring comprising the "X" variable, or any combination of positions. In yet additional embodiments, each ring comprising an "X" group can be replaced with an electron-accepting unit or an electron-donating unit, and more than one type of such units can be included in any combination. In yet additional embodiment, electron-accepting units and electron-donating units can be positioned adjacent to each other and/or rings comprising electron-donating groups and rings comprising electron-accepting groups can be positioned adjacent to one another. In yet additional embodiments, electron-accepting units or rings comprising an electron-accepting group can be adjacent to one another, as can electron-donating units or rings comprising electron-donating groups.

In an exemplary embodiment, particular compounds were made using the following methods illustrated in Scheme 2.

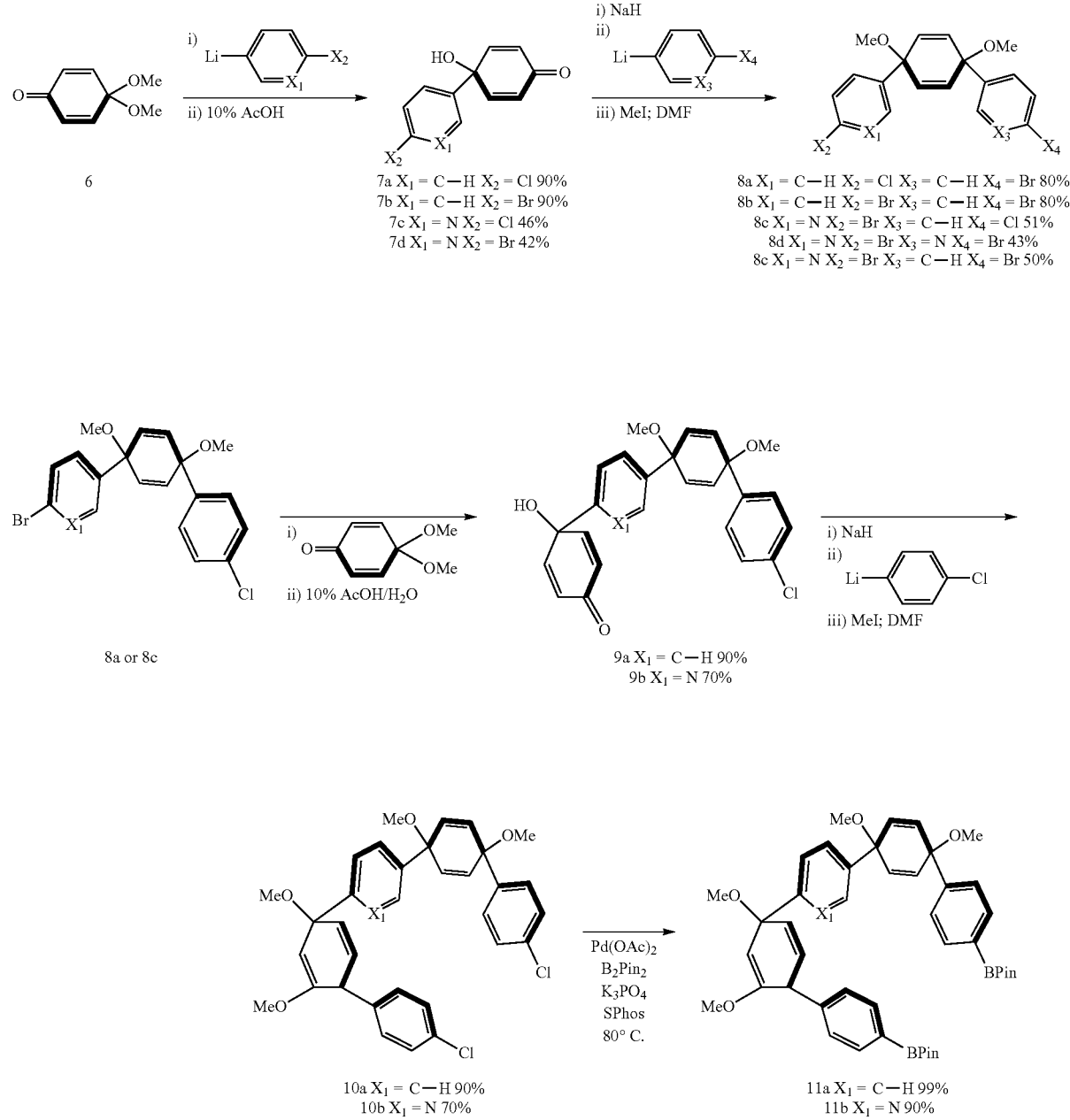

-continued

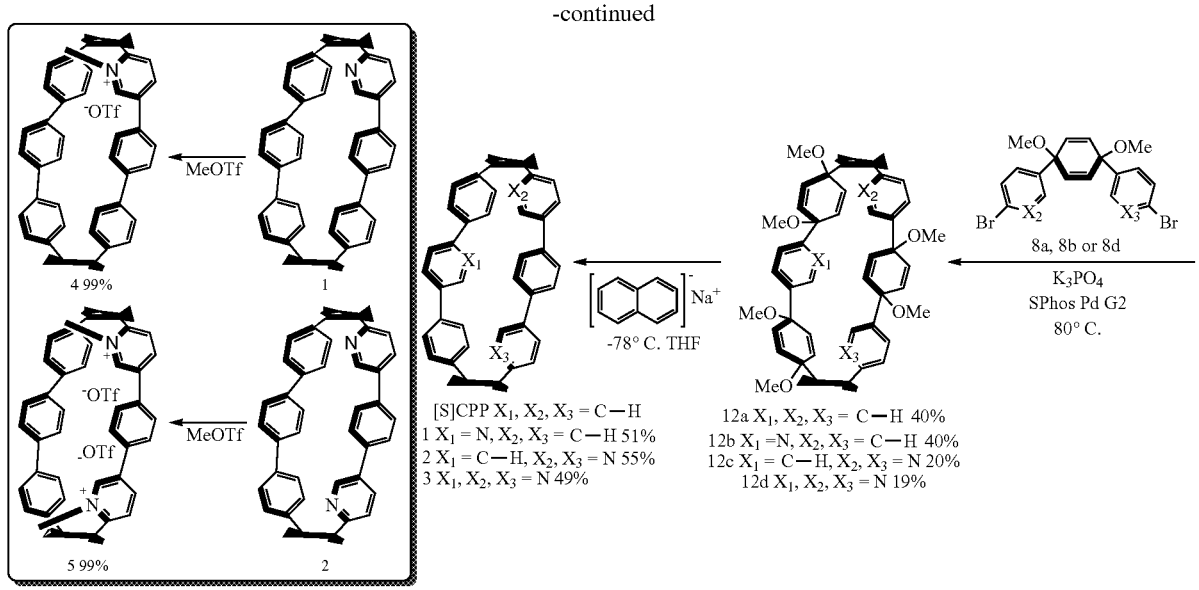

The synthesis of three-ring intermediates 8a-e is summarized in Scheme 2 and begins with the addition of 4-chlorophenyllithium, 4-bromophenyllithium, 6-chloro-3-pyridinyllithium, or 6-bromo-3-pyridinyllithium to benzoquinone monoketal 6 followed by acid catalyzed ketal deprotection to give aryl quinols 7a-d. Quinols 7a-d are then deprotonated with sodium hydride and subjected to nucleophilic addition by the appropriate lithio haloarene to give the syn three-ring fragments 8a-e after in situ alkylation of the lithio alkoxides with methyl iodide. Regioselective lithiation of 2,5-dibromopyridine can be selectively achieved in the 5 position under kinetic control in coordinating solvents, such as THF. X-ray crystallographic analysis of 8e can be used to confirm the position of the nitrogen atoms and the syn configuration of the arenes (FIG. 1). 8a and 8c are then treated with n-butyllithium and quenched with quinone monoketal 6 followed by acid catalyzed ketal deprotection to give four-ring quinols 9a and 9b, respectively. Quinols 9a and 9b are then treated with sodium hydride and subjected to nucleophilic addition of 4-bromophenyllithium followed by alkylation with methyl iodide to afford five-ring dichlorides 10a and 10b, respectively. Five-ring dichlorides 10a and 10b are then transformed to the corresponding bisboronates 11a and 11b through a Miyaura borylation with $Pd(OAc)_2$, SPhos, and $B_2Pin_2$.

Suzuki-Miyaura cross-coupling of five-ring bisboronates (11a or 11b) and three-ring dibromides (8a, 8b, or 8d) can be achieved using Buchwald's $2^{nd}$ generation SPhos precatalyst to give macrocycles 12a-d in moderate yield (Scheme 2). These macrocycles are then subjected to sodium naphthalenide at −78° C. for 30 minutes at which point they are quenched with $I_2$ to give [8]CPP, aza[8]CPP 1, 1,15-diaza [8]CPP 2, and 1,15,31triaza[8]CPP 3. Compounds 1 and 2 are then treated with methyl triflate in dry dichloromethane to afford mono alkylated N-methylaza[8]CPP triflate 4 and N,N-dimethyle-1,15-diaza[8]CPP ditriflate 5 quantitatively. Compounds 1-5 can be characterized using $^1H$ and $^{13}C$ NMR spectroscopy, and mass spectrometry.

V. Features and Properties of Nanohoop Compounds and Methods of Using Nanohoops In particular disclosed embodiments, different techniques can be used to evaluate the structural features and chemical and/or electrochemical properties of the functionalized nanohoop compounds disclosed herein. In some embodiments, solid state analysis of the compounds can be utilized to evaluate particular characteristics of the nanohoop compounds, such as their ability to interact, pack, and/or facilitate charge transport. Exemplary solid state analysis techniques are discussed below.

Figure 2:
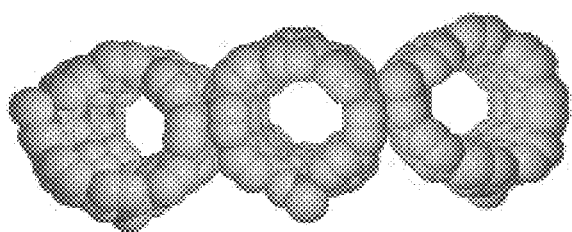
FIG. 2 illustrates different configurations of a functionalized nanohoop embodiment illustrating a calculated crystal structure (left); a side-on packing configuration of a plurality of functionalized nanohoops (middle); and a top-down packing configuration of a plurality of functionalized nanohoops (right).
Figure 2:
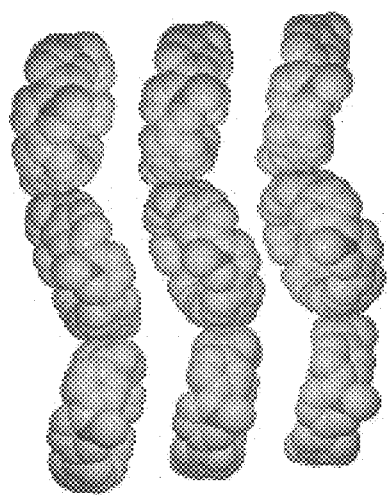
Figure 2:
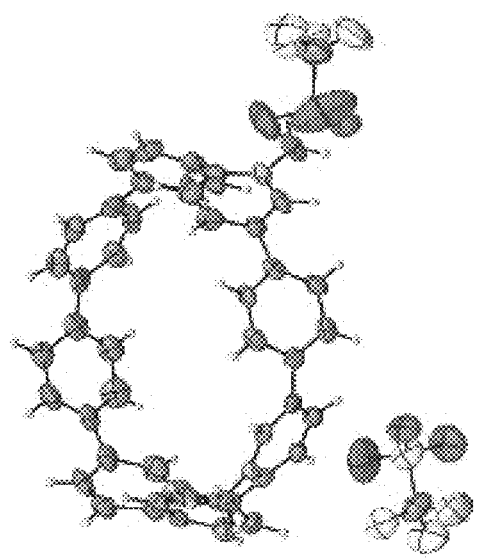
Figure 3:
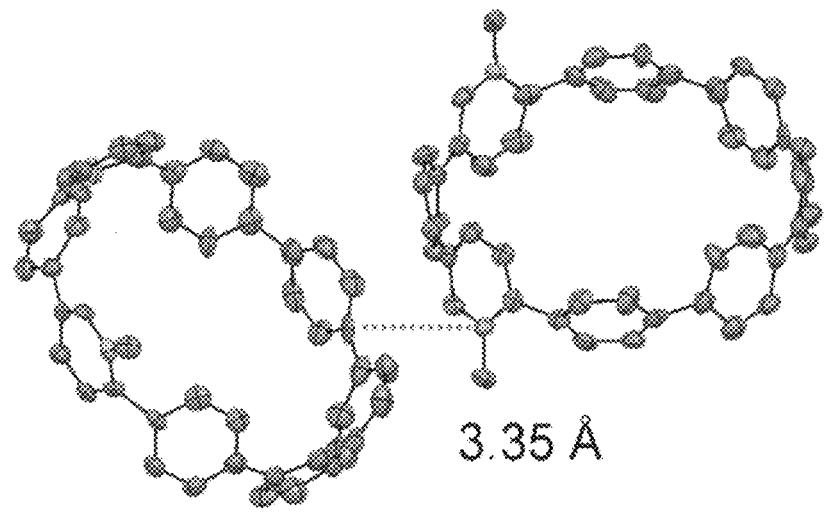
FIG. 3 illustrates a head to tail interaction between an acceptor unit of one nanohoop compound and a donating unit of another nanohoop compound.
Figure 28:
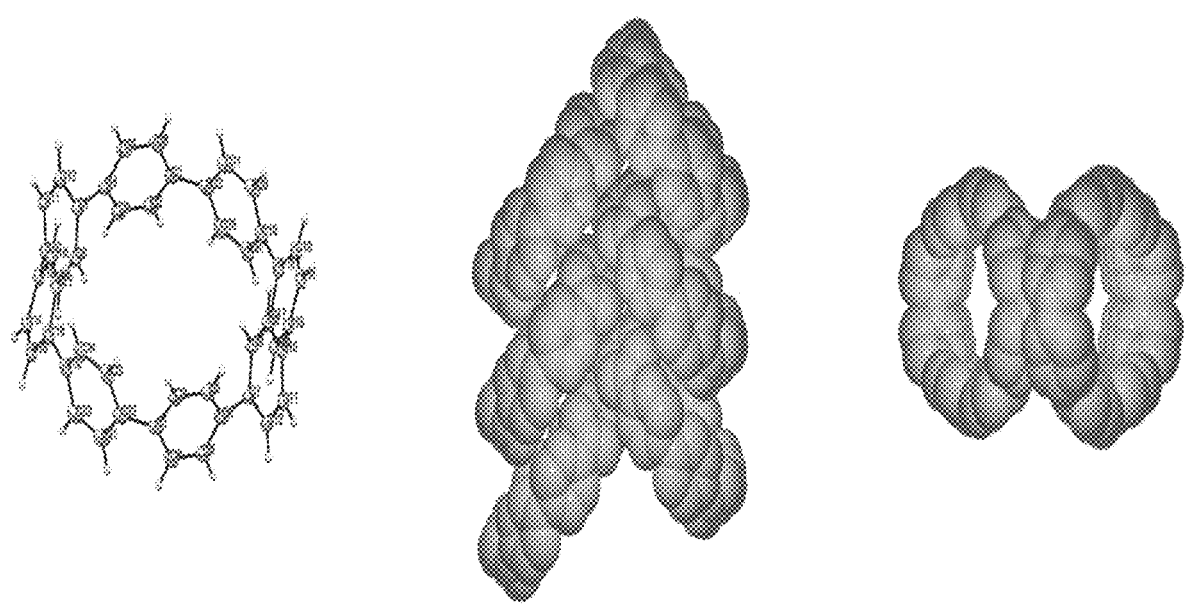
FIG. 28 illustrates various configurations for a non-functionalized nanohoop compound, illustrating an ORTEP representation of a non-functionalized nanohoop compound (left), a side-on packing configuration of a plurality of non-functionalized nanohoops (middle), and a top-down packing configuration of a plurality of non-functionalized nanohoops (right).
Figure 29A:
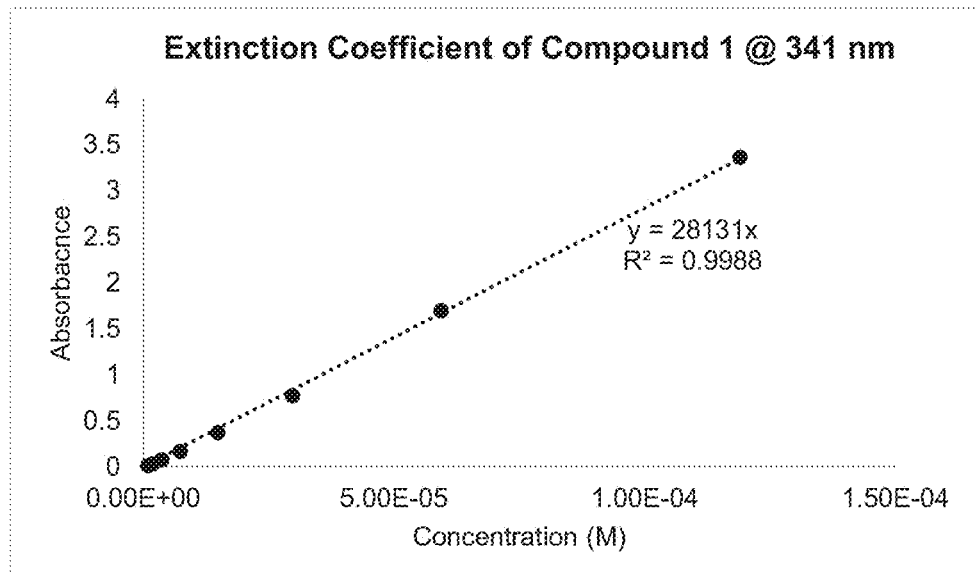
FIGS. 29A and 29B are Beer-Lambert plots of compound 1 at 341 nm ($\varepsilon$=2.8×10$^4$ M$^{-1}$ cm$^-$) (FIG. 29A), and at 400 nm ($\varepsilon$=0.25×10$^4$ M$^{-1}$ cm$^{-1}$) (FIG. 29B).
Figure 29B:
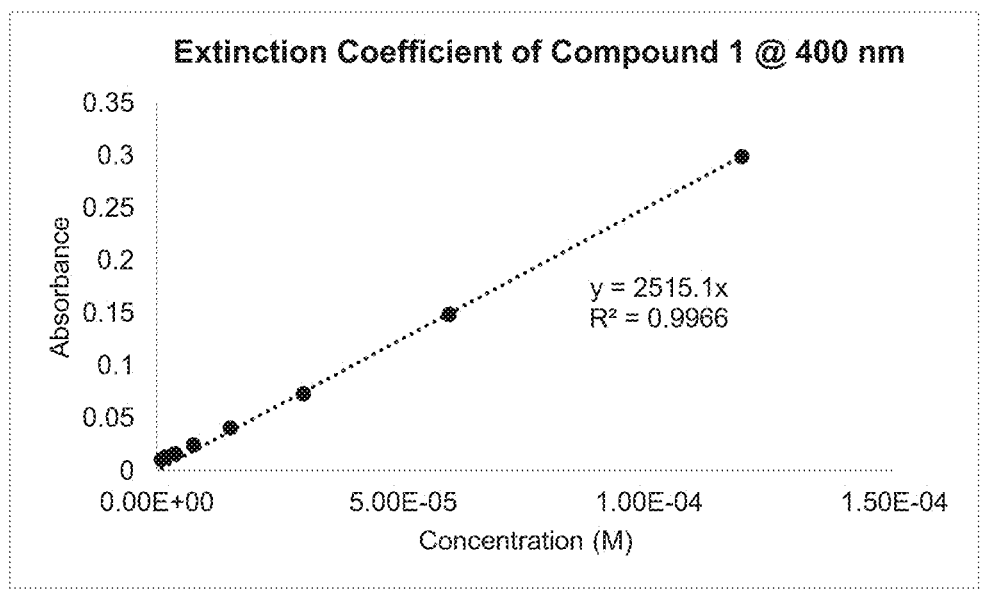
Figure 30A:
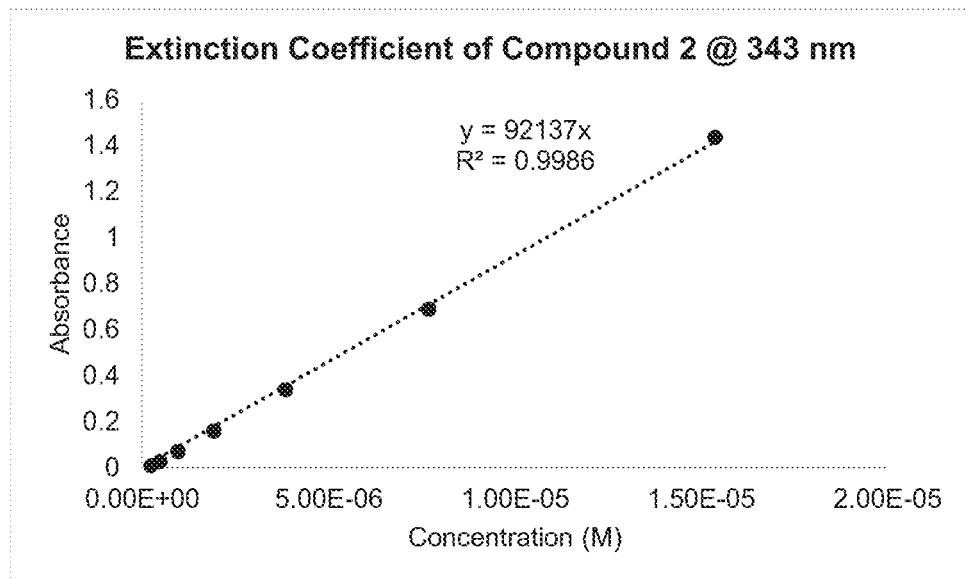
FIGS. 30A and 30B are Beer-Lambert plots of compound 2 at 343 nm ($\varepsilon$=9.2×10$^4$ M$^{-1}$ cm$^-$) (FIG. 30A) and at 400 nm ($\varepsilon$=0.73×10$^4$ M$^{-1}$ cm$^{-1}$) (FIG. 30B).
Figure 30B:
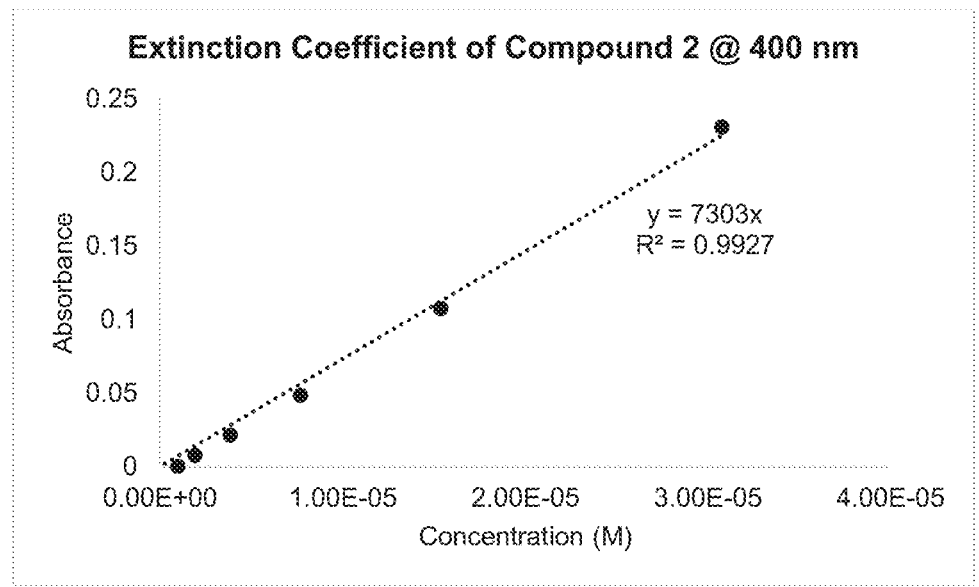
Figure 31A:
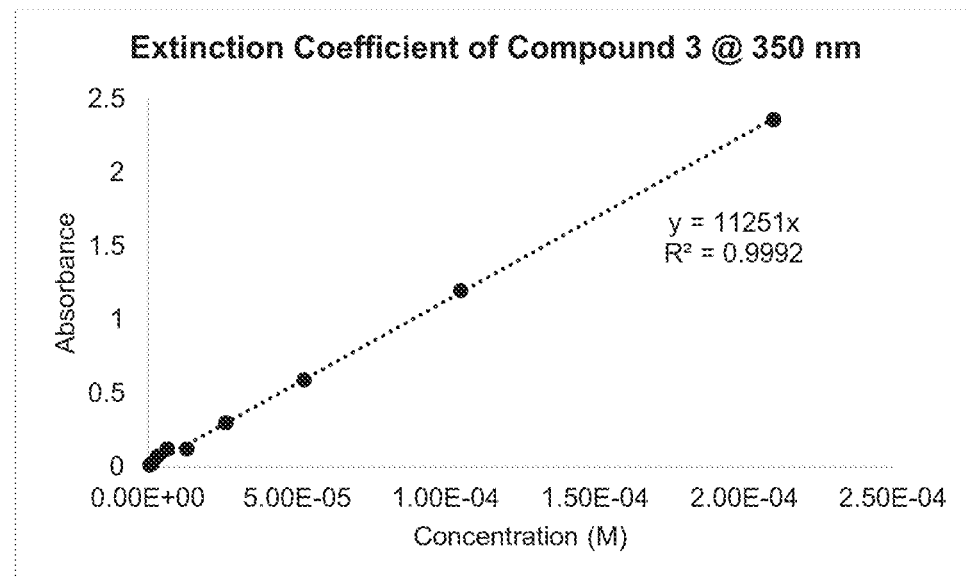
FIGS. 31A and 31B are Beer-Lambert plots of compound 3 at 350 nm ($\varepsilon=1.1\times10^4$ $M^{-1}$ $cm^-$) (FIG. 31A) and at 400 nm ($\varepsilon=0.089\times10^4$ $M^{-1}$ $cm^{-1}$) (FIG. 31B).
Figure 31B:
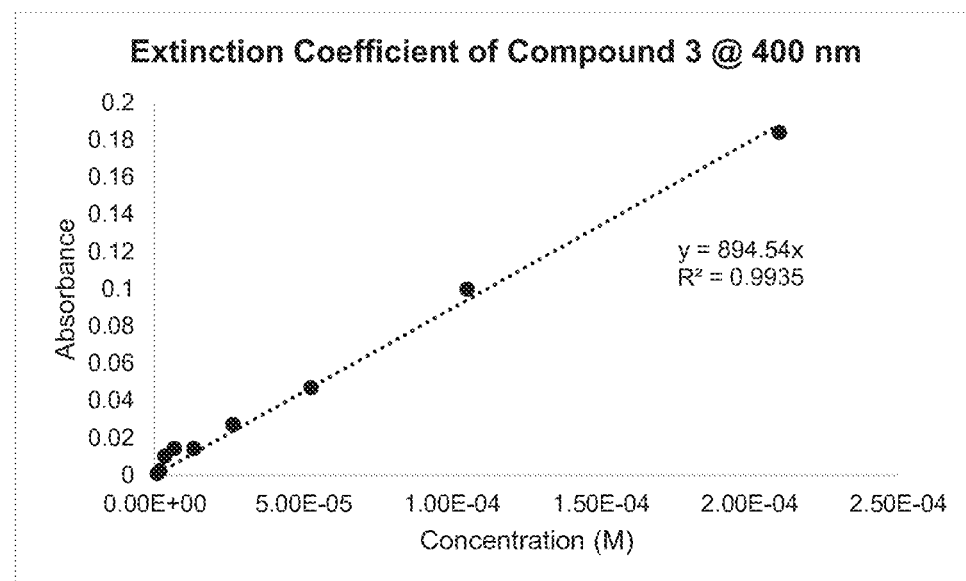
Figure 32A:
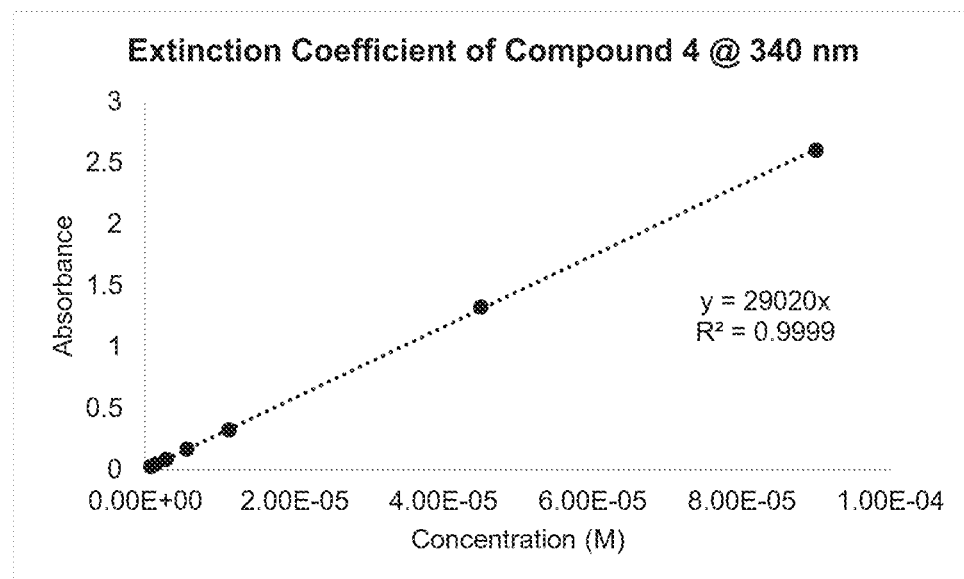
FIGS. 32A and 32B are Beer-Lambert plots of compound 4 at 340 nm ($\varepsilon=2.9\times10^4$ $M^{-1}$ $cm^-$) (FIG. 32A) and at 450 nm ($\varepsilon=0.019\times10^4$ $M^{-1}$ $cm^-$) (FIG. 32B).
Figure 32B:
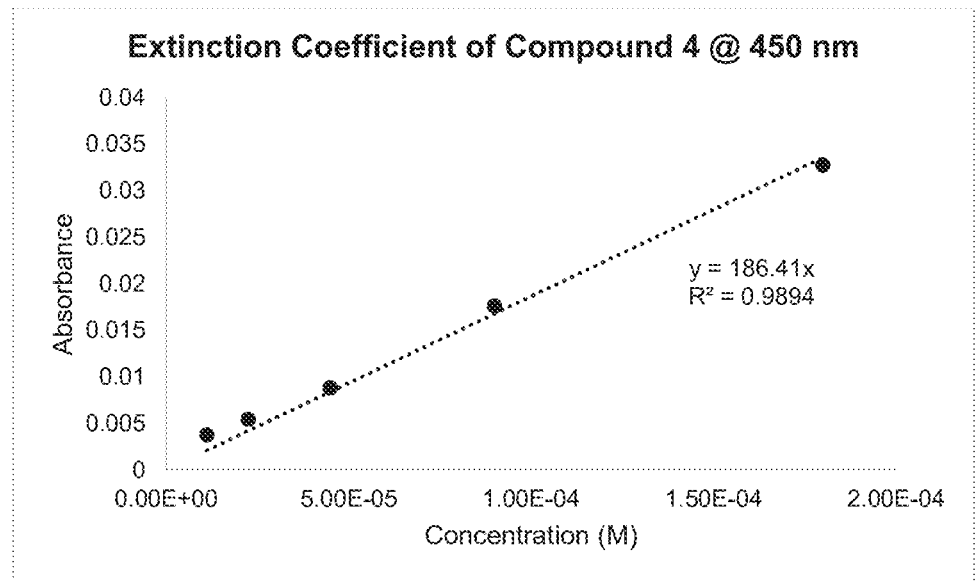
Figure 33A:
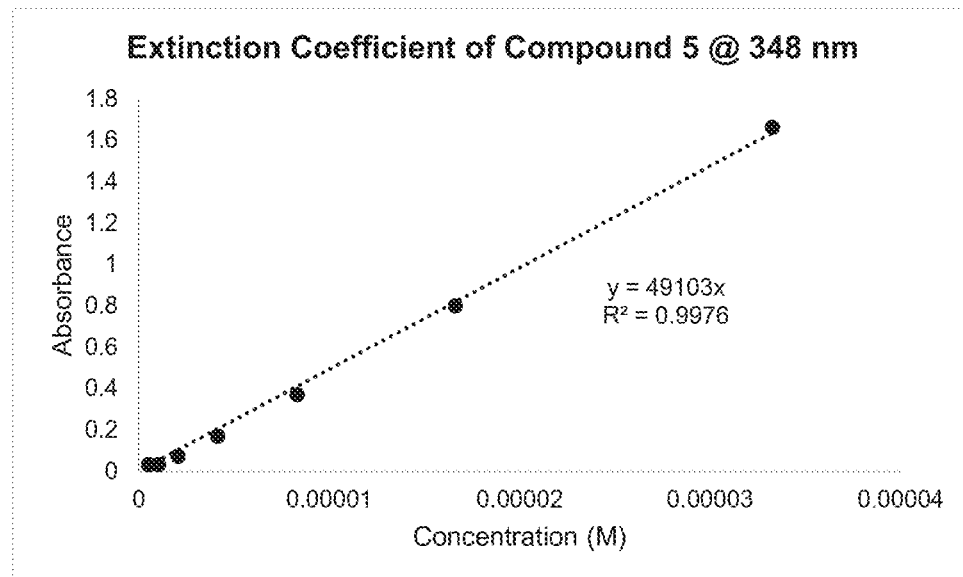
FIGS. 33A-33C are Beer-Lambert plots of compound 5 at 348 nm ($\varepsilon=4.9\times10^4$ $M^{-1}$ $cm^{-1}$) (FIG. 33A), at 400 nm ($s=5.5\times10^4$ $M^{-1}$ $cm^{-1}$) (FIG. 33B), and at 450 nm ($\varepsilon=0.98\times10^4$ $M^{-1}$ $cm^{-1}$) (FIG. 33C).
Figure 33B:
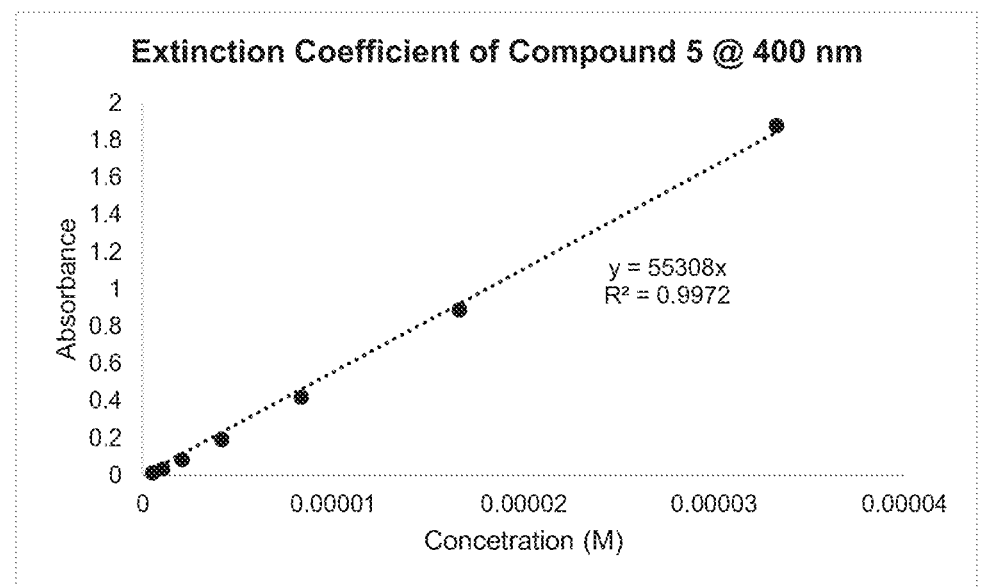
Figure 33C:
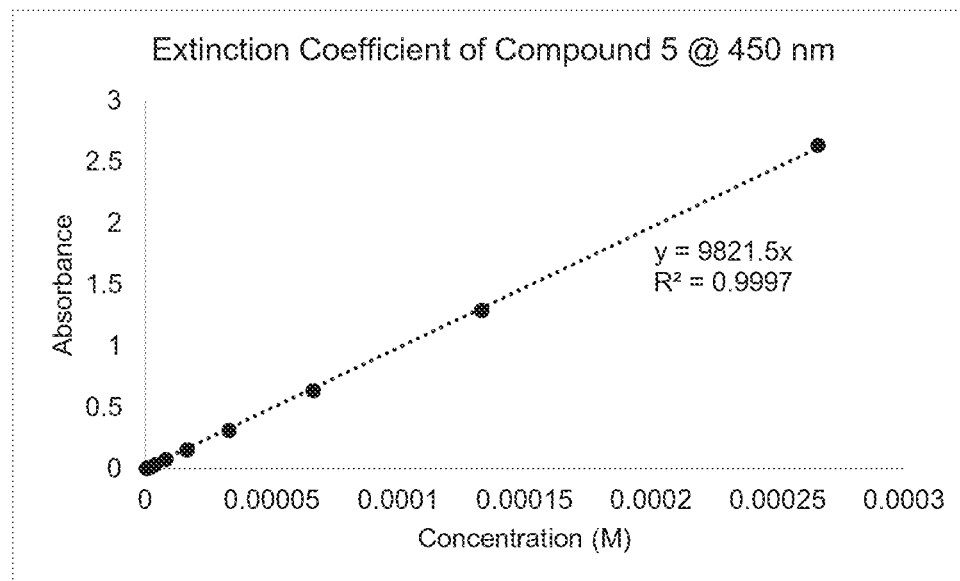

In some representative embodiments, single-crystal X-ray structure determination was performed on compounds 1 and 5. FIG. 2 shows an ORTEP, packing structure, and exemplary unique interactions for a representative compound. Another ORTEP image is illustrated in FIG. 28, wherein a non-functionalized nanohoop compound is illustrated. Solid state packing can impact material properties, such as charge transport in organic materials. In some embodiments, the nitrogen atom of compound 1 was determined to be disordered over 32 possible locations in the solid state. The incorporation of a single nitrogen atom in compound can result in a herringbone crystal packing motif. In contrast, compound 5 had a dramatically different packing structure compared to compounds 1-3. The dipole moment of these alkylated nanohoops far exceeds conventional nanohoop compounds and further exhibits a new supramolecular design motif for their solid state structures. Compound 5 was determined to be more ordered in some embodiments, adopting a trans relationship for the N-methylpyridinium triflate rings. In an exemplary embodiment, each nanohoop in the crystal structure has one face centered donor-acceptor interaction between its own pyridinium ring and a neighbor's electron rich phenylene ring. In an exemplary embodiment, the shortest contact between such neighboring subunits was 3.35 Å (FIG. 3). Such head to tail packing results in a 2D plane as shown in FIG. 2. The layers making-up the $3^{rd}$ dimension of the crystal structure form tubular channels, which can be occupied with ordered chloroform solvent molecules from which the crystals were grown.

Figure 4:
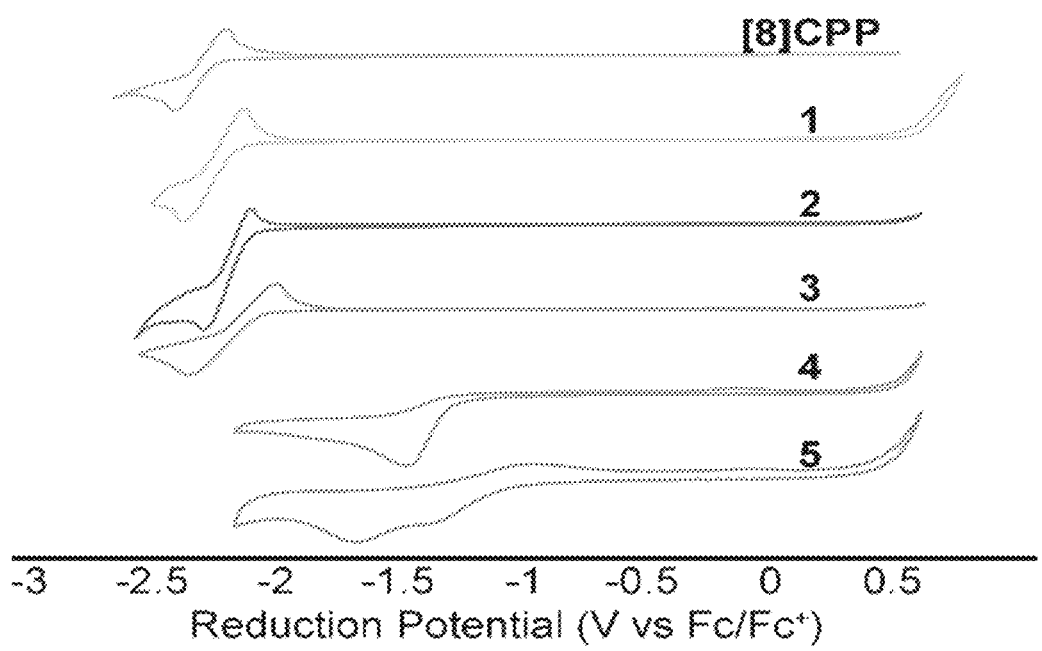
FIG. 4 is a voltammogram illustrating results of obtained from cyclic voltammetric analysis of representative non-functionalized nanohoop embodiments [8]CPP and compounds 1-3, and representative functionalized nanohoop compounds 4 and 5.

In additional embodiments, the electrochemical properties of the functionalized nanohoop compounds disclosed herein can be evaluated. In some embodiments, cyclic voltammetry (CV) was used to probe the reduction properties of the functionalized nanohoops (e.g., compounds 4 and 5). In some embodiments, analysis also was performed for an [8]CPP compound in addition to functionalized nanohoop compounds (e.g., compounds 1-5). In exemplary embodiments, peak potentials of −2.44 V ([8]CPP), −2.39 V (compound 1), −2.32 V (compound 2), and −2.39 V (compound 3) versus the ferrocene/ferrocenium couple were observed. Compound 4 exhibited a reduction peak potential at −1.49 V while compound 5 had two reduction events with peak potentials recorded at −1.36 V and −1.49 V versus the ferrocene/ferrocenium couple. The spectra for these compounds can be seen in FIG. 4.

The functionalized nanohoop compounds disclosed herein can be made to have unique electrochemical properties that facilitate their use in different applications, such as electrochemical devices, photovoltaic devices, and the like. In some embodiments, the functionalized nanohoop compounds exhibit electrochemical properties superior to that of a corresponding non-functionalized nanohoop compound. A non-functionalized nanohoop compound typically is a compound comprising a nanohoop skeleton made solely of phenyl rings and/or that is free of electron acceptor units and electron donor units and/or that is free of electron acceptor groups and electron donor groups. Solely by way of example, a non-functionalized nanohoop corresponding to functionalized nanohoop compound 4 can be [8]CPP, aza [8]CPP (e.g., compound 1), and/or protonated aza[8]CPP (e.g., compound 1 further quaternized with a proton). In some embodiment, the functionalized nanohoop compounds can exhibit lower LUMO energy levels and/or lower HOMO energy levels as compared to a corresponding non-functionalized nanohoop. In some embodiments, the functionalized nanohoop compounds can exhibit LUMO energy levels between greater than −2.0 eV to −5 eV, such as −2.5 eV and −4.0 eV, or −2.9 eV and −3.5 eV, or −2.9 eV and −3.0 eV. In some embodiments, the functionalized nanohoop compounds can exhibit HOMO energy levels between −5.0 eV and −7 eV, such as −5.2 eV and −6.5 eV, or −5.7 eV and −6.0 eV. In particular disclosed embodiments, the functionalized nanohoop compounds can exhibit HOMO energy levels greater than −5.5 eV.

In some embodiments, the functionalized nanohoop compound is capable of exhibiting a LUMO energy level that is 0.5 eV to 1.4 eV lower than a LUMO energy level of a corresponding non-functionalized nanohoop compound. In yet additional embodiments, the functionalized nanohoop compound exhibits a HOMO energy level that is 0.1 eV to 2 eV lower than a HOMO energy level of a corresponding non-functionalized nanohoop compound.

Figure 5:
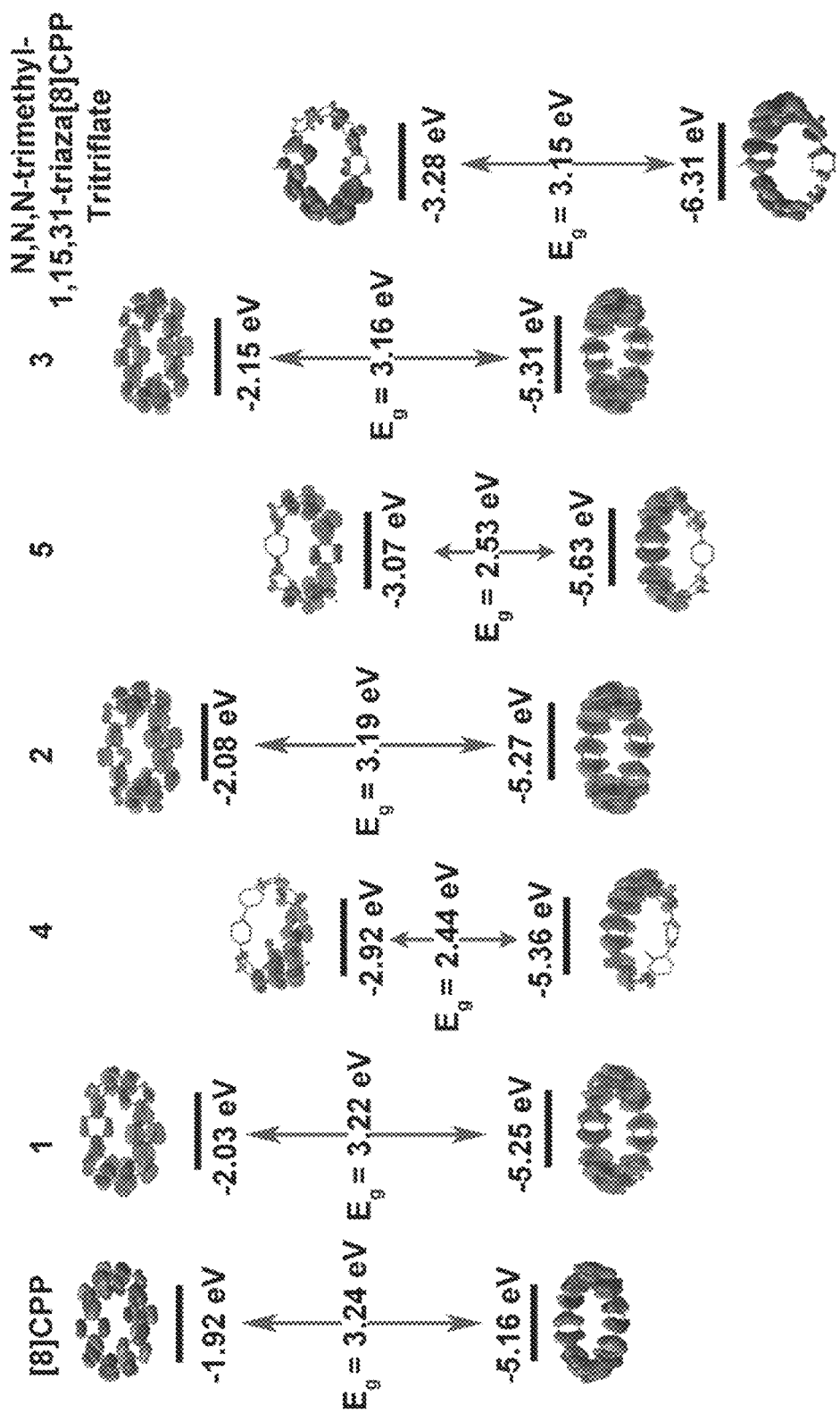
FIG. 5 is an image illustrating DFT HOMO and LUMO energy levels and orbital distributions for representative non-functionalized nanohoop embodiments [8]CPP and compounds 1-3, and representative functionalized nanohoop compounds 4, 5, and N,N,N-trimethyl-1,15,31-triaza[8]CPP tritriflate.

In some embodiments, as the nitrogen content increases the reduction potentials show a slight shift to less negative voltage in accordance with the added electronegativity gained. Substitution (e.g., quaternizing a nitrogen atom with an aliphatic group) results in a much more dramatic shifting to less negative reduction potentials in accordance with DFT results (FIG. 5). Calculations show a steady decrease in both HOMO and LUMO energies of approximately 0.07 eV from [8]CPP to compounds 1, 2, and 3. Visualization of the HOMO and LUMO orbitals showed nearly complete delocalization around the entire hoop showing only a slight increase in orbital coefficient around the nitrogen containing rings. The concerted lowering of both the HOMO and LUMO orbital energies can be understood by their even delocalization over the electronegative nitrogen. Alkylated compounds 4 and 5 and computationally investigated compound N,N,N-trimethyl-1,15,31-triaza[8]CPP exhibited a dramatic lowering of the LUMO energy level by 1.00 eV, 0.870 eV, and 1.15 eV respectively relative to [8]CPP. The one (compound 4) and two nitrogen (compound 5) analogs exhibited a lowering of the HOMO energy by 0.200 eV and 0.470 eV, respectively. These results are similar to the predicted reduction for compound 4 and compound 5, which exhibited dramatic lowering of the reduction potential. In some embodiments, the triply alkylated N,N,N-trimethyl-1, 15,31-triaza[8]CPP HOMO energy can drop a full 1.15 eV. Visualization of the HOMO and LUMO orbitals can help explain these trends. Without being limited to a particular theory, it is currently believed that in both the mono- and bis-alkylated structures, compound 4 and compound 5, there is a significant dipole moment and localization of the LUMO on the N-methylpyridinium core. The HOMO meanwhile is localized on the phenylene backbone with orbital coefficients reaching the highest values directly opposite the N-methylpyridinium rings. With minimal contribution from the N-methylpyridinium, the HOMO energies reflect the similarity in both geometry and electronic structure of the neutral analogues 1-3. The calculated N,N,N-trimethyl-1,15, 31-triaza[8]CPP on the other hand has a much lower dipole moment and the HOMO and LUMO orbitals spread over both the phenylene and pyridinium sections. This results in a concerted dropping of the HOMO and LUMO orbital energies by over one eV while maintaining a similar HOMO-LUMO energy gap as the parent compound 1,15, 31-triaza[8]CPP (compound 3). These results indicate that the position of the N-methylpyridinium rings in relation to one another can affect modulation of the frontier molecular orbital energies.

Figure 6:
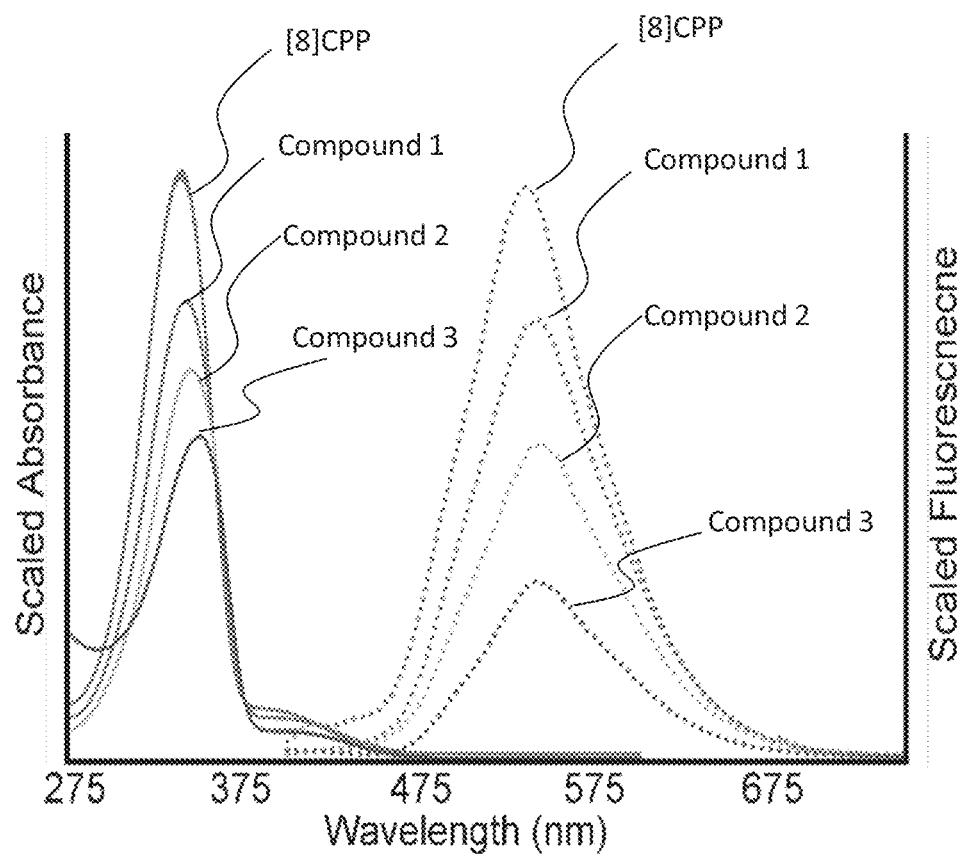
FIG. 6 is a combined UV-Vis absorbance (solid lines) and fluorescence spectrum (dashed lines) illustrating results obtained from UV-Vis and fluorescence analysis of non-functionalized nanohoop compounds [8]CPP and 1-3.
Figure 7:
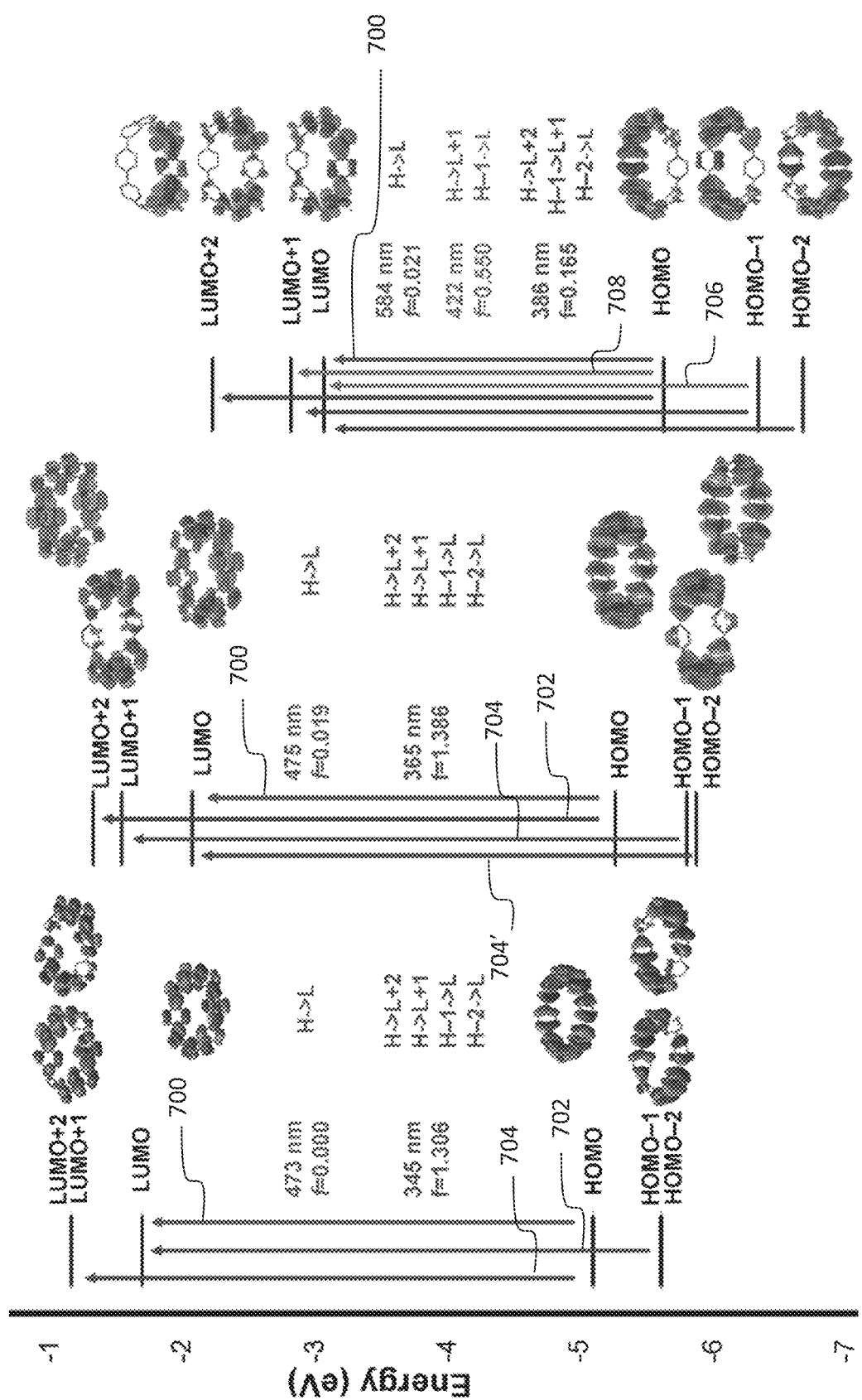
FIG. 7 is an image illustrating TD-DFT orbital transitions for non-functionalized nanohoop compounds [8]CPP (left) and compound 1 (middle) and representative functionalized nanohoop compound 5 (right).

In yet additional embodiments, the optoelectronic properties of the functionalized nanohoop compounds disclosed herein can be evaluated. In some embodiments, the UV-Vis absorption and emission spectra of [8]CPP and compounds 1-3 in dichloromethane (DCM) were evaluated. Exemplary results are depicted in FIG. 6 and summarized in Table 1. TD-DFT can also be used to determine potential photophysical trends. Some exemplary transitions are depicted in FIG. 7. Orbital contributions to major and minor absorbances also are outlined in Table 1 for exemplary embodiments. The major absorption for [8]CPP is 340 nm ($\varepsilon=1.0\times10^5$ M$^{-1}$ cm$^{-1}$). This absorbance comprises four degenerate transitions, HOMO→LUMO+1, HOMO→LUMO+2, HOMO-1→LUMO, and HOMO-2→LUMO (red transitions 704 and 701, respectively in FIG. 7). Although the HOMO→LUMO transition is formally Laporte forbidden with conservation of HOMO and LUMO orbital symmetry, it is still observed as a slight shoulder centered at 400 nm ($\varepsilon=8.5\times10^2$ M$^{-1}$ cm$^{-1}$) (purple transition, labeled as 700, in FIG. 7, left). The addition of a single nitrogen atom and any subsequent nitrogen atoms breaks the symmetry and thus the degeneracy between the HOMO-1 and HOMO-2 as well as the LUMO-1 and LUMO-2 orbital energies. Increasing nitrogen atom content in compounds 1, 2, and 3 leads to a slight red-shifting of major absorbance to 345 nm ($\varepsilon=2.5\times10^5$ M$^{-1}$ cm$^{-1}$), 349 nm ($\varepsilon=7.30\times10^5$ M$^{-1}$ cm$^{-1}$), and 353 nm ($\varepsilon=8.94\times10^5$ M$^{-1}$ cm$^-$), respectively. These absorbances can be attributed to the similar combinations of the HOMO-1→LUMO, HOMO-2→LUMO, HOMO→LUMO+1, and HOMO→LUMO+2 transitions (red transitions 702 and 704, respectively, in FIG. 7) observed for [8]CPP. The shifting of these transitions relative to [8]CPP can be accounted for by the increasing electronegative nitrogen content. The shoulder peaks for [8]CPP and compounds 1-3 around 400 nm have a measured extinction coefficient (c) of $2.5\times10^3$ M$^{-1}$ cm$^{-1}$, $7.3\times10^3$ M$^{-1}$ cm$^{-1}$, and $8.9\times10^3$ M$^{-1}$ cm$^{-1}$, respectively. These lower energy transitions are again assigned to the HOMO-LUMO absorbances (purple transitions 700 in FIG. 7), which are less forbidden with larger calculated oscillator strength and measured extinction coefficients over an order of magnitude larger than observed for [8]CPP. The emission for [8]CPP was reported at 533 nm. In accordance with the red-shifted absorbance, the fluorescence for compounds 1, 2, and 3 are shifted to 541 nm, 544 nm, and 542 nm, respectively. A prominent change in fluorescence can be observed upon substitution (e.g., alkylation) of neutral compounds 1-3.

TABLE 1

Reduction potentials, maximum absorbance, extinction coefficients, and emission maxima for [8]CPP and compounds 1-5.

| Compound | Reduction vs Fc/Fc+ (V) | Cathodic Peak Potential | Max Absorbance (nm) | Extinction Coefficient ($M^{-1}$ $cm^{-1}$) | Emission Maximum (nm) |
|---|---|---|---|---|---|
| [8]CPP | −2.29 | −2.44 | 341 | 1.00E+05 | 533 |
| 1 | −2.23 | −2.39 | 345 | 2.81E+04 | 541 |
| 2 | −2.17 | −2.32 | 349 | 9.21E+04 | 544 |
| 3 | −2.15 | −2.39 | 353 | 1.13E+04 | 542 |
| 4 | −1.48 | −1.49 | 345 | 2.90E+04 | 598 |
| 5 | −1.37, −1.67 | −1.36 | 350 | 4.91E+04 | 630 |

Figure 8:
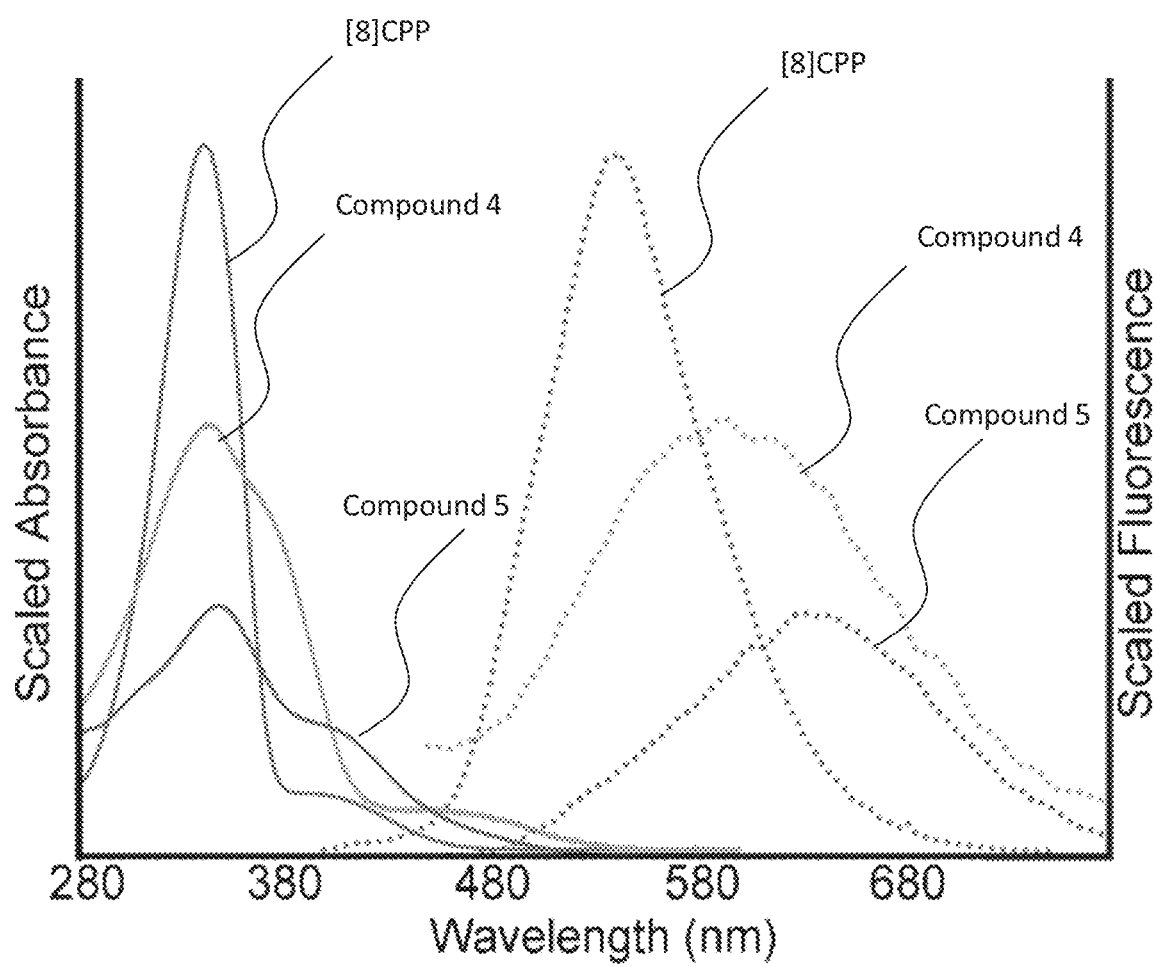
FIG. 8 is a combined UV-Vis absorbance (solid lines) and fluorescence spectrum (dashed lines) illustrating results obtained from UV-Vis and fluorescence analysis of a non-functionalized nanohoop compound ([8]CPP) and two representative functionalized nanohoop compounds (4 and 5).

Absorbance and emission spectra for alkylated compounds 4 and 5 are depicted in FIG. 8 and show even greater disparity in orbital energy difference between HOMO-1 and HOMO-2 as well as LUMO+1 and LUMO+2. This leads to three distinct absorbing regions. The major absorbance and highest energy transitions for compounds 4 and 5 are at 345 nm ($\varepsilon = 2.90 \times 10^4$ $M^{-1}$ $cm^-$) and 350 nm ($\varepsilon = 4.91 \times 10^4$ $M^{-1}$ $cm^{-1}$), respectively, and correspond to the higher energy HOMO-2→LUMO and HOMO→LUMO+2 transitions (red transitions 704' and 702 in FIG. 7). The second absorbing region is lower in energy and appears in the visible spectrum as a shoulder peak for compounds 4 and 5 between 400 nm and 425 nm. These can be assigned to the lower energy HOMO→LUMO+1 and HOMO-1→LUMO transitions (green transitions 708 and 706, respectively in FIG. 7). The HOMO-LUMO transitions (purple transitions 700 in FIG. 5) are calculated to have low, yet non-zero oscillator strengths and are still symmetry forbidden. This peak is observed as a weak low energy feature at 460 nm and 554 nm for compounds 4 and 5, respectively. Although alkylated compounds 4 and 5 were nearly non-emissive, a red-shifted fluorescence was observed at 598 nm and 630 nm, respectively. This is nearly a 100 nm shift from the formally neutral species which emit around 542 nm. This correlates well with the theoretical difference in the HOMO-LUMO energy gap between the neutral compound ([8]CPP and compounds 1-3) and the alkylated compounds (compounds 4 and 5). This observation supports that emission likely occurs from the lowest energy excited $S_1$ state in accordance with Kasha's rule or a vibrationally relaxed excited state S' as postulated by Tretiak et. al.

Figure 9:
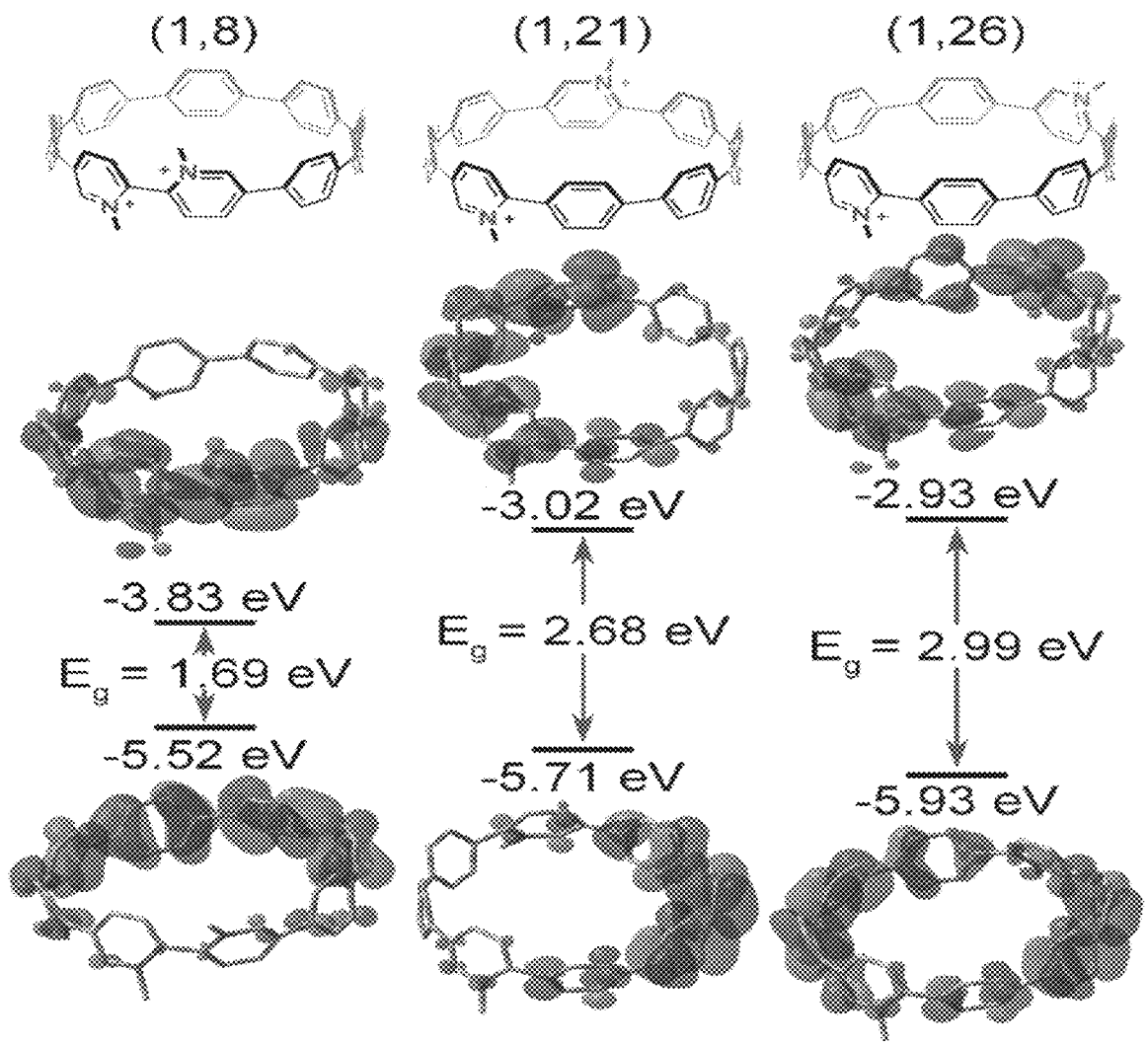
FIG. 9 is an image illustrating theoretical HOMO and LUMO energies for N,N-dimethyl-1,8-diaza[8]CPP (left), N,N-dimethyl-1,21-diaza[8]CPP (middle), and N,N-dimethyl-1,26-diaza[8]CPP (right).
Figure 36:
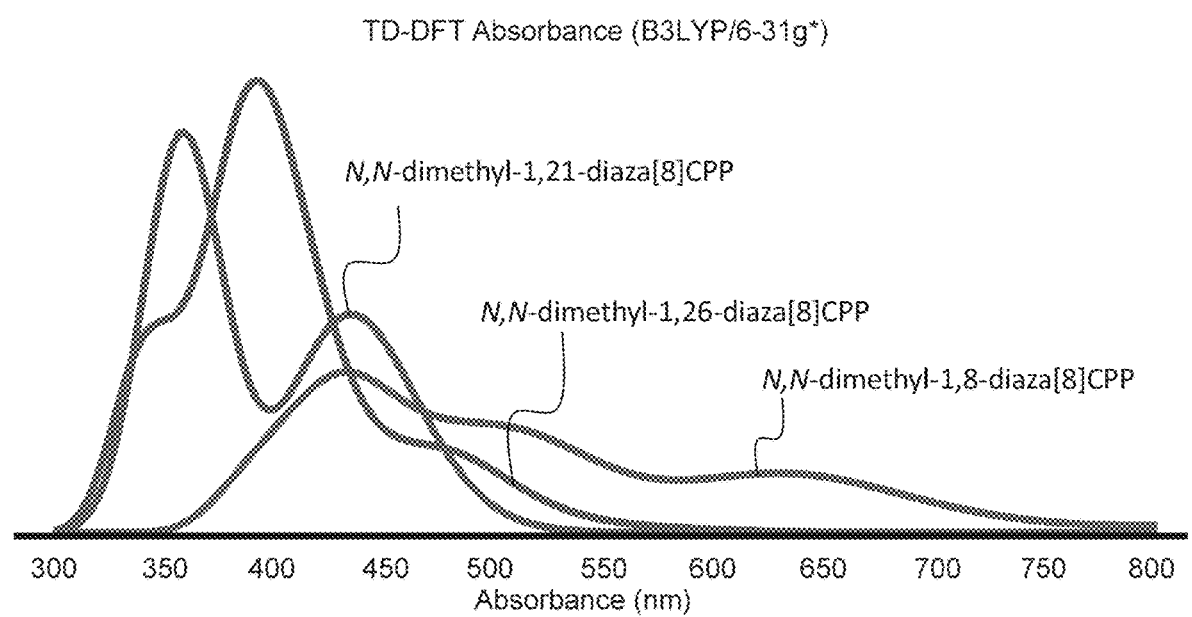
FIG. 36 is a TD-DFT absorbance plot predicting plots for representative functionalized nanohoop compounds N,N-Dimethyl-1,26-diaza[8]CPP, N,N-Dimethyl-1,21-diaza[8]CPP, and N,N-Dimethyl-1,8-diaza[8]CPP.

It is possible to develop functionalized nanohoop compounds that comprise chemical and electrochemical properties that lend to the ability to tune the LUMO and HOMO energies independently to thereby lower the HOMO-LUMO gap. The LUMO orbital energy levels achieved through alkylation of the aza[8]CPP can be tuned to fall within a desired range depending on the particular application. In some embodiments, a range of −3.0 eV to −4.0 eV can be desirable for use as an organic electronic material. In addition, by modifying the position of the electron-donating and electron-accepting ring units, it is also possible to drop both the LUMO and HOMO energies equally, which can be useful when designing organic devices with high open circuit voltages ($V_{oc}$). In some embodiments, positional modification was computationally studied by changing the relative pyridinium position in the N,N-dimethyl-x,y-diaza [8]CPP scaffold where x and y represent the relative position of each nitrogen in the hoop (FIG. 9). The three regioisomers shown, in addition to compound 5, highlight how modifying the relative position of the electron-accepting unit and/or the electron-donating unit can affect the properties of the nanohoop compounds. In an exemplary embodiment, the (1,8) isomer (FIG. 9, left) exhibited the lowest lying LUMO with orbital localization primarily on the electron poor pyridinium rings. The HOMO remains localized on the phenylene backbone maintaining an energy closer to neutral compound 5. A HOMO-LUMO energy gap of 1.7 eV is obtained, a value that coincides with a significant increase in the calculated absorption in the visible spectrum (FIG. 36). When the pyridinium rings are opposite one another in the (1,27) position (FIG. 9, right), there is a significant increase in orbital coefficients for both the HOMO and LUMO on both the pyridinium and phenylene sections resulting in a lowering of both while maintaining a HOMO-LUMO energy gap around 3.0 eV.

Conventional functionalized nanohoops retain high symmetry and have properties similar to a corresponding [n]CPP non-functionalized nanohoop compound. In contrast, the functionalized nanohoop compounds disclosed herein not only exhibit unique properties that are different from the parent [n]CPP compound (as well as conventional linear polymers), but they also provide the ability to tune HOMO and LUMO levels to a particular range that is desired for a particular application.

Figure 10:
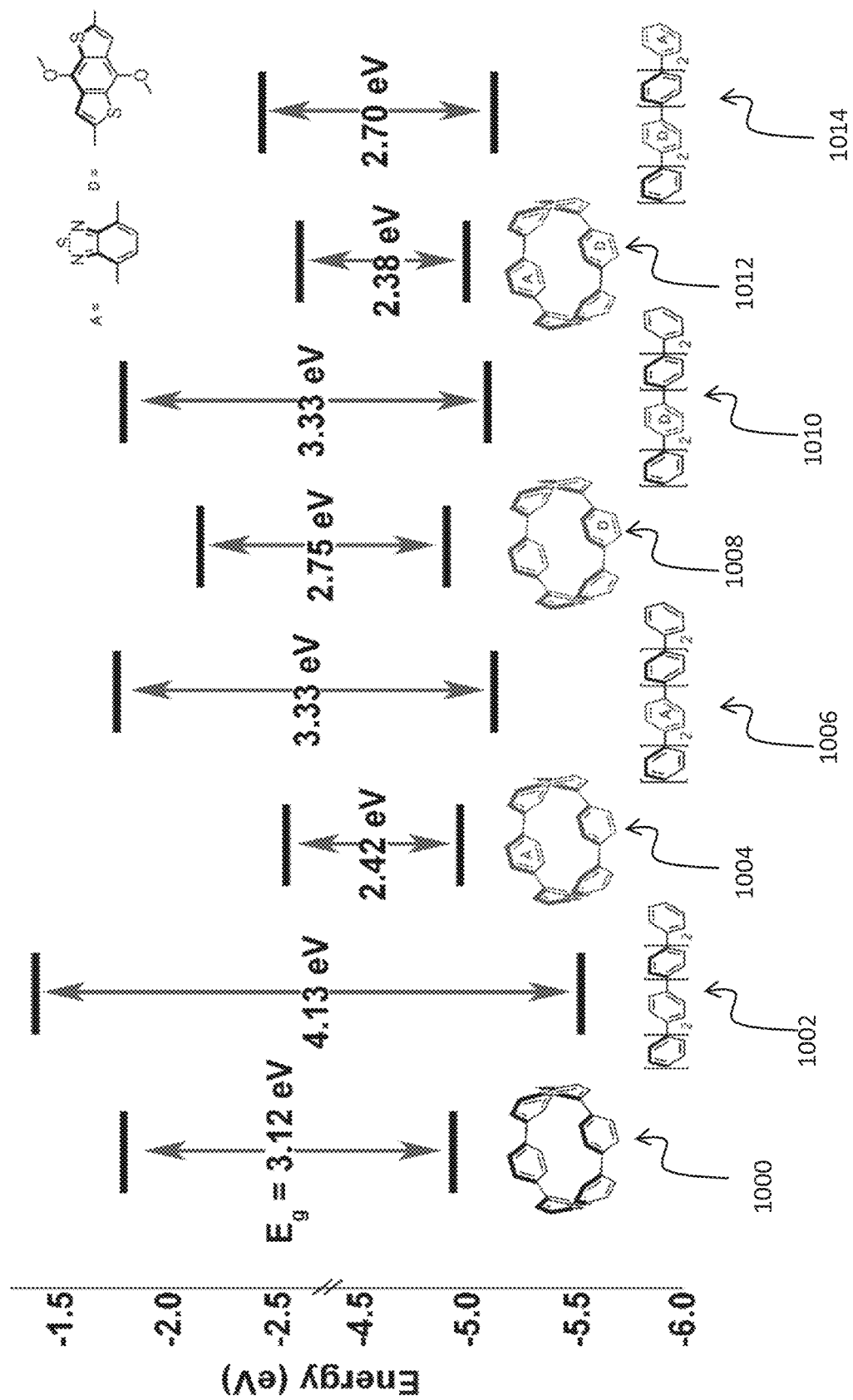
FIG. 10 is an image illustrating the effect on HOMO and LUMO energy levels by including acceptor and donator groups and/or units in nanohoops, as compared to linear compounds acceptor-containing nanohoops.

Solely by way of example, the effects of incorporating electron-donating units (and/or electron-donating groups) and electron-accepting units (and/or electron-accepting groups) can be evaluated computationally to facilitate selecting combinations that provide desired HOMO/LUMO effects. In one exemplary embodiment, the HOMO and LUMO energy levels of a functionalized nanohoop compound comprising both an electron-acceptor unit and an electron-donor unit was compared to corresponding nanohoop compounds comprising just an electron-acceptor unit or an electron-donor unit, as well as a non-functionalized nanohoop compound (FIG. 10). The nanohoop structures also were compared with linear compounds comprising mixed electron-donating and electron-accepting units, a single electron-accepting unit or a single electron-donating unit, and a non-functionalized linear compound.

The nanohoop compounds (including non-functionalized compound 1000, functionalized compounds 1004 and 1008 and mixed functionalized compound 1012, FIG. 10) exhibited a full eV lower HOMO-LUMO energy gap compared to the linear compounds (including linear compounds 1002, 1006, 1010, and 1014, FIG. 10). The LUMO energy is more significantly dropped in the cyclic framework than the linear framework. In the embodiments illustrated in FIG. 10, the cyclic system comprising the electron-deficient benzothiadiazole unit (compound 1004) is in conjugation with the electron-rich paraphenylene backbone resulting in a stronger donor-acceptor interaction that stabilized the LUMO energy more significantly than in the case of the linear paraphenylene (1006) which has significantly less donor characteristics. The incorporation of an electron-rich donor moiety, such as benzodithiophene (compound 1008) has a minimal effect on the cyclic framework HOMO suggesting the bent paraphyenylene framework is intrinsically a good donor. This leads to a more significant increase in HOMO energy in the linear framework (compound 1010) than the cyclic network (1008). The effect on HOMO and LUMO energy levels were even more pronounced when the benzodithiophene donor and benzodithiazole acceptor units were combined into the same hoop (compound 1012).

The functionalized nanohoop compounds disclosed herein are suitable for use in a variety of applications. In some embodiments, the functionalized nanohoop compounds can be used as photovoltaic materials. In some embodiments, the functionalized nanohoop compounds can be used in organic-based electronic applications, such as in lighting displays. In exemplary embodiments, the compounds disclosed herein can be used as organic semiconductors (e.g., organic field effect transistors), organic photovoltaic films, molecular wires, and organic light emitting diodes.

VI. Examples

Moisture and oxygen sensitive reactions were carried out under nitrogen atmosphere using standard Schlenk technique. All the glassware was thoroughly washed, dried in oven at 140° C. overnight and cooled under nitrogen atmosphere before use. All reagents were obtained commercially. Tetrahydrofuran (THF) and dichloromethane (DCM) were dried by filtration through alumina according to the method descried by Grubbs. Silica column chromatography was conducted with Zeochem Zeoprep n60 Eco 40-63 μm silica gel. Thin layer chromatography (TLC) was performed using Sorbent Technologies Silica Gel XHT TLC plates. Developed plates were visualized using UV light at wavelength of 254 and 365 nm.

Figure 34:
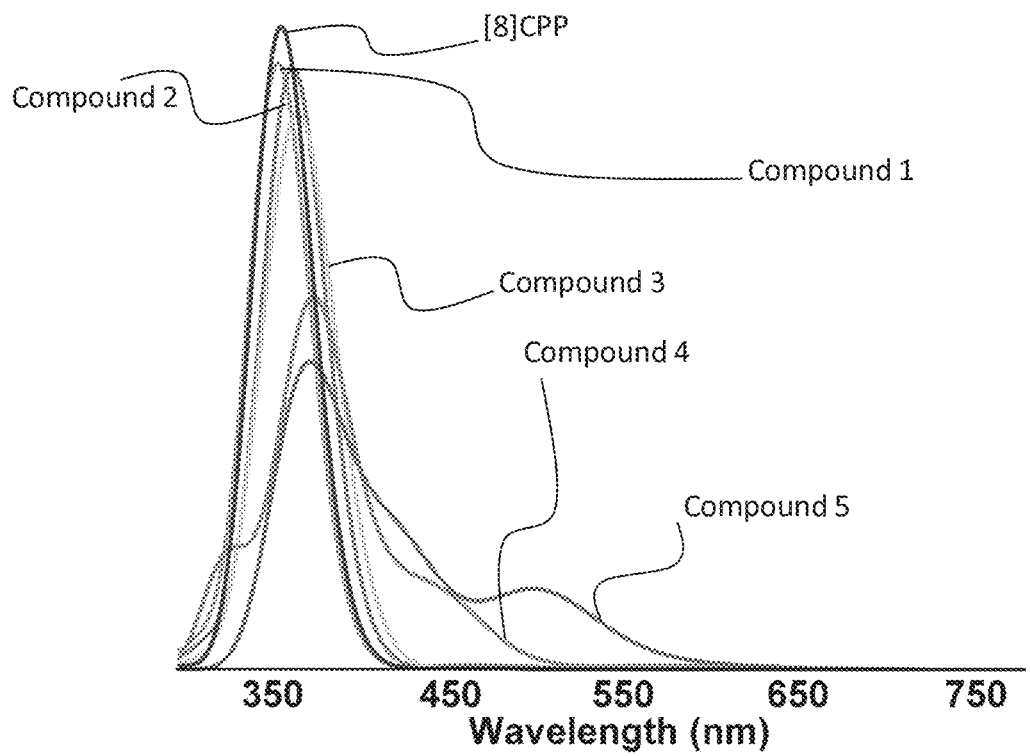
FIG. 34 is a TD-DFT absorbance plot for representative non-functionalized nanohoop compounds [8]CPP and 1-3 and representative functionalized nanohoop compounds 4 and 5.
Figure 35:
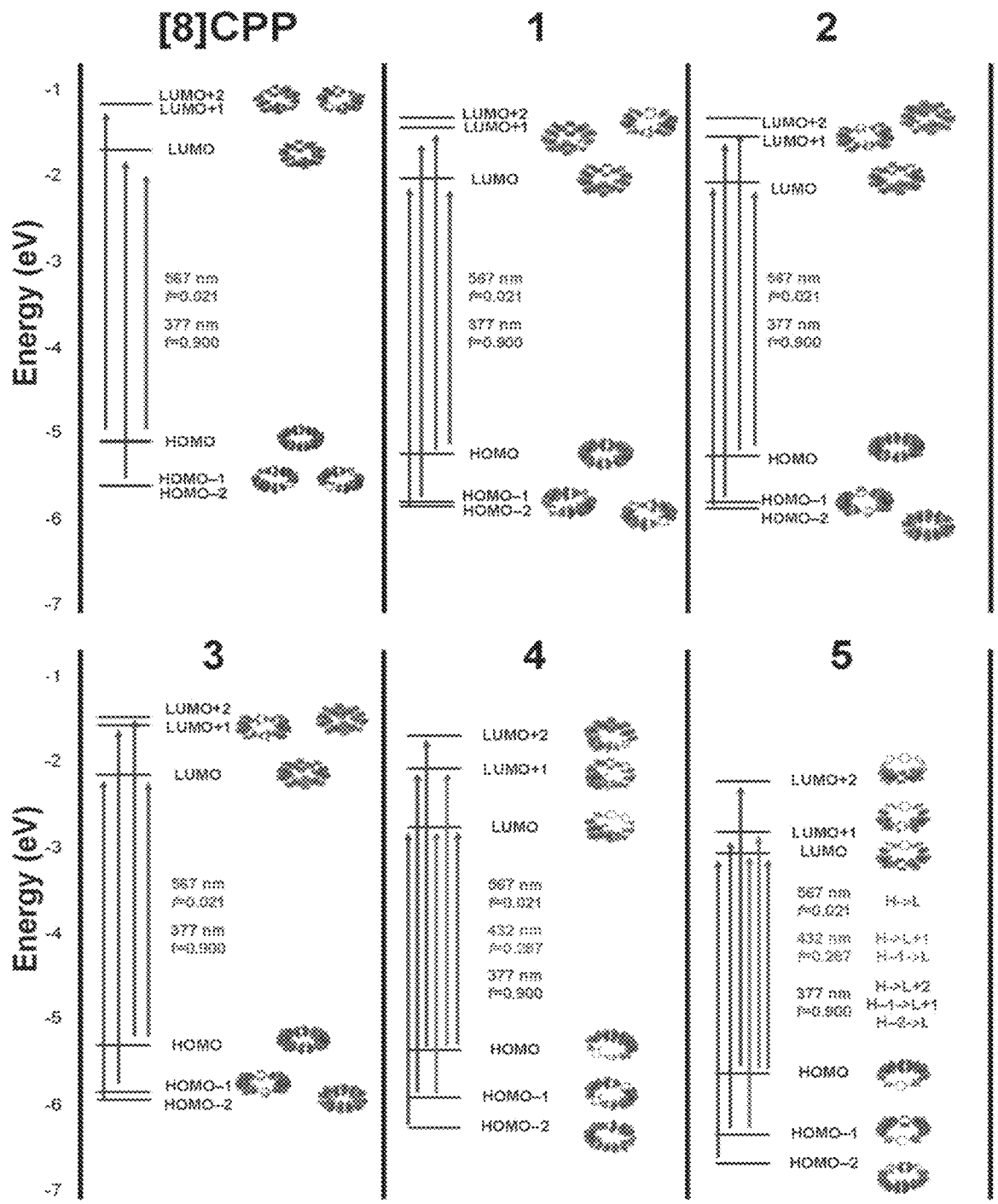
FIG. 35 is a TD-DFT plot illustrating the transitions and orbital densities for representative non-functionalized nanohoop compounds [8]CPP and 1-3 and representative functionalized nanohoop compounds 4 and 5.

The effects of nitrogen incorporation on the electronic structure and properties of [8]CPP was explored in detail for the target molecules 1-5 using density function theory (DFT) calculations at the B3LYP/6-31g* level of theory. Ground state geometry optimizations were first performed in the gas phase. Although geometries and orbital densities from these calculations have been shown to correlate well with experimental values the addition of charged species gave inaccurate values for orbital energies. In the gas phase charged species have high electrostatic interactions which cause the calculated orbital energies to be in accurate. In some embodiments, this discrepancy can be overcome by minimizing each geometry in the gas phase while omitting the counter ion for charged species. A solvated (acetonitrile) single point energy calculation is then performed using the conductor-like polarization continuum model (CPCM). This gave a stronger correlation between computed frontier orbitals and experimental reduction and oxidation values for both charged and neutral aromatic species. Time-dependent density functional theory (TD-DFT) was used to predict and assign absorbances again using CPCM with acetonitrile as the solvent. The red-shifted values observed from the experimental to the predicted spectra is commonly observed. The peak shape and relative intensity matched allowing transition assignment. Some exemplary TD-DFT transitions and orbital densities are provided by FIG. 35. Also, some exemplary TD-DFT absorbance spectra are illustrated in FIGS. 34 and 36.

$^1$H NMR spectra were recorded at 400 MHz or 500 MHz on a Varian VNMR spectrometer or at 600 MHz on a Bruker Avance-III-HD NMR spectrometer. $^{13}$C NMR spectra were recorded at 100 MHz or 125 MHz on a Varian VNMR Spectrometer or at 150 MHz on a Bruker Avance-III-HD NMR spectrometer. Deuterated chloroform (CDCl$_3$) was used as the NMR solvent for compounds 1-4 and 6-12d while deuterated dimethyl sulfoxide (DMSO d6) was used for compound 5 due to poor solubility. All the compounds and all spectra were referenced to tetramethylsilane (TMS).

Absorbance spectra for compounds 1-6 were obtained using dichloromethane as the solvent in a 1 cm quartz cuvette on an Agilent Cary 60 UV-Vis spectrophotometer. Emission spectra for compounds 1-6 were collected using dichloromethane as the solvent in a 1 cm quartz cuvette using a Horiba Jobin Yvon FluoroMax-4 spectrophotometer. Extinction coefficient information for certain compounds disclosed herein are provided by FIGS. 29A, 29B, 30A, 30B, 31A, 31B, 32A, 32B, and 33A-33C.

THF, dichloromethane and DMF were dried by filtration through alumina according. Silica column chromatography was conducted with Zeochem Zeoprep 60 Eco 40-63 μm silica gel. Thin Layer Chromatography (TLC) was performed using Sorbent Technologies Silica Gel XHT TLC plates. Developed plates were visualized using UV light at wavelengths of 254 and 265 nm. All glassware was oven or flame dried and cooled under an inert atmosphere of nitrogen unless otherwise noted.

Cyclic voltammetry was conducted utilizing a platinum working electrode, platinum counter electrode, and a silver wire pseudoreference that was separated from the solution via a glass frit. Experiments were performed using a custom designed potentiostat at a scan rate of 50 mV/s. Analyte solutions were freeze-pump-thaw degassed three times and all experiments were conducted under air-free conditions. Analyte solutions were prepared using 0.1 M tetrabutylammonium tetrafluoroborate in THF, with analyte concentrations 1-5 mM. The Ag psuedoreference was calibrated versus the ferrocene/ferrocinium redox couple following the CV of each compound.

Diffraction intensities were collected at 173 (1) and 200(2) (5) on a Bruker Apex2 CCD diffractometer using an Incoatec 1 μS micro-focus source with CuKα radiation, λ=1.54178 Å. Space groups were determined based on systematic absences. Absorption corrections were applied by SADABS$^2$. Structures were solved by direct methods and Fourier techniques and refined on F$^2$ using full matrix least-squares procedures. All non-H atoms were refined with anisotropic thermal parameters. H atoms in both structures were refined in calculated positions in a rigid group model. Crystals of compound 1 were very small and even with using a strong Incoatec Cu 1 μS micro-focus source provided non-zero reflections only up to 2θ$_{max}$=106.6°. Only such reflections were involved in the final refinement. The molecule of compound 1 has C$_2$ symmetry. The structure of compound 1 has additionally solvent molecule Me$_2$SO located inside the main molecule. It was determined that the crystal structure of 5 has six solvent CHCl$_3$ molecules. One of them is located inside the cation and others fill out empty spaces in the crystal packing. Four of these molecules are highly disordered and were treated by SQUEEZE$^3$. The correction of the X-ray data by SQUEEZE is 938 electron/cell: the required value is 928 electron/cell for 16 solvent molecules CHCl$_3$ in the full unit cell. All calculations were performed by the SHELXL-2013 packages.

Compounds 6, 7a, 7b, 8a, 8b, 9a, 10a, 11a, 12a, and [8]CPP were prepared in accordance with the method and steps illustrated in Scheme 2.

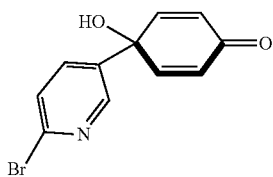

7c nBuLi (2.50 M in hexanes, 45.0 mL, 112 mmol, 1.15 eq) was diluted into a flask of THF (550 mL) and cooled to −78° C. This solution was allowed to cool for another 30 minutes with stirring.[3] To this solution was added dropwise a solution of 2,5-dibromopyridine (25.0 g, 107 mmol, 1.10 eq) in THF (100 mL). The reaction was stirred for 30 minutes at −78° C. to give the lithiated species as a deep red solution.

In a separate flask, 4,4-dimethoxycyclohexa-2,5-dienone 6 (15.0 g, 97.4 mmol, 1.00 eq) was dissolved in THF (200 mL) and cooled to −78° C. To this was added the solution of lithiated 2-bromo-pyridine dropwise by cannula. The reaction was stirred for 3 hours at −78° C. after completion of the transfer. After 3 hours, the reaction was quenched with MeOH and allowed to warm to room temperature. The mixture was extracted with ether. After separation of the phases, the aqueous layer was washed with ether (3×200 mL). The combined organic layers were washed with brine and dried over sodium sulfate before being filtered and concentrated down to a yellowish-brown semi-solid. The solid was carried on crude.

Figure 11A:
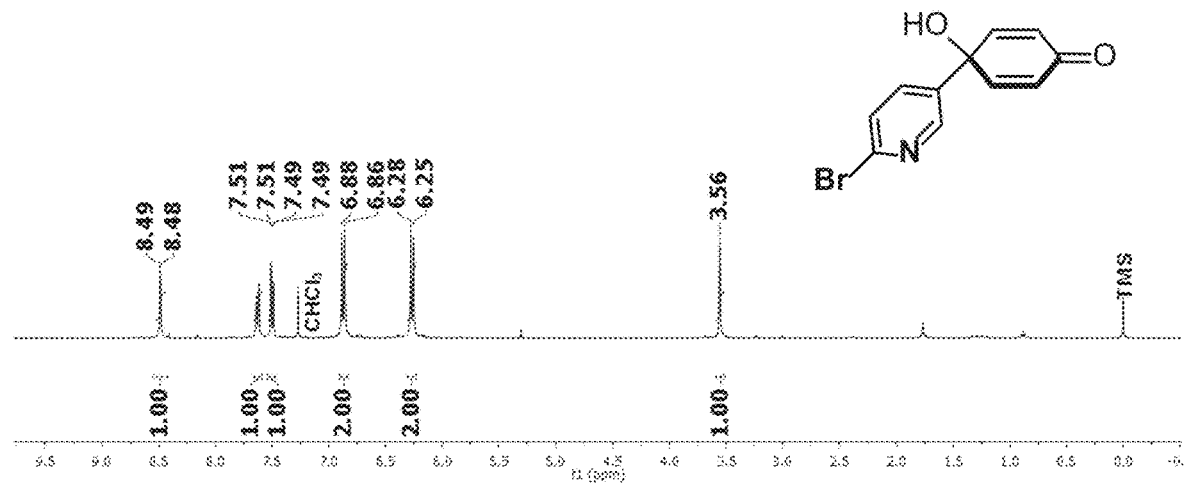
FIGS. 11A and 11B are $^1$H-NMR (FIG. 11A) and $^{13}$C-NMR (FIG. 11B) spectra of a compound used to make the nanohoops described herein.
Figure 11B:
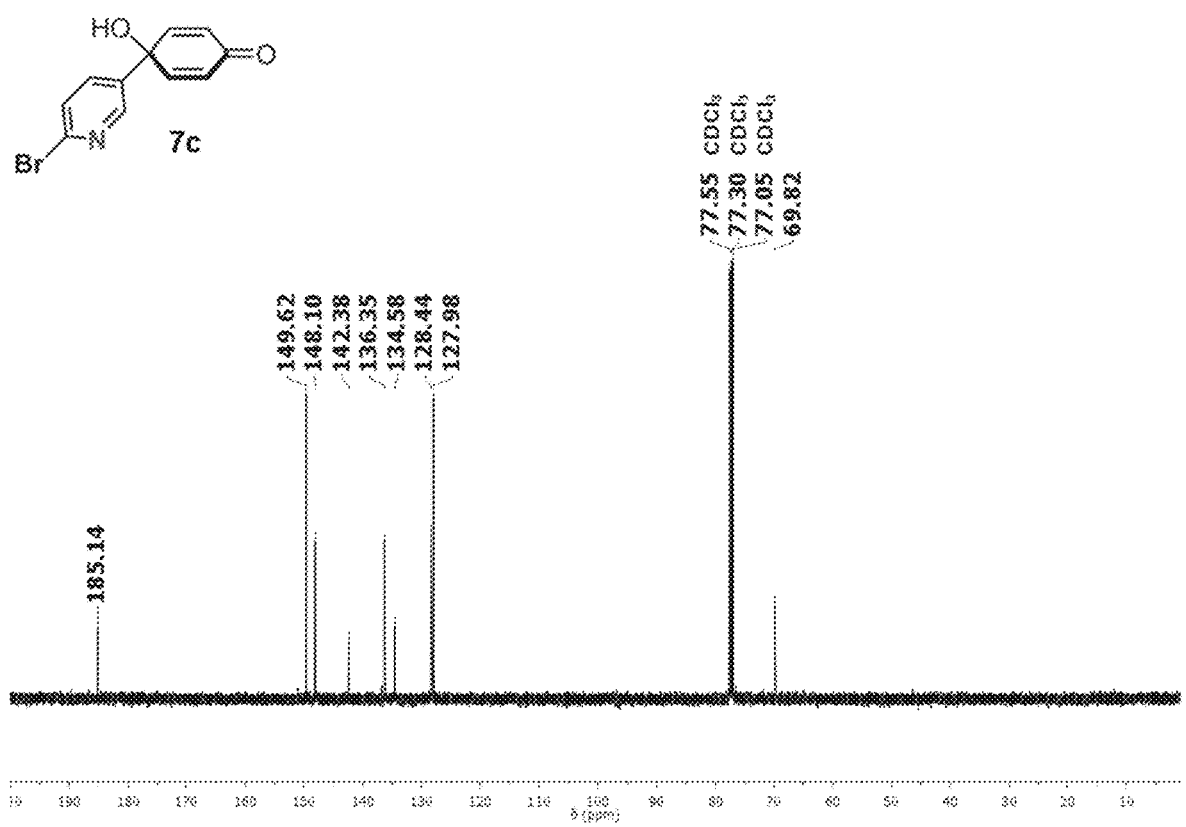

The solid from above was dissolved in acetone (250 mL). An equal volume of 10% AcOH (250 mL) was added. The solution was stirred at room temperature for 4 hours. The acetone was removed by rotary evaporation. The remaining aqueous layer was extracted with dichloromethane (3×100 mL). The combined organic layers were washed with brine and dried over sodium sulfate before being concentrated down to a brown solid. The solid was then purified by recrystallization with absolute ethanol to yield a pale tan solid (10.7 g, 42% yield). mp 145-147° C. $^1$H NMR (400 MHz, CDCl$_3$): δ 6.30 (d, J=10 Hz, 2H), 6.85 (d, J=10 Hz, 2H), 7.50 (d, J=8.4 Hz, 1H), 7.61 (dd, J=8.4 Hz, 2.8 Hz, 1H), 8.50 (d, J=2.8 Hz, 1H); $^{13}$C NMR (125 MHz, CDCl$_3$): δ 185.14, 149.62, 148.10, 142.38, 136.35, 134.58, 128.44, 127.98, 69.82; HRMS (Q-TOF, ES+) (m/z): [M+H]$^+$ calculated for C$_{11}$H$_8$BrNO$_2$, 265.9817. found: 265.9722. IR (neat): 3396, 3097, 3067, 3045, 2964, 1662, 1616, 1441, 1388, 1237, 1175, 1093, 1016, 921, 861 cm$^{-1}$. See FIGS. 11A and 11B.

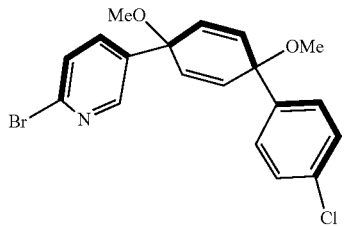

8c

To a solution of 4-bromo-1-chlorobenzene (14.9 g, 77.8 mmol, 2.40 eq) in THF (225 mL) at −78° C. Was added nBuLi (2.5 M in hexanes, 31.0 mL, 77.5 mmol, 2.00 eq). The solution was stirred for 30 minutes at −78° C. and generated a cloudy white suspension.

Figure 12A:
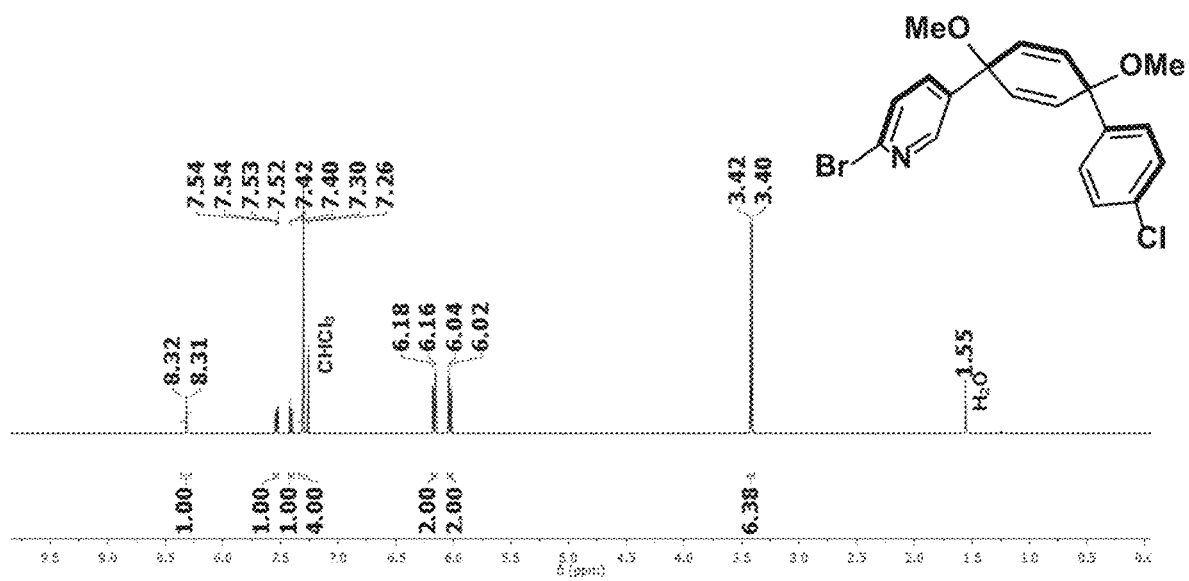
FIGS. 12A and 12B are $^1$H-NMR (FIG. 12A) and $^{13}$C-NMR (FIG. 12B) spectra of a compound used to make the nanohoops described herein.
Figure 12B:
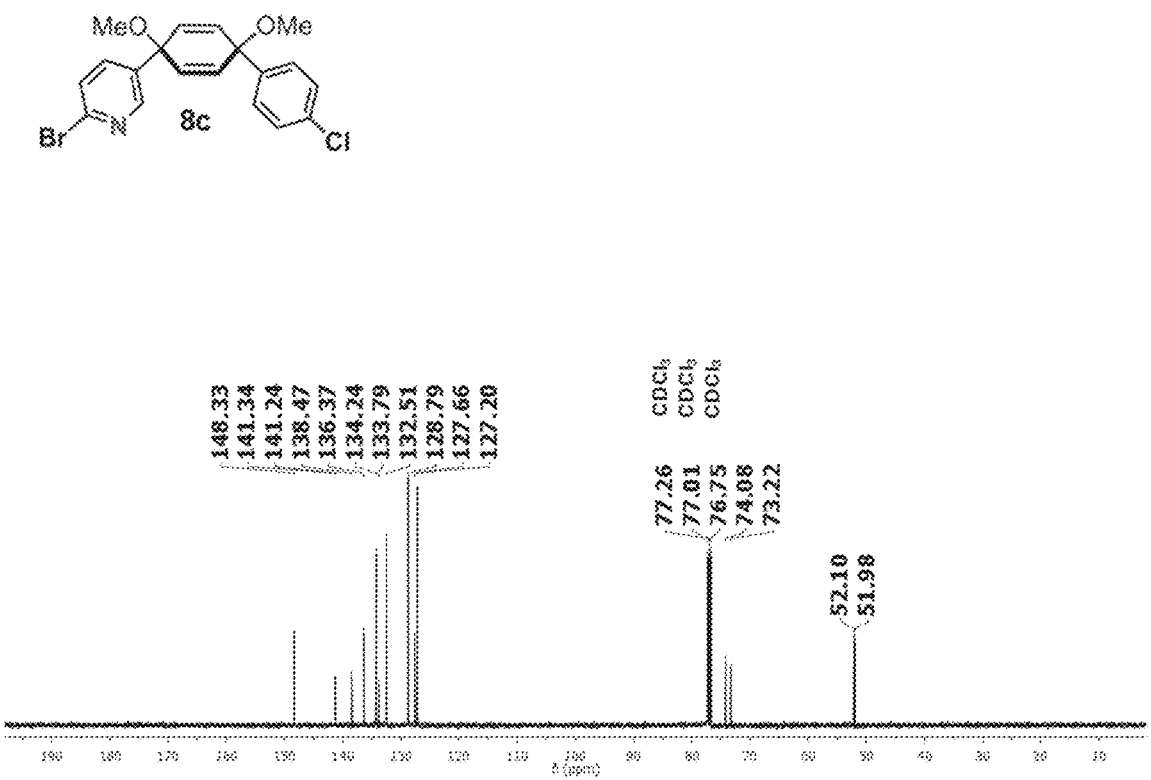

In a separate flask, NaH (1.60 g, 60% suspension in mineral oil, 40.0 mmol, 1.20 eq) was suspended in THF (150 mL) and cooled to −78° C. Pyridyl quinol 7c (9.10 g, 34.3 mmol, 1.00 eq) was dissolved in THF (50 mL) and added drop wise via cannula to the NaH suspension. The mixture was stirred for 2 hours at −78° C. At this time, lithiated chlorobenzene was transferred dropwise via cannula into the NaH/Quinol mixture. The reaction was stirred for 3 hours at −78° C., during which the reaction turned a yellow-brown color. Next, MeI (10.6 mL, 170 mmol, 5.00 eq) and DMF (75 mL) were added and the reaction was allowed to warm to room temperature and stir for 18 hours. Water (100 mL) and ether (250 mL) were added and the phases allowed to separate. The aqueous layer was washed with ether (3×250 mL). The combined organic phases were washed with brine before being dried over sodium sulfate. Solvent was removed under reduced pressure to give a brown solid. The crude material was purified by washing with hexanes and recrystallization from hot ethanol (7.00 g, 51%) mp 107-109° C. $^1$H NMR (500 MHz, CDCl$_3$): δ 3.41 (s, 3H), 3.42 (s, 3H), 6.03 (d, J=8 Hz, 2H), 6.17 (d, J=8 Hz, 2H), 7.30 (bs, 4H), 7.41 (d, J=8.4 Hz, 1H), 7.53 (dd, J=8.4, 2.6 Hz, 1H), 8.31 (d, J=2.6 Hz, 1H); $^{13}$C NMR (125 MHz, CDCl$_3$): δ 148.63, 141.64, 141.54, 138.77, 136.67, 134.53, 134.08, 132.80, 129.08, 127.95, 127.50, 74.38, 73.52, 52.40, 52.28. HRMS (Q-TOF, ES+) (m/z): [M+H]$^+$ calculated for C$_{19}$H$_{17}$BrClNO$_2$, 406.0208. found 406.0208. IR (neat): 2992, 2924, 2854, 2820, 1572, 1486, 1449, 1398, 1361, 1171, 1070, 1015, 947, 832, 732 cm$^{-1}$. See FIGS. 12A and 12B.

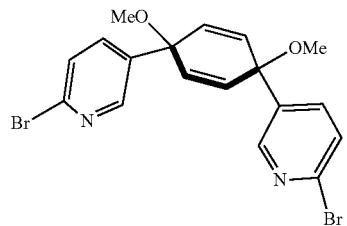

8d nBuLi (2.5 M in hexanes, 1.79 mL, 4.48 mmol, 2.40 eq) was diluted in THF (25 mL) at −78° C. This solution was allowed to cool for another 30 minutes with stirring.[3] To this was added via cannula a solution of 2,5-dibromopyridine (1.10 g, 4.48 mmol, 2.40 eq) in THF (5 mL). The deep red solution was stirred for 30 minutes at −78° C.

Figure 13A:
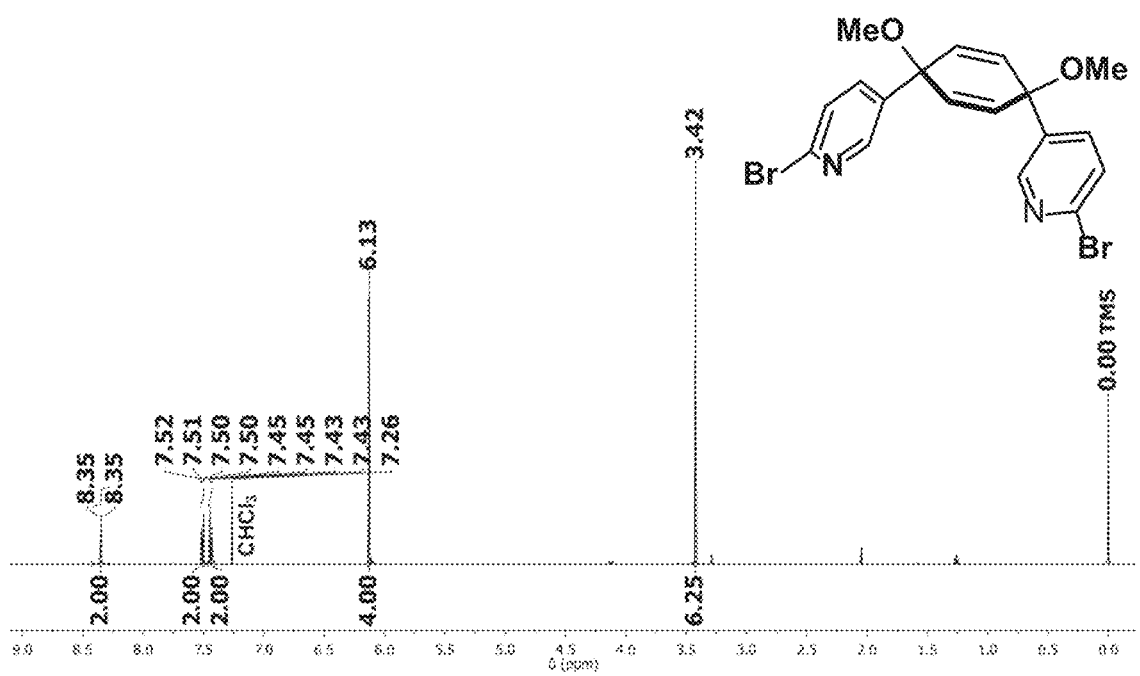
FIGS. 13A and 13B are $^1$H-NMR (FIG. 13A) and $^{13}$C-NMR (FIG. 13B) spectra of a compound used to make the nanohoops described herein.
Figure 13B:
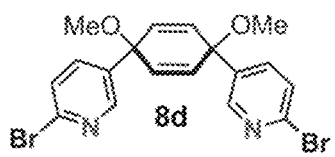
Figure 13B:
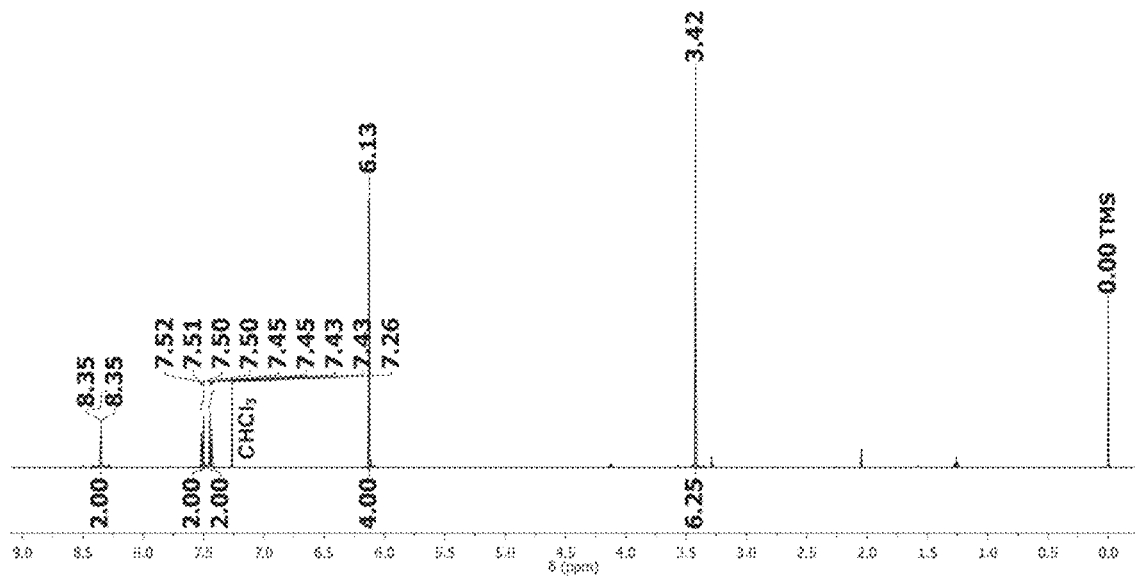

In a separate flask, NaH (100 g, 2.26 mmol, 1.20 eq) was suspended in THF (7 mL) and cooled to −78° C. Quinol 7c (0.500 g, 1.87 mmol, 1.00 eq) was dissolved in THF (5 mL), and transferred into the NaH solution by cannula. After stirring at −78° C. for 2 hours, the lithiated 2-bromopyridine was transferred by cannula to this solution. The reaction was stirred for 3 hours at −78° C. After this time, methyl iodide (0.700 mL, 11.2 mmol, 6.00 eq) and DMF (15 mL) were added. The flask was raised out of the bath and allowed to warm to room temperature over 20 hours. Water (50 mL) and ether (50 mL) were added and the phases allowed to separate. The aqueous layer was washed with ether (3×100 mL). The combined organic phases were washed with brine before being dried over sodium sulfate. Solvent was removed under reduced pressure to give a brown solid. The crude material was re-crystallized with hot ethanol yielding a light tan solid (0.350 g, 43%) mp 197-198° C. $^1$H NMR (400 MHz, CDCl$_3$): δ 3.42 (s, 6H), 6.13 (s, 4H), 7.44 (d, J=8.2 Hz, 2H), 7.51 (dd, J=8.2 Hz, 2.2 Hz, 2H), 8.35 (d, J=2.2 Hz, 2H); $^{13}$C NMR (125 MHz, CDCl$_3$): δ 148.47, 141.84, 138.35, 136.45, 133.73, 128.17, 73.29, 52.41. HRMS (Q-TOF, ES+) (m/z): [M+H]$^+$ calculated for C$_{18}$H$_{16}$Br$_2$N$_2$O$_2$, 450.9657. found, 450.9650. IR (neat): 3063, 3008, 2994, 2938, 2896, 2822, 1574, 1556, 1446, 1403, 1359, 1289, 1276, 1233, 1180, 1080, 1054, 1025, 1008, 952, 901, 833 cm$^{-1}$. See FIGS. 13A and 13B and FIG. 27 (with reference to FIG. 27, "Br"=bromine; "O"=oxygen; "N"=nitrogen; "C"=carbon).

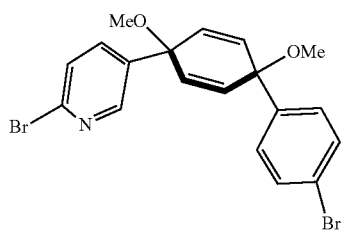

8e

To a solution of 1,4-dibromobenzene (10.5 g, 44.5 mmol, 2.40 eq) in THF (225 mL) at −78° C. was added nBuLi (2.5 M in hexanes, 19 mL, 46.3 mmol, 2.50 eq). The solution was stirred for 30 minutes at −78° C. and generated a cloudy white suspension.

Figure 14A:
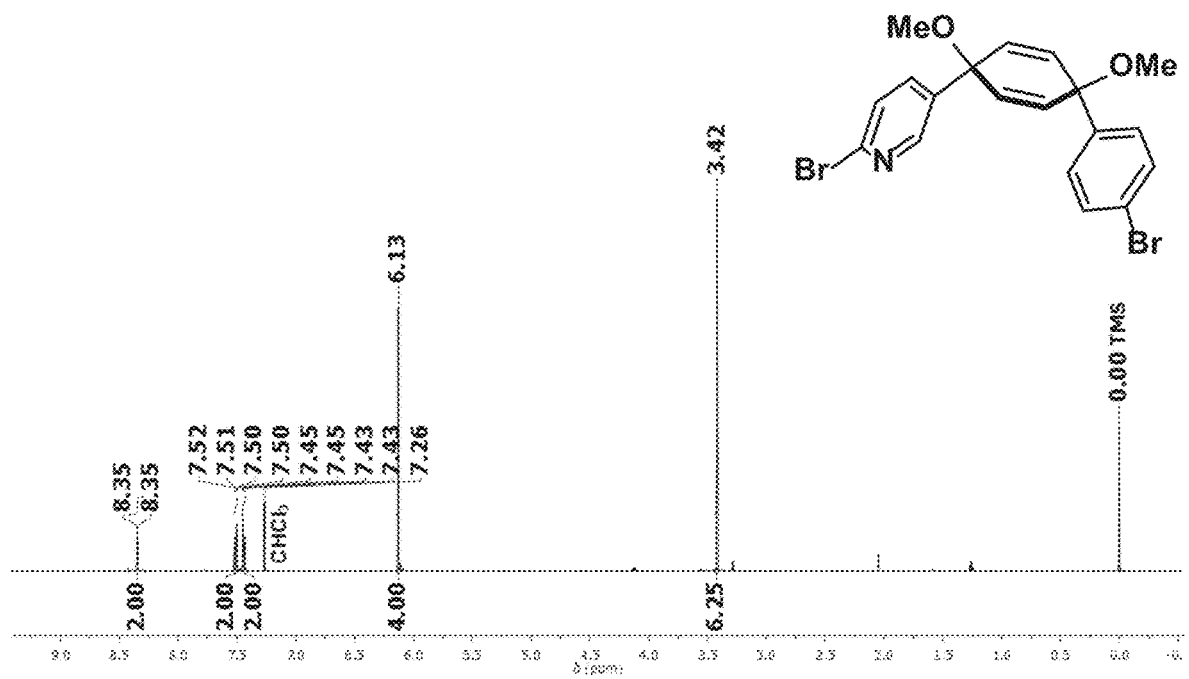
FIGS. 14A and 14B are $^1$H-NMR (FIG. 14A) and $^{13}$C-NMR (FIG. 14B) spectra of a compound used to make the nanohoops described herein.
Figure 14B:
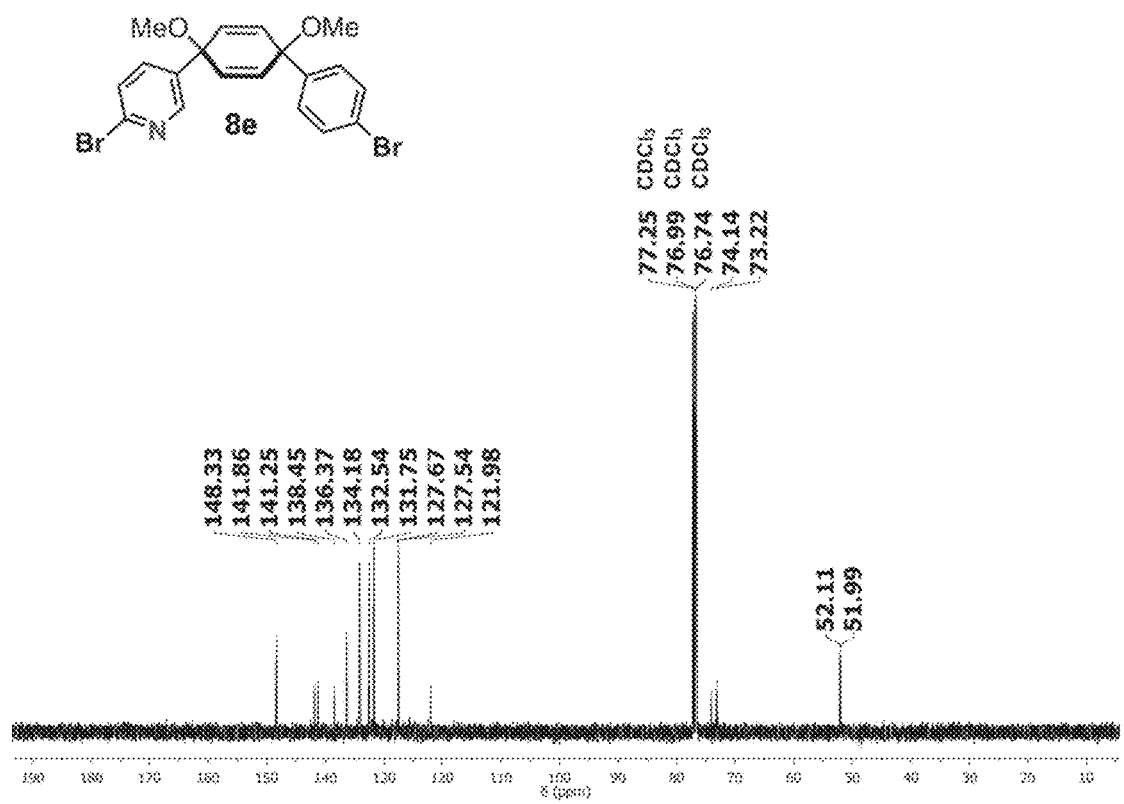

In a separate flask, NaH (0.890 g, 60% suspension in mineral oil, 22.3 mmol, 1.20 eq) was suspended in THF (80 mL) and cooled to −78° C. Pyridyl quinol 7c (5.00 g, 18.5 mmol, 1.00 eq) was dissolved in THF (15 mL) and added drop wise via cannula to the NaH suspension. The mixture was stirred for 2 hours at −78° C. At this time, lithiated bromobenzene was transferred dropwise via cannula into the NaH/Ketone mixture. The reaction was stirred for 3 hours at −78° C., during which the reaction turned a yellow-brown color. Next, MeI (5.76 mL, 92.5 mmol, 5.00 eq) and DMF (45 mL) were added and the reaction was allowed to warm to room temperature and stir for 18 hours. Water (100 mL) and ether (250 mL) were added and the phases allowed to separate. The aqueous layer was washed with ether (3×100 mL). The combined organic phases were washed with brine before being dried over sodium sulfate. Solvent was removed under reduced pressure to give a brown solid. The crude material was purified by column chromatography (silica gel, 30% Ethyl Acetate in Hexanes eluent) to recover a pale yellow solid which was then recrystallized from hot ethanol to give a light tan solid (4.20 g, 50%) mp 124-125° C. $^1$H NMR (500 MHz, CDCl$_3$): δ 3.40 (s, 3H), 3.42 (s, 3H), 6.03 (d, J=10 Hz, 2H), 6.16 (d, J=10 Hz, 2H), 7.24 (d, J=8.8 Hz, 2H), 7.41 (d, J=9.3 Hz, 1H), 7.46 (d, J=8.8 Hz, 2H) 7.54 (dd, J=9.3, 3 Hz, 1H), 8.31 (d, J=3 Hz, 1H). $^{13}$C NMR (125 MHz, CDCl$_3$): δ 148.75, 141.75, 141.67, 138.89, 136.79, 134.65, 134.22, 132.92, 129.21, 128.08, 127.62, 74.51, 73.65, 52.52, 52.40. HRMS (Q-TOF, ES+) (m/z): [M+H]$^+$ calculated for C$_{19}$H$_{17}$Br$_2$NO$_2$, 449.9704 found 449.9720. IR: 2973, 2939, 2894, 2818, 1570, 1554, 1482, 1447, 1393, 1360, 1288, 1175, 1065, 1029, 1018, 1004, 992, 946, 836 cm$^{-1}$. See FIGS. 14A and 14B.

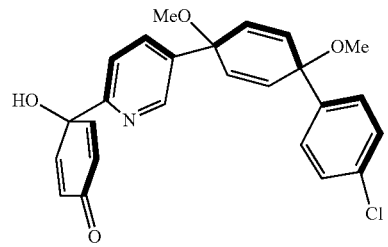

Figure 15A:
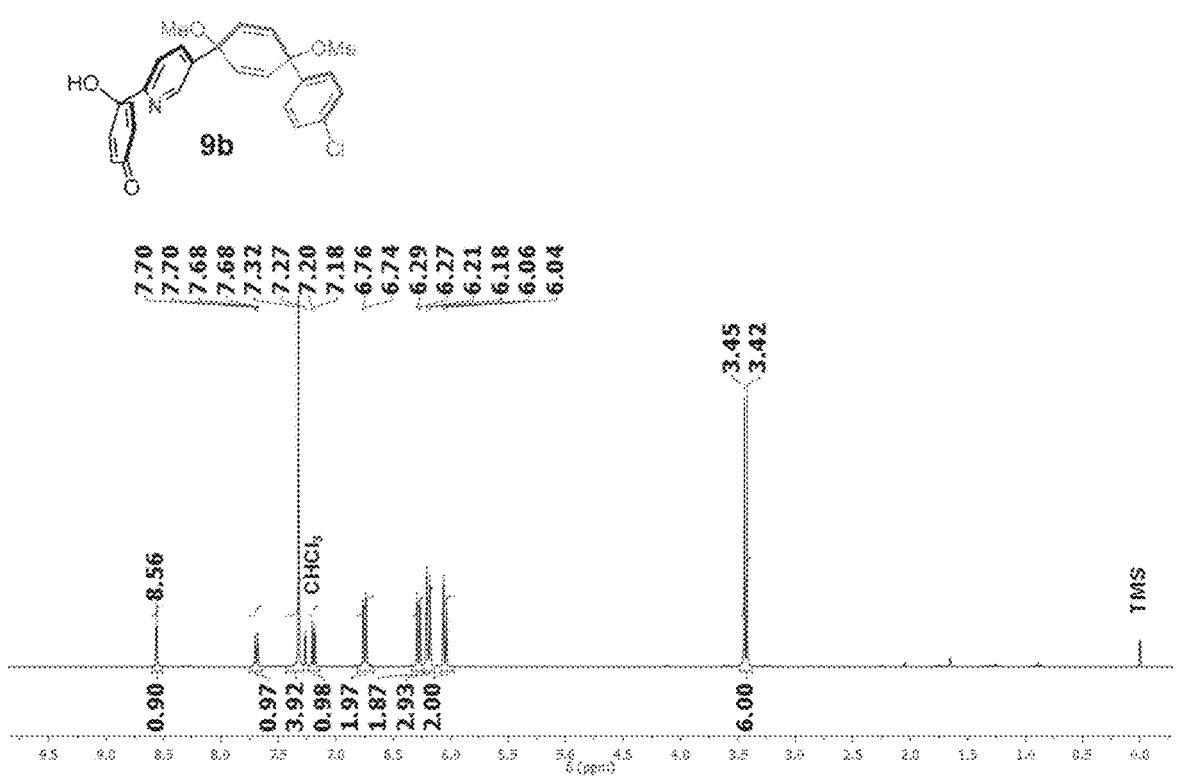
FIGS. 15A and 15B are $^1$H-NMR (FIG. 15A) and $^{13}$C-NMR (FIG. 15B) spectra of a nanohoop compound intermediate.
Figure 15B:
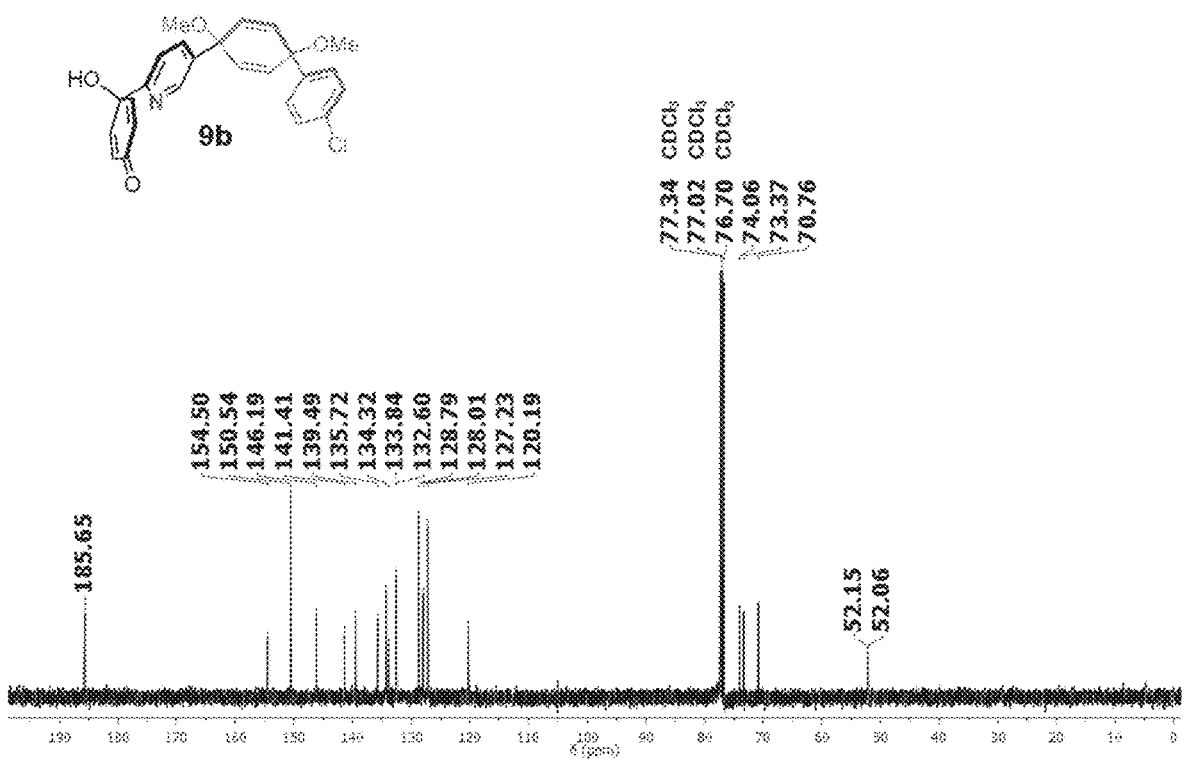

9b 8e (5.80 g, 14.3 mmol, 1.00 eq) was added to a dry flask and dissolved in dry THF (200 mL). The solution was cooled to −78° C. nBuLi (2.5 M in hexanes, 6.30 mL, 15.7 mmol, 1.10 eq) was added dropwise over 5 minutes resulting in a deep reddish-purple solution. After stirring at −78° C. for 10 minutes, 4,4-dimethoxycyclohexa-2,5-dienone 6 (2.80 g, 18.5 mmol, 1.30 eq) was added neat. The solution then turned yellow-orange. The reaction was stirred for 1 hour before being quenched with H$_2$O. The aqueous layer was then washed with diethyl ether (3×100 mL). The combined organic layers were washed with brine and dried over Na$_2$SO$_4$, and concentrated down to a yellow oil. The oil was dissolved in acetone (50 mL) and 5% AcOH/H$_2$O was added (50 mL). The solution was stirred at room temperature for 2 hours. The solution was neutralized with sodium bicarbonate and extracted with diethyl ether (3×100 mL). The combined organic layers were washed with brine and dried over Na$_2$SO$_4$. The solution was concentrated under reduced pressure to yield a yellow solid. The solid was purified by column chromatography to give a light tan solid (silica gel, 30% EtOAc/DCM eluent), (4.00 g, 65%). mp 156-159° C. $^1$H NMR (400 MHz, CDCl$_3$): δ 3.42 (s, 3H), 3.45 (s, 3H), 6.05 (d, J=11 Hz, 2H), 6.20 (d, J=11 Hz, 2H), 6.28 (d, J=10.2 Hz, 2H), 6.75 (d, J=10.2 Hz, 2H), 7.20 (d, J=8.4 Hz, 1H), 7.32 (s, 4H), 7.69 (dd, J=8.4, 1.6 Hz, 1H), 8.56 (d, J=1.6 Hz, 1H). $^{13}$C NMR (100 MHz, CDCl$_3$): δ 185.86, 154.71, 150.75, 146.40, 141.62, 139.70, 135.93, 134.53, 134.05 132.81, 129.00, 128.20, 127.40, 120.40, 74.27, 73.58, 70.97, 52.36, 52.27. HRMS (Q-TOF, ES+) (m/z) calculated for C$_{25}$H$_{22}$ClNO$_4$: 436.1316. found, 436.1303. IR: 2938, 2902, 2820, 2106, 1667, 1627, 1481, 1401, 1075, 954, 857, 726 cm$^{-1}$. See FIGS. 15A and 15B.

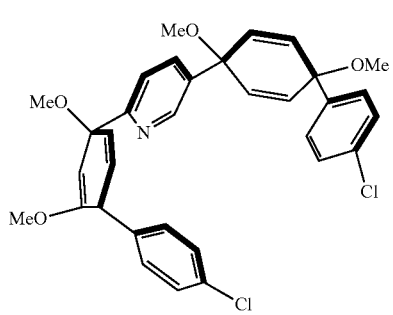

10b

Ketone 9b (1.00 g, 2.29 mmol, 1.00 eq) and 5-bromo-2-chloropyridine (0.960 g, 5.00 mmol, 2.20 eq) were added to a dry round bottom flask and dissolved in dry THF (75 mL). The solution was cooled to −78° C. for 1 hour. To this solution was added NaH (0.100 g, 2.80 mmol, 1.20 eq) as a solid. The reaction was stirred for 2 hours. After 2 hours, nBuLi (2.20 mL, 5.60 mmol, 2.40 eq) was added drop-wise.

Figure 16A:
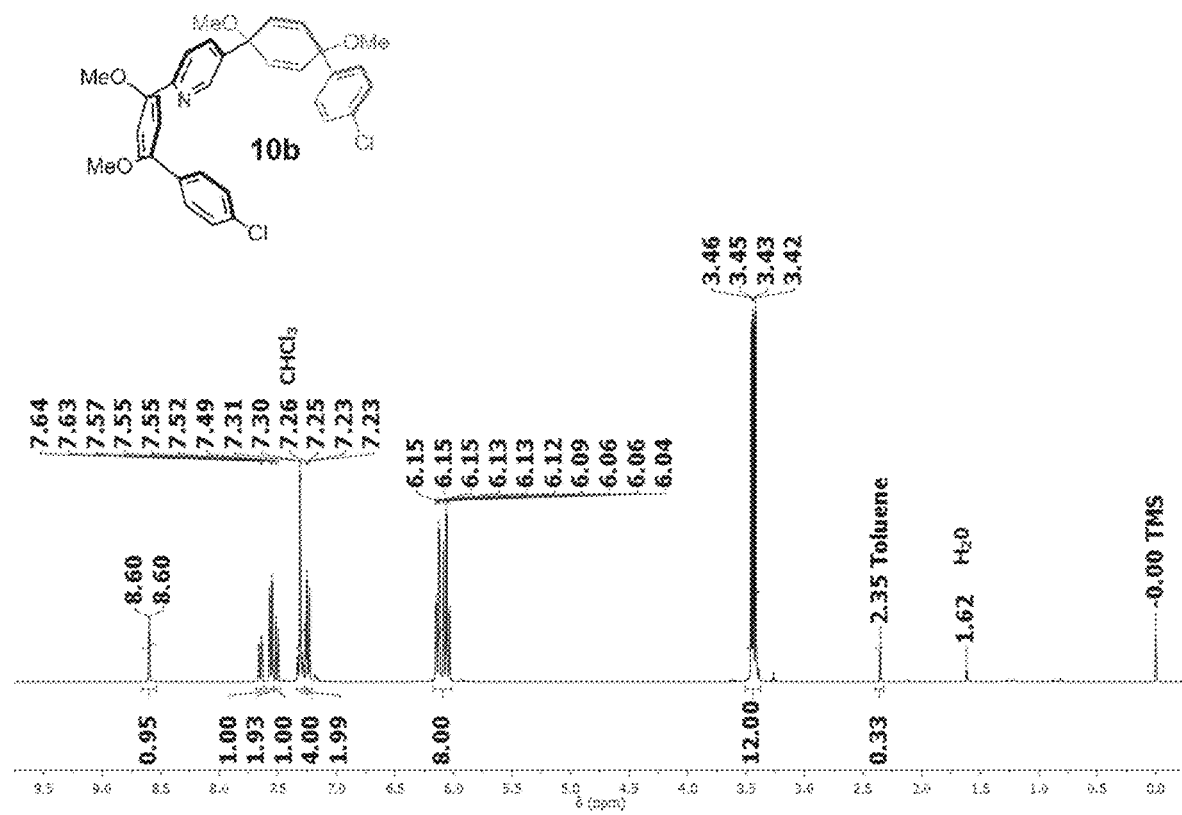
FIGS. 16A and 16B are $^1$H-NMR (FIG. 16A) and $^{13}$C-NMR (FIG. 16B) spectra of a nanohoop compound intermediate.
Figure 16B:
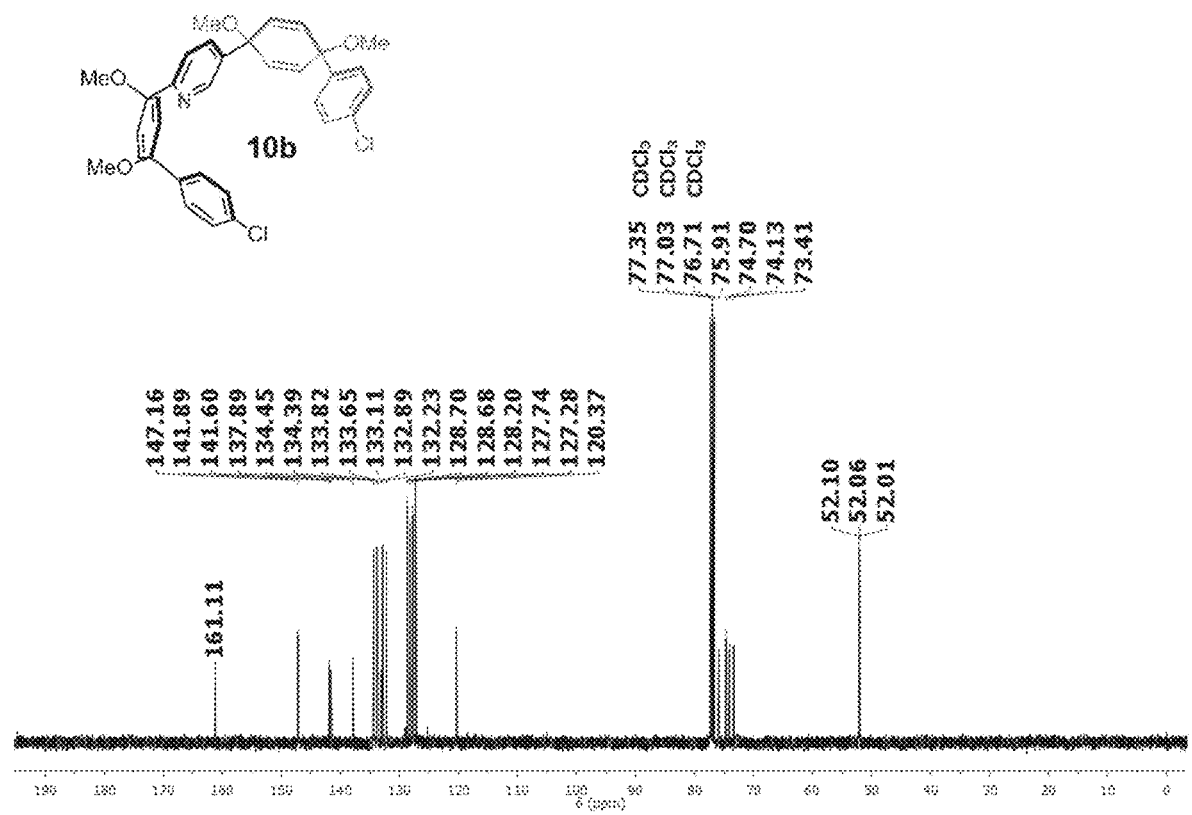

The reaction was stirred for 2 hours at which time MeI (1.43 mL, 23.0 mmol, 10.0 eq) and dry DMF (10 mL) were added. The reaction was allowed to warm to room temperature overnight while stirring for 18 hours. The reaction was quenched with H$_2$O and extracted with diethyl ether (3×75 mL). The combined organic layers were washed with brine, dried with Na$_2$SO$_4$ and concentrated under reduced pressure to give a solid. The solid was washed with cold hexanes to give the product as a white powder (0.900 g, 70%). mp 196.5-203° C. $^1$H NMR (400 MHz, CDCl$_3$): δ 3.42 (s, 3H), 3.43 (s, 3H), 3.45 (s, 3H), 3.46 (s, 3H), 6.05 (d, J=10.4 Hz, 2H), 6.07 (d, J=10.4 Hz, 2H), 6.13 (d, J=10.4 Hz, 2H), 6.14 (d, J=10.4 Hz, 2H), 7.24 (d, J=8.4 Hz, 2H), 7.31 (d, J=8.8 Hz, 2H), 7.32 (d, J=8.8 Hz, 2H), 7.51 (d, J=8.4 Hz, 1H) 7.56 (d, J=8.4 Hz, 2H), 7.65 (dd, J=8.4, 2.4 Hz, 1H), 8.59, (d, J=2.4 Hz, 1H); $^{13}$C NMR (125 MHz, CDCl$_3$): δ 161.50, 147.51, 142.26, 141.97, 138.24, 134.72, 133.23, 132.58, 129.05, 128.55, 128.11, 127.64, 120.71, 76.28, 75.07, 74.49, 73.77, 52.44, 52.39, 52.35. HRMS (Q-TOF, ES+) (m/z): [M+Z]$^+$ calculated for C$_{33}$H$_{31}$Cl$_2$NO$_2$, 576.1708. found, 575.1733. IR (neat): 3021, 2939, 2896, 2823, 1590, 1469, 1400, 1368, 1086, 1020, 950, 829, 760, 730 cm$^{-1}$. See FIGS. 16A and 16B.

Figure 17A:
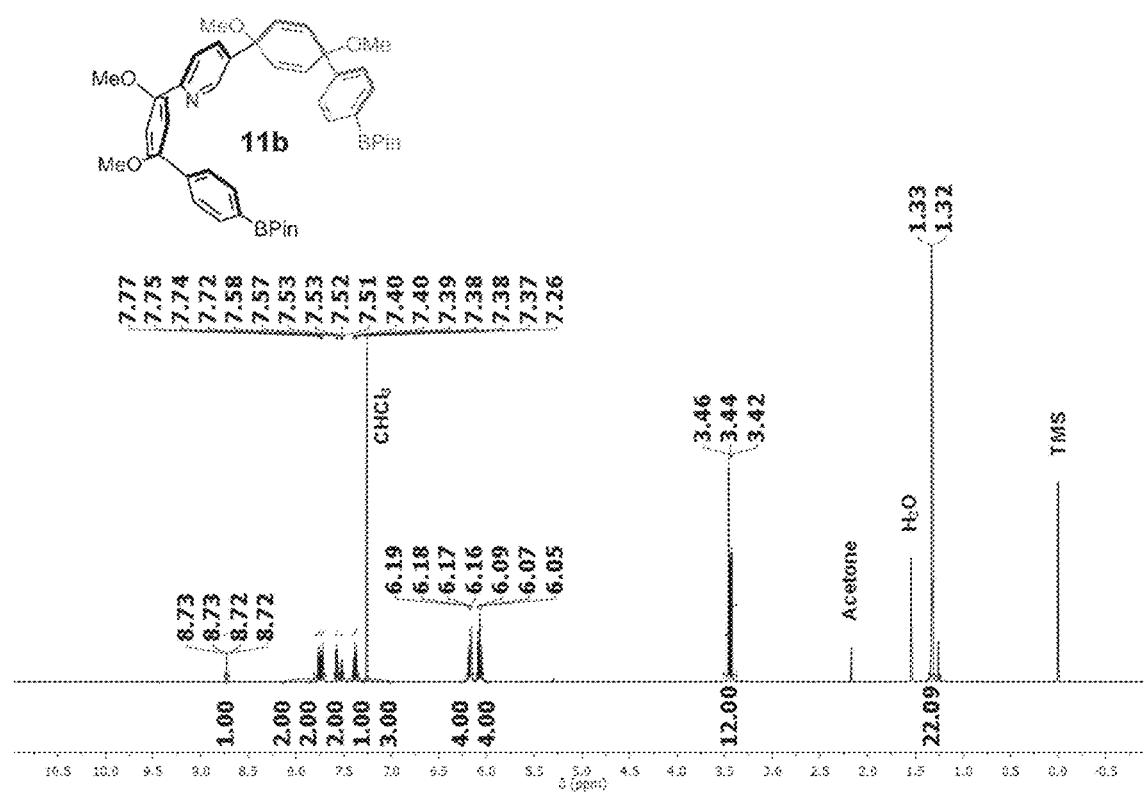
FIGS. 17A and 17B are $^1$H-NMR (FIG. 17A) and $^{13}$C-NMR (FIG. 17B) spectra of a nanohoop compound intermediate.
Figure 17B:
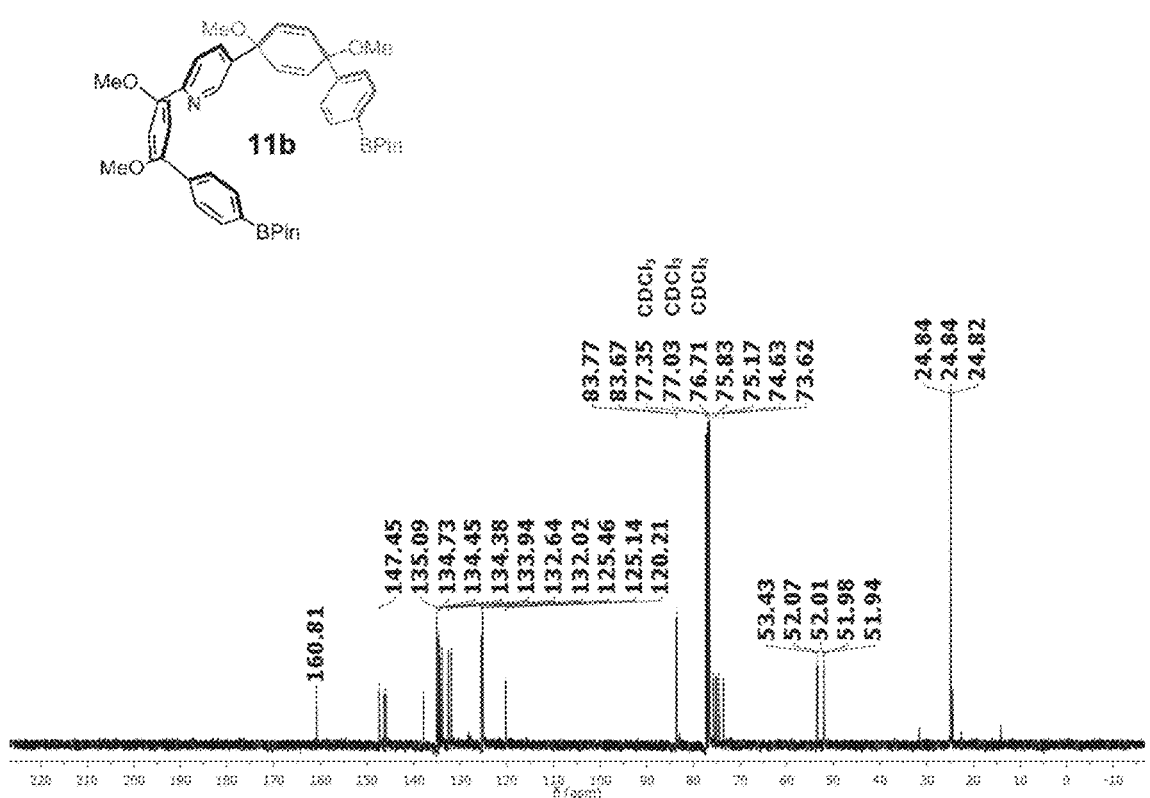

MHz, CDCl$_3$): δ 1.33 (m, 24H), 3.45 (multiplet, 12H), 6.12 (m, 8H), 7.39 (m, 3H), 7.55 (m, 3H), 7.75 (m, 4H), 8.73 (bs, 1H). $^{13}$C NMR (100 MHz, CDCl$_6$): δ HRMS (Q-TOF, ES+) (m/z): [M+H]$^+$ calculated for C$_{45}$H$_{55}$B$_2$NO$_8$, 760.4207. found, 760.4200. IR (neat): 2979, 2948, 2932, 2826, 1608, 1474, 1393, 1358, 1321, 1274, 1143, 1081, 1016, 950, 854, 758 cm$^{-1}$. See FIGS. 17A and 17B.

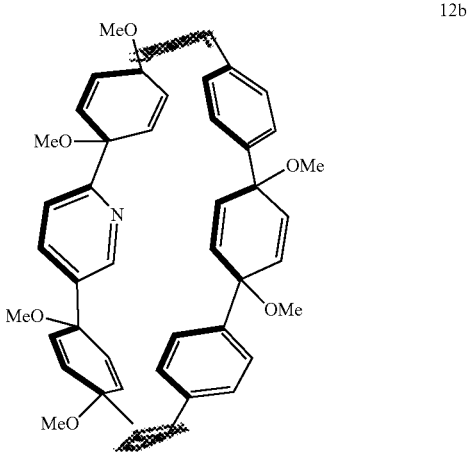

12b

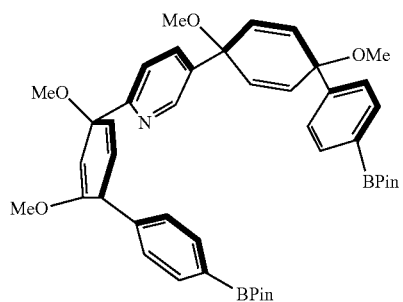

11b

Dichloride 10b (0.870 g, 1.51 mmol, 1.00 eq), B$_2$Pin$_2$ (2.30 g, 9.06 mmol, 6.00 eq), Pd(OAc)$_2$ (0.0300 g, 0.109 mmol, 0.100 eq). S-Phos (0.250 g, 0.604 mmol, 0.400 eq), and finely ground and oven dried K$_3$PO$_4$ (1.92 g, 9.06 mmol, 6.00 eq) were added to a dry flask. The flask was evacuated and backfilled with nitrogen 3 times. The solid was purged with N$_2$ for 30 minutes. Dry 1,4-dioxane (40 mL) was added to the flask via syringe. The mixture was stirred at 70° C. overnight. The mixture was cooled to room temperature and filtered through a pad of Celite with a top layer of activated carbon. The filtrate was extracted between DCM and H$_2$O. The combined organic layers were washed with H$_2$O followed by brine, before finally being dried over Na$_2$SO$_4$. The solvent was concentrated under reduced pressure to yield a white solid. The solid was washed with hexanes to give the pure product (0.487 g, 45%) mp 232-234° C. $^1$H NMR (400

Figure 18A:
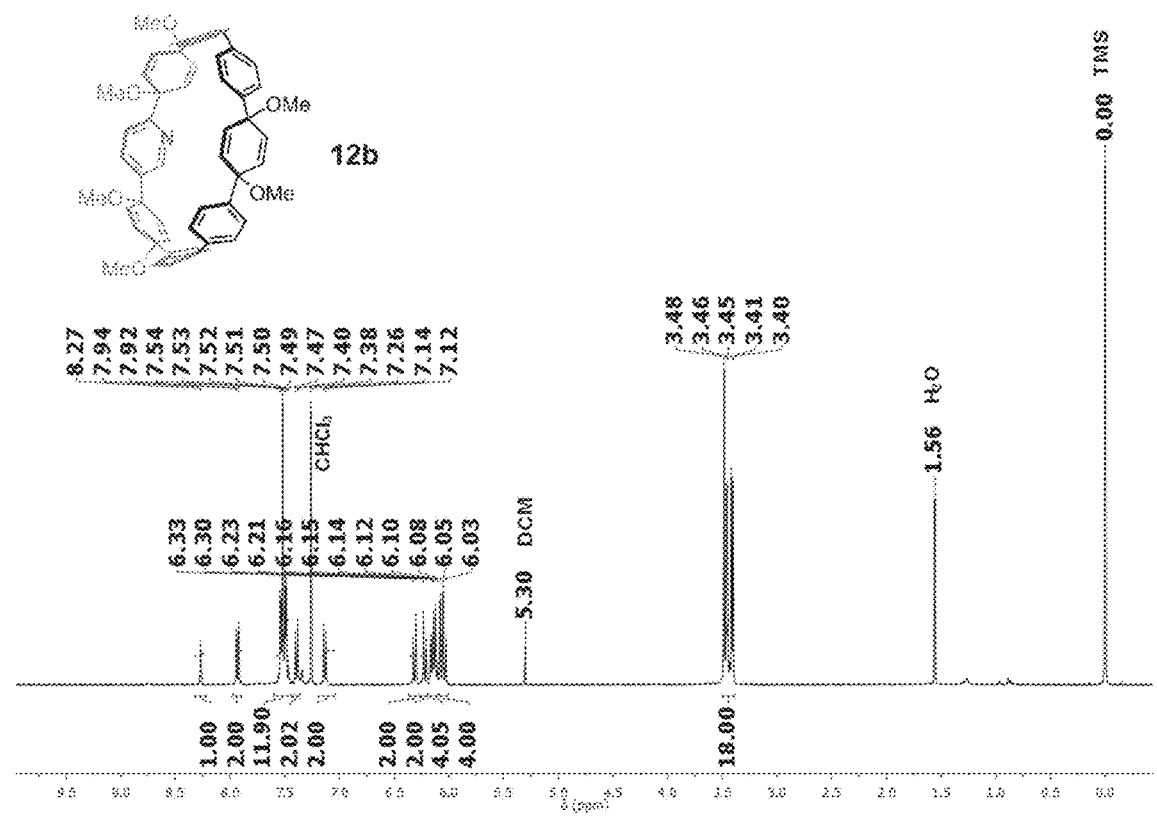
FIGS. 18A and 18B are $^1$H-NMR (FIG. 18A) and $^{13}$C-NMR (FIG. 18B) spectra of a cyclized nanohoop compound intermediate.
Figure 18B:
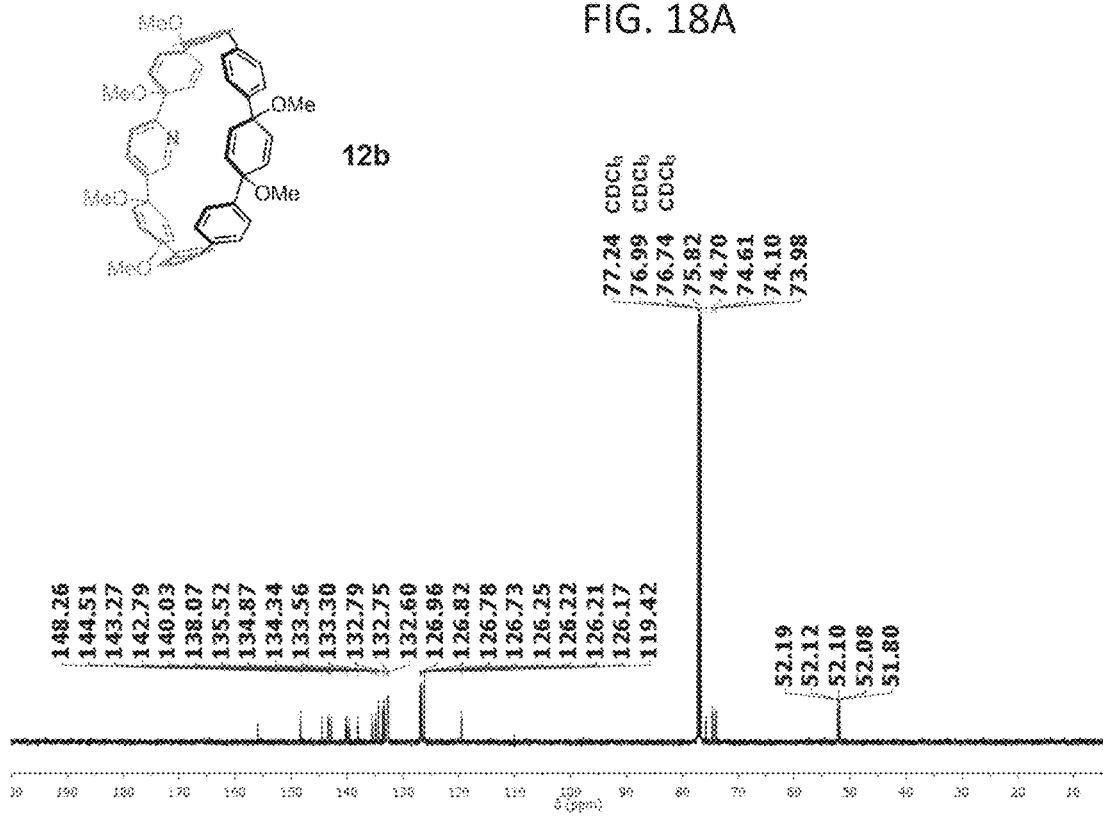

Dibromide 8a (0.585 g, 1.30 mmol, 1.00 eq), diboronate 11b (1.00 g, 1.30 mmol, 1.00 eq), $^n$Bu$_4$Br (0.084 g, 0.260 mmol, 0.200 eq) and Pd(PPh$_3$)$_4$ (0.150 g, 0.130 mmol, 0.100 eq,) NaHCO$_3$ (1.10 g, 13.0 mmol, 10.0 eq) were charged to a dried flask, which was then purged with argon. Degassed toluene (225 mL), methanol (25 mL), and water 13 mL (to make base 1 M) were added. The mixture was heated to 90° C. and stirred for 24 hours. The reaction was cooled to room temperature and washed with water. The organic layer was washed with brine and dried over sodium sulfate. The organic layer was concentrated down under reduced pressure to a yellow solid. The solid was purified by column chromatography (silica gel, 30% ethyl acetate in DCM eluent) to recover a white solid. Material was further purified by washes with cold ethyl acetate (0.257 mg, 25%) mp 285° C. dec. $^1$H NMR (500 MHz, CDCl$_3$): δ 3.40-3.48 (m, 18H), 6.02-6.17 (m, 8H), 6.22 (d, J=10 Hz, 2H), 6.32 (d, J=10.0 Hz, 2H) 7.13 (d, J=8.6 Hz, 2H), 7.39 (d, J=8.6 Hz, 2H), 7.50 (m, 12H), 7.93 (m, 2H), 8.26 (m, 1H). $^{13}$C NMR (125 MHz, CDCl$_3$): δ 52.11, 52.39, 52.41, 52.43, 52.50, 74.29, 74.41, 74.92, 75.01, 76.13, 119.73, 126.49, 126.52, 126.53, 127.04, 127.13, 132.91, 133.06, 133.10, 133.61, 133.87, 134.65, 135.18, 135.83, 143.10, 143.58, 148.57, 156.25. MALDI-TOF (m/z): [M+H]$^+$ calculated for C$_{53}$H$_{49}$NO$_6$, 795.36. found, 795.45 and 767.27 (loss of methoxy). IR (neat): 2982, 2926, 2896, 2823, 1589, 1490, 1081, 1069, 1014, 978, 852 cm$^{-1}$. See FIGS. 18A and 18B.

12c

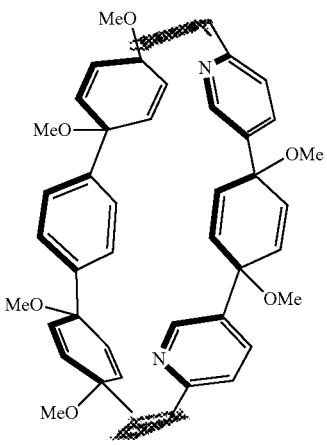

Figure 19A:
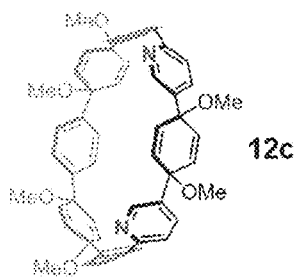
FIGS. 19A and 19B are $^1$H-NMR (FIG. 19A) and $^{13}$C-NMR (FIG. 19B) spectra of a cyclized nanohoop compound intermediate.
Figure 19A:
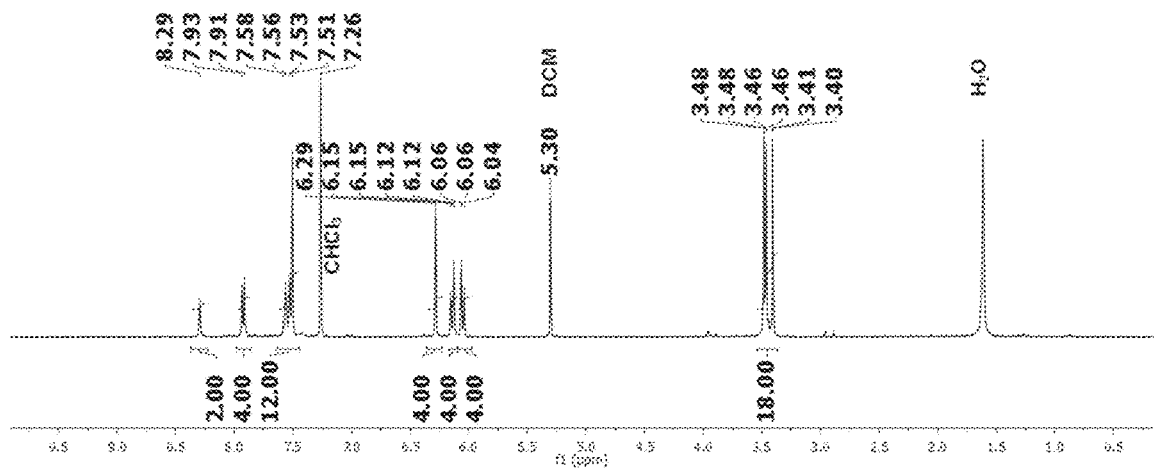
Figure 19B:
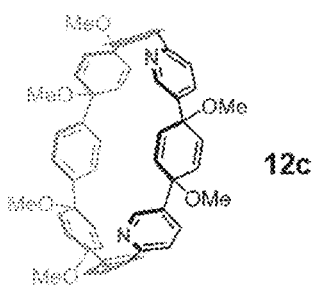
Figure 19B:
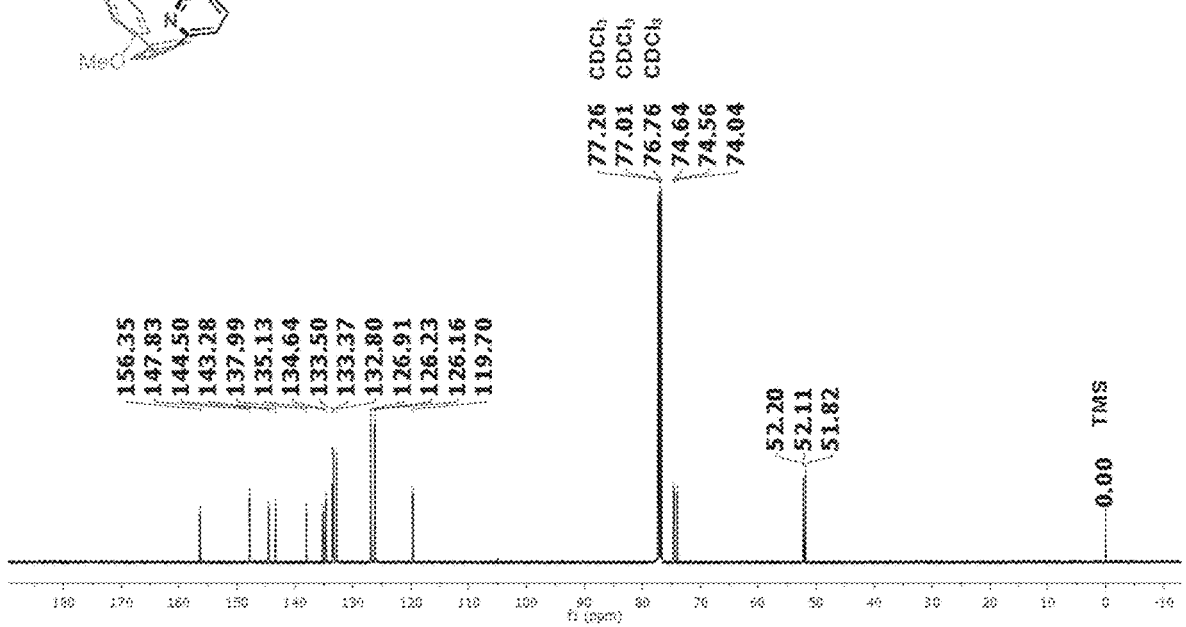

Dibromide 8d (0.415 g, 0.920 mmol, 1.00 eq), diboronate 11a (0.700 g, 0.920 mmol, 1.00 eq), "Bu₄NBr (0.323 g, 0.184 mmol, 0.200 eq) and Pd(PPh₃)₄ (0.106 g, 0.0920 mmol, 0.100 eq), and NaHCO₃ (0.865 g, 10.0 mmol, 10.0 eq) were charged to a dried flask, which was then evacuated and backfilled with N₂ three times. Degassed toluene (118 mL), methanol (13 mL) and H₂O (10 mL to make base 1 M) were added. The mixture was heated to 90° C. and stirred for 24 hours. The reaction was cooled to room temperature and extracted between washed with H₂O. The organic layer was washed with brine and dried over sodium sulfate. The organic layer was concentrated down under reduced pressure to a yellow solid. The solid was purified by column chromatography (silica get, 30% ethyl acetate in DCM eluent) to give a white solid (140 mg, 20%) mp 290° C. dec. ¹H NMR (500 MHz, CDCl₃): δ 3.40 (s, 6H), 3.46 (s, 6H), 3.48 (s, 6H), 6.05 (d, J=10 Hz, 4H), 6.13 (d, J=10 Hz, 4H), 6.28 (s, 4H), 7.51-7.57 (m, 12H), 7.92 (d, J=8.5 Hz, 4H), 8.29 (dd, J=2 Hz, 1 Hz, 2H). ¹³C NMR (125 MHz, CDCl₃): δ 52.11, 52.41, 52.49, 74.33, 74.85, 74.93, 119.99, 126.45, 126.52, 127.20, 133.09, 133.66, 133.79, 134.93, 135.42, 138.28, 143.57, 144.79, 148.12, 156.64. MALDI-TOF (m/z): [M+H]⁺ calculated for $C_{52}H_{48}N_2O_6$, 796.35. found 797.52. IR (neat): 3022, 2983, 2920, 2850, 2821, 1589, 1471, 1390, 1229, 1081, 1068, 101, 102, 978, 829, 662, 610, 543 cm⁻¹. See FIGS. 19A and 19B.

12d

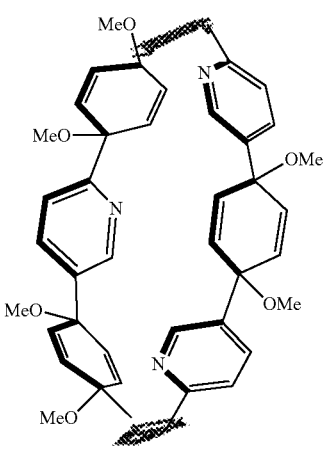

Figure 20A:
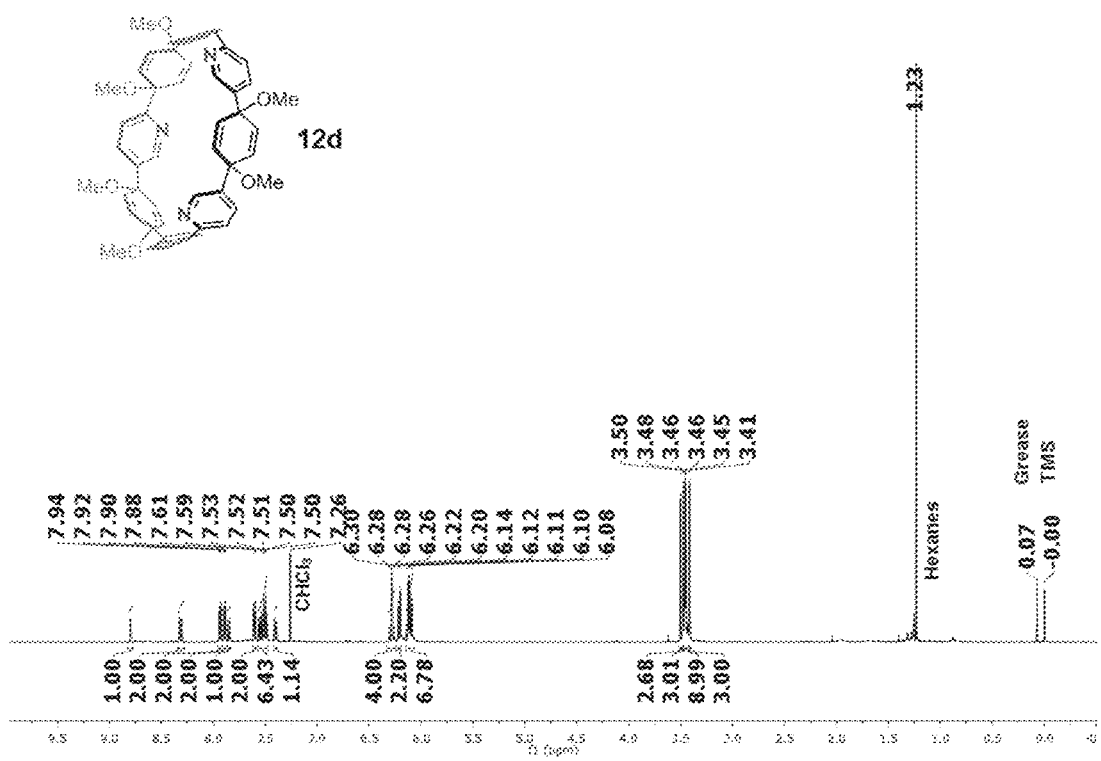
FIGS. 20A and 20B are $^1$H-NMR (FIG. 20A) and $^{13}$C-NMR (FIG. 20B) spectra of a cyclized nanohoop compound intermediate.
Figure 20B:
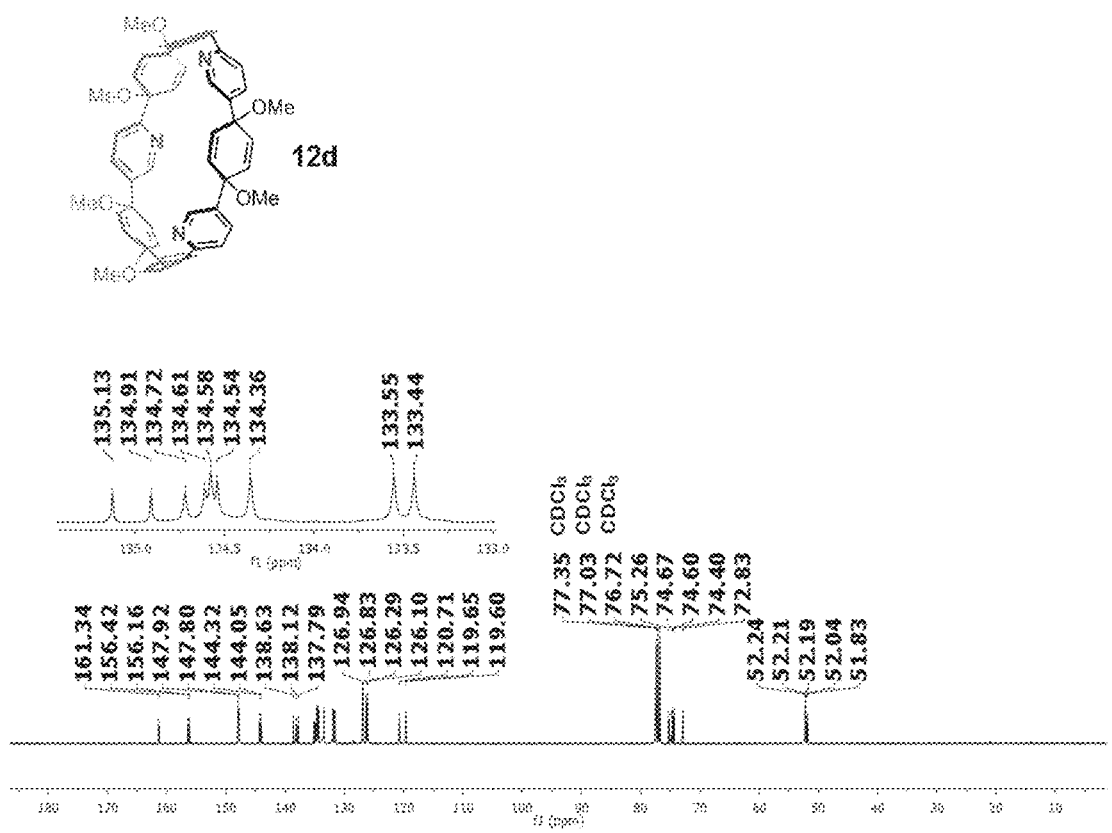

Dibromide 8d (0.178 g, 0.395 mmol, 1.00 eq), diboronate 11b (0.300 g, 0.395 mmol, 1.00 eq), "Bu₄Br (0.0250 g, 0.0790 mmol, 0.200 eq) and Pd(PPh₃)₄ (0.0500 g, 0.0400 mmol, 0.100 eq), and NaHCO₃ (0.336 g, 4.00 mmol, 10.0 eq) were charged to a dried flask, which was then evacuated and backfilled with N₂ three time. Degassed toluene (180 mL), methanol (20 mL), and H₂O (4 mL to make base 1 M) were added. The mixture was heated to 90° C. and stirred for 24 hours. The reaction was cooled to room temperature and washed with H₂O. The organic layer was washed with brine and dried over sodium sulfate. The organic layer was concentrated down under reduced pressure to a yellow solid. The solid was purified by column chromatography (silica gel, 40% ethyl acetate in DCM eluent) to recover a white solid (16.0 mg, 16%) mp 290° C. dec. ¹H NMR (500 MHz, CDCl₃): δ 3.42-3.51 (m, 18H), 6.09-6.29 (m, 12H), 7.40 (dd, J=8.3, 2.3 Hz, 1H), 7.49-7.61 (m, 8H), 7.84 (dd, J=8.3, 2.3 Hz, 1H), 7.88-7.95 (m, 4H), 8.30 (s, 1H), 8.32 (s, 1H), 8.80 (d, J=2.3 Hz, 1H). ¹³C NMR (125 MHz, CDCl₃) δ 161.47, 156.55, 156.28, 148.04, 147.92, 144.44, 144.18, 134.85, 134.73, 134.70, 134.67, 134.48, 133.68, 133.57, 131.99, 131.70, 127.06, 126.41, 126.22, 120.83, 119.78, 119.72, 75.39, 74.90, 74.80, 74.72, 74.52, 72.96, 52.36, 52.34, 52.32, 52.7, 51.95. MALDI-TOF (m/z): [M+H]⁺ calculated for $C_{51}H_{47}N_3O_6$, 797.35. found, 799.56. IR: 3023, 2935, 2896, 2822, 1590, 1556, 1470, 1393, 1227, 1175, 1114, 1074, 1014, 948, 825, 771, 753, 730, 662, 645, 610, 573, 543 cm⁻¹. See FIGS. 20A and 20B.

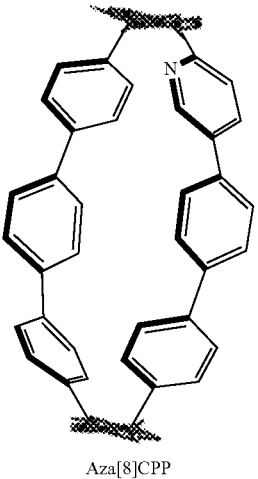

Aza[8]CPP

To a dry flask charged with 15 mL of THF was added sodium metal (0.200 g, 8.30 mmol) and naphthalene (1.20 g, 9.36 mmol). The solution was stirred for 15 hours at room temperature during which time a dark green solution of sodium naphthalide formed.

Figure 21A:
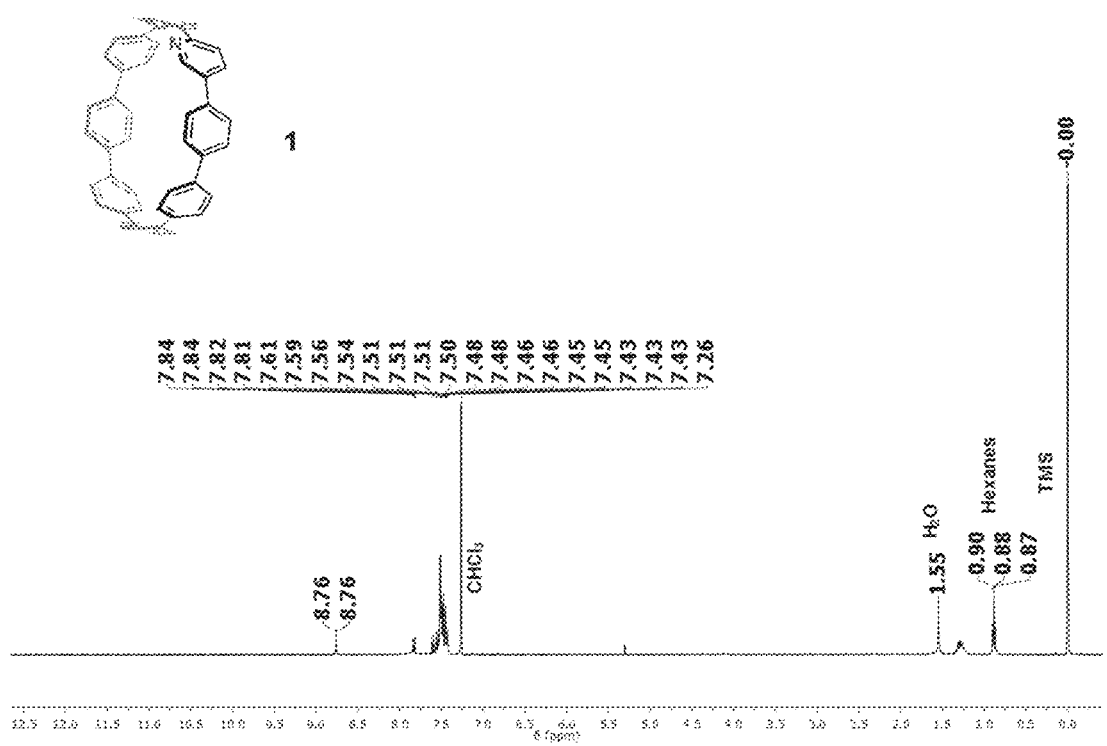
FIGS. 21A and 21B are $^1$H-NMR (FIG. 21A) and $^{13}$C-NMR (FIG. 21B) spectra of a representative non-functionalized nanohoop.
Figure 21B:
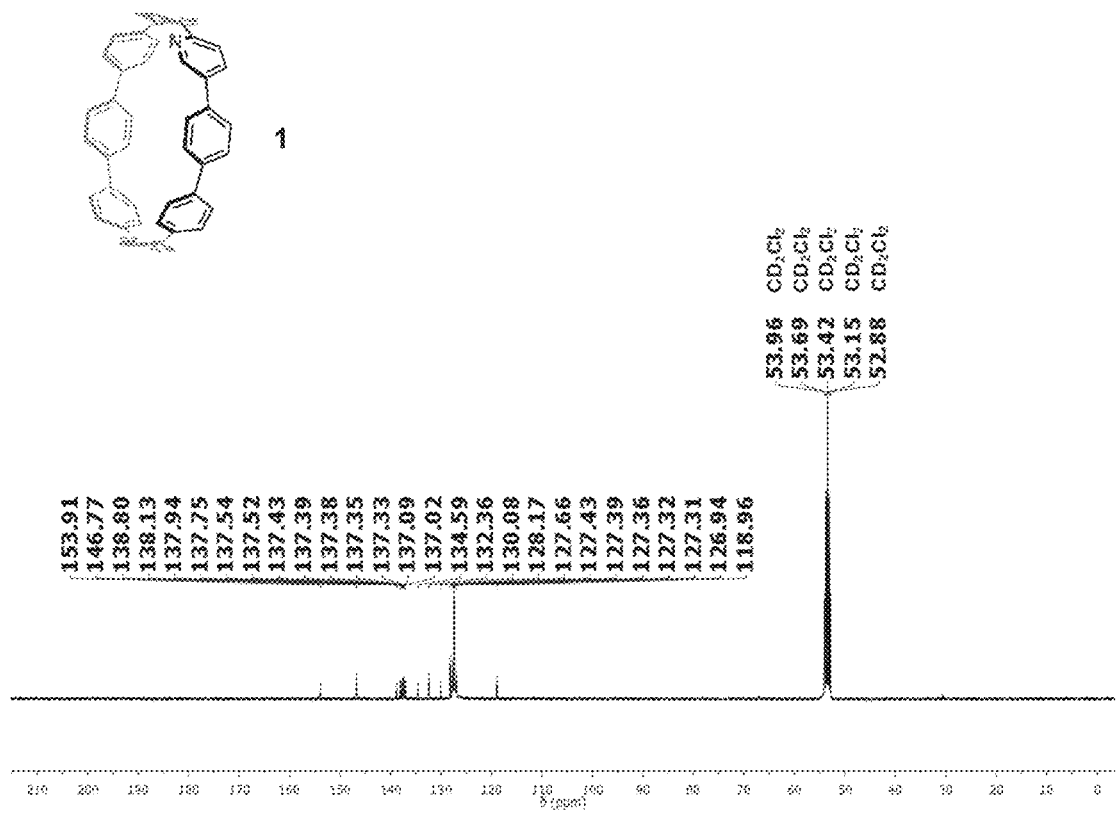

Macrocycle 12b (0.200 g, 0.250 mmol, 1.00 eq) was dissolved in dry THF (20 mL) and cooled to −78° C. To this solution, sodium naphthalide was added dropwise until the solution sustained a dark purple color (approximately 3 eq. per OMe, 3 mL naphthalide). The reaction was stirred for an additional 30 mins at −78° C. The reaction was quenched with a solution of 12 in THF (1 mL of 1 M solution). The solution was warmed to room temperature. The mixture was extracted with DCM and was washed with saturated sodium thiosulfate to quench excess iodine. The aqueous layer was extracted with DCM (3×10 mL). The combined organic layers were washed with brine and dried over sodium sulfate. The solvent was removed under reduced pressure to yield an orange solid. The solid was purified by column (5% ether/DCM eluent) followed by preparative TLC with the same solvent system (silica, 5% ether/DCM eluent). The pure product was received as an yellow solid (0.0860 g, 56%) mp 250° C. dec. $^1$H NMR (400 MHz, CDCl$_3$): δ 7.43-7.61 (m, 28H), 7.81-7.84 (m, 2H), 8.76 (s, 1H). $^{13}$C NMR (125 MHz. CDCl$_3$): δ 153.99, 140.85, 137.62, 17.60, 137.47, 137.45, 137.43, 137.42, 134.67, 132.45, 130.16, 128.25, 127.6, 127.51, 127.47, 119.04. MALDI-TOF (m/z): [M+H]$^+$ calculated for C$_{47}$H$_{31}$N, 609.25. found, 609.9299. IR (neat): 3023, 2923, 2853, 1567, 1479, 1467, 1390, 1364, 1261, 1224, 1055, 996, 816, 760, 741 cm$^{-1}$. See FIGS. 21A and 21B.

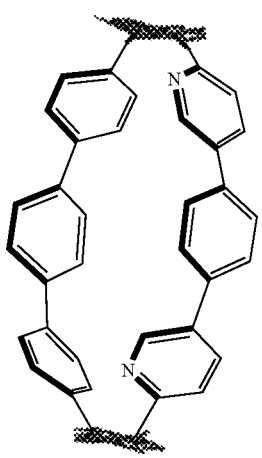

1,15-Diaza[8]CPP

To a dry flask charged with 15 mL of THF was added sodium metal (0.200 g, 8.30 mmol) and naphthalene (1.20 g, 9.36 mmol). The solution was stirred for 15 hours at room temperature during which time a dark green solution of sodium naphthalide formed.

Figure 22A:
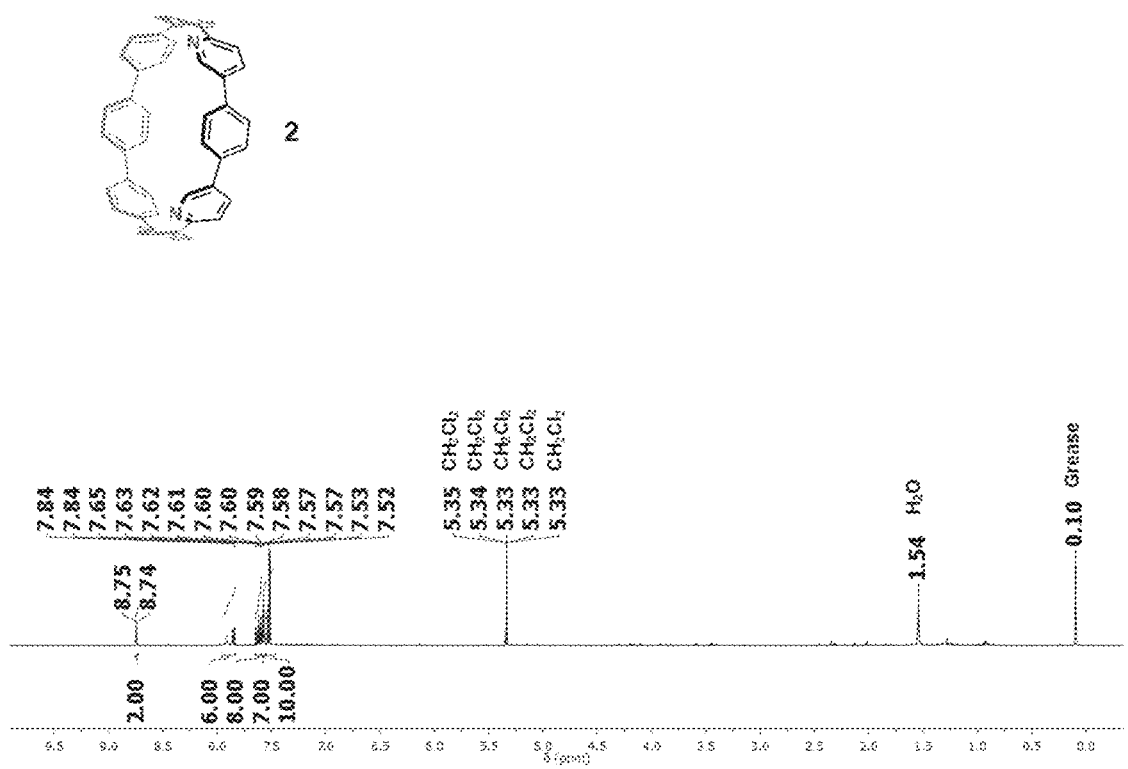
FIGS. 22A and 22B are $^1$H-NMR (FIG. 22A) and $^{13}$C-NMR (FIG. 22B) spectra of a representative non-functionalized nanohoop.
Figure 22B:
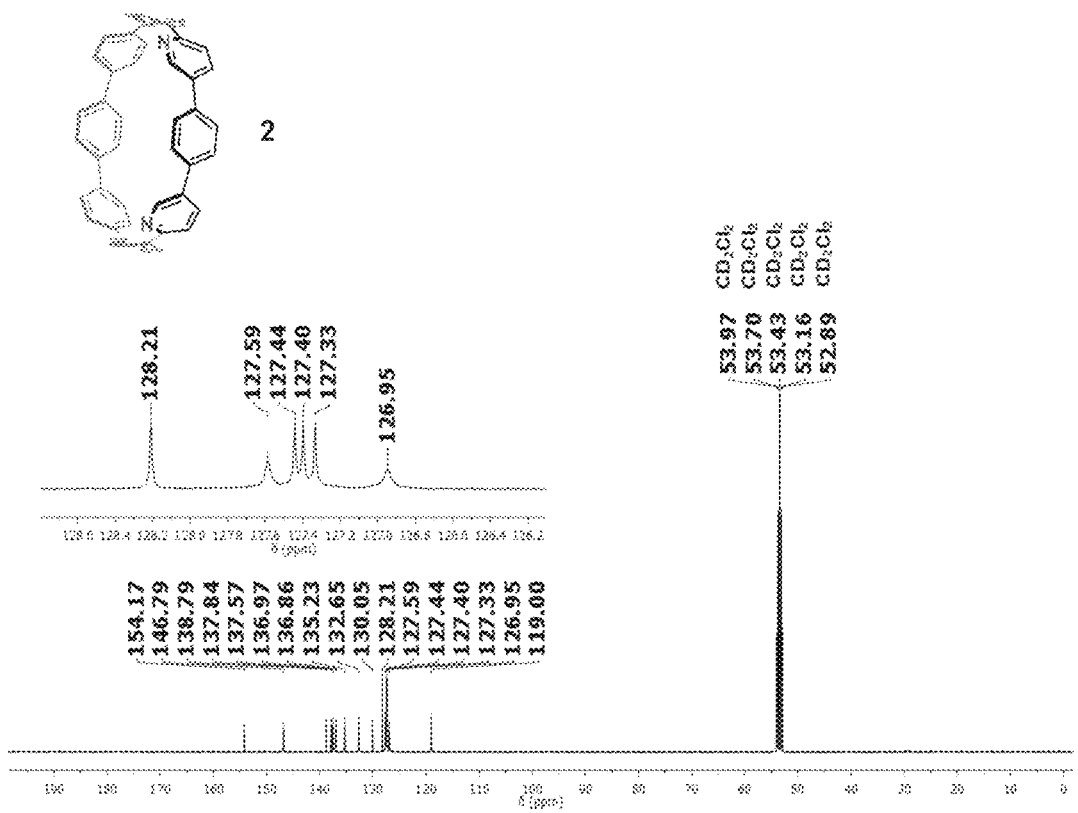

Macrocycle 12c (0.174 g, 219 mmol, 1.00 eq) was dissolved in dry THF (20 mL) and cooled to −78° C. To this solution, sodium naphthalide was added dropwise until the solution sustained a dark purple color (approximately 2 mL of 1 M sodium naphthalide). The reaction was stirred for an additional 3 hours at −78° C. The reaction was quenched with a solution of I$_2$ in THF (1 mL of 1 M solution). The solution was warmed to room temperature. The reaction was extracted with DCM and was washed with saturated sodium thiosulfate to quench excess iodine. The aqueous layer was extracted with DCM (3×10 mL). The combined organic layers were washed with brine and dried over sodium sulfate. The solvent was removed under reduced pressure to yield an orange solid. The solid was washed with hexanes to remove excess naphthalene. The solid was then purified by prepatory TLC (silica, 5% MeOH/DCM eluent). The pure product was received as a yellow solid (0.0720 g, 55%) mp 236° C. dec. $^1$H NMR (500 MHz, CDCl$_3$): δ 7.26-7.86 (m, 28H), 8.75 (s, 2H). $^{13}$C NMR (125 MHz. CDCl$_3$): δ 154.24, 146.86, 138.86, 137.91, 137.64, 137.04, 136.94, 135.31, 132.72, 130.13, 128.28, 127.66, 127.52, 127.47, 127.41, 127.02, 119.07. MALDI-TOF (m/): [M+H]$^+$ calculated for C$_{48}$H$_{30}$N$_2$, 610.24. found, 611.26. IR (neat): 2967, 2879, 1472, 880, 830, 739, 556 cm$^{-1}$. See FIGS. 22A and 22B.

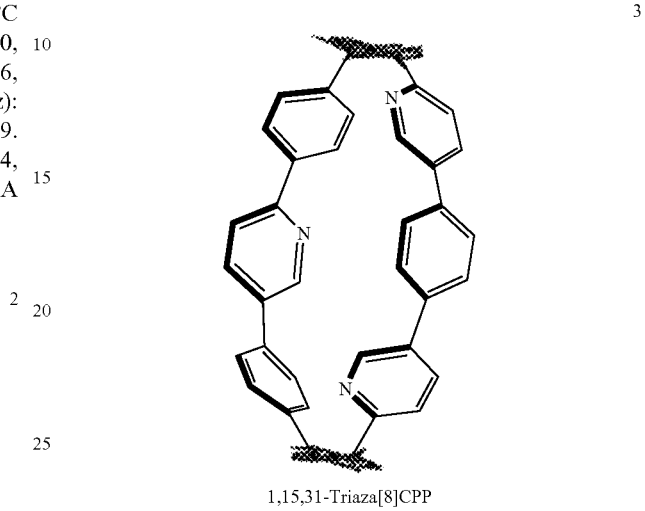

1,15,31-Triaza[8]CPP

To a dry flask charged with 15 mL of THF was added sodium metal (0.200 g, 8.30 mmol) and naphthalene (1.20 g, 9.36 mmol). The solution was stirred for 15 hours at room temperature during which time a dark green solution of sodium naphthalide formed.

Figure 23A:
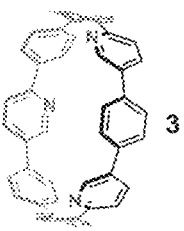
FIGS. 23A and 23B are $^1$H-NMR (FIG. 23A) and $^{13}$C-NMR (FIG. 23B) spectra of a representative non-functionalized nanohoop.
Figure 23A:
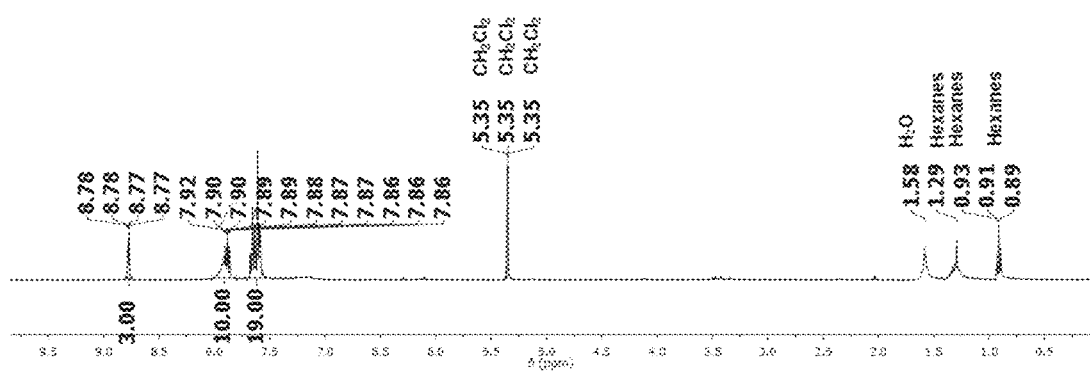
Figure 23B:
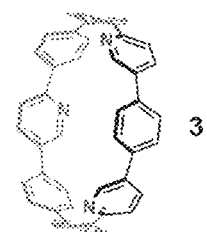
Figure 23B:
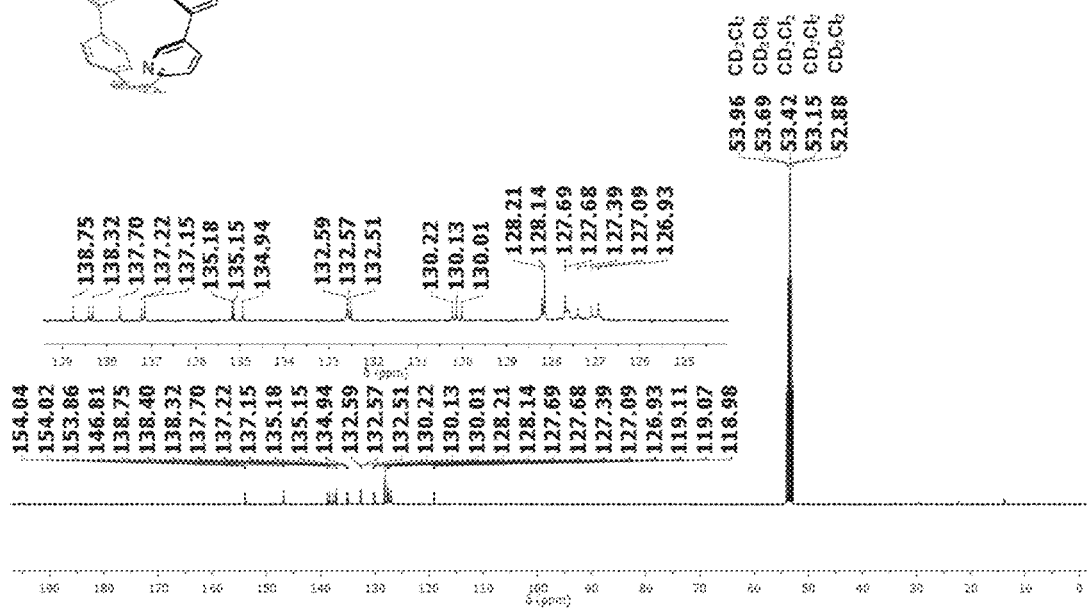

Macrocycle 12d (0.0500 g, 0.0630 mmol, 1.00 eq) was dissolved in dry THF (15 mL) and cooled to −78° C. To this solution, sodium naphthalide was added dropwise until the solution sustained a dark purple color (approximately 3 eq per OMe). The reaction was stirred for an additional 30 mins at −78° C. The reaction was quenched with a solution of I$_2$ in THF (1 mL of 1 M solution). The solution was warmed to room temperature. The mixture was extracted with DCM and washed with saturated sodium thiosulfate to quench excess iodine. The aqueous layer was extracted with DCM (3×10 mL). The combined organic layers were washed with brine and dried over sodium sulfate. The solvent was removed under reduced pressure to yield an orange solid. The solid was washed with a small amount of hexanes to remove most of the excess naphthalene. The residue was then purified by preparatory TLC (silica, 20% ether/DCM eluent). The pure product was received as a yellow solid (0.0190 g, 50%) mp 230° C. dec. $^1$H NMR (500 MHz, CDCl$_3$): δ 7.51-7.61 (m, 17H), 7.79-7.86 (m, 9H), 8.75-8.77 (m, 3H). $^{13}$C NMR (125 MHz, CDCl$_3$): δ 154.13, 154.11, 153.94, 146.89, 138.83, 138.48, 138.40, 137.79, 137.30, 137.23, 135.26, 135.23, 135.02, 132.67, 132.65, 132.59, 130.22, 130.09, 128.29, 128.23, 127.77, 127.76, 127.47, 127.17, 127.02, 119.20, 119.15, 119.06. MALDI-TOF (m/z): [M+H]$^+$ calculated for C$_{45}$H$_{29}$N$_3$, 611.24. found, 612.32. IR (neat): 3026, 2924, 2853, 1733, 1567, 1463, 1363, 1263, 1228, 1174, 1153, 1114, 1077, 1015, 948, 911, 819, 740, 699, 664, 650 cm$^{-1}$. See FIGS. 23A and 23B.

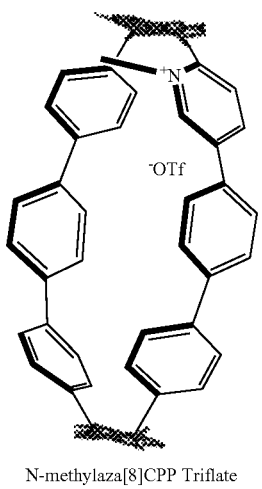

N-methylaza[8]CPP Triflate

Figure 24A:
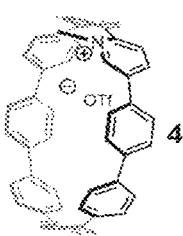
FIGS. 24A and 24B are $^1$H-NMR (FIG. 24A) and $^{13}$C-NMR (FIG. 24B) spectra of a nanohoop compound.
Figure 24A:
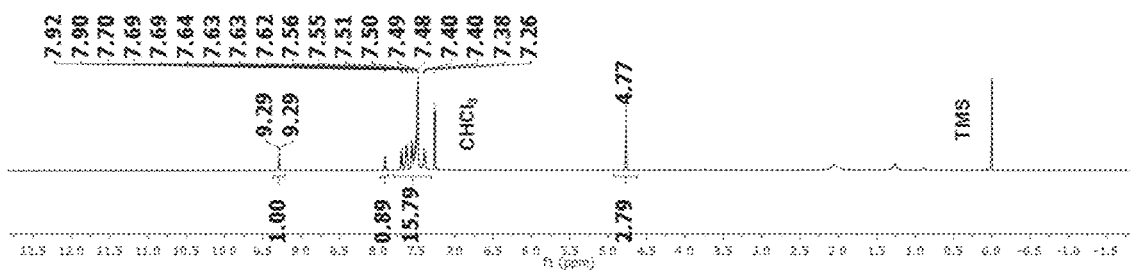
Figure 24B:
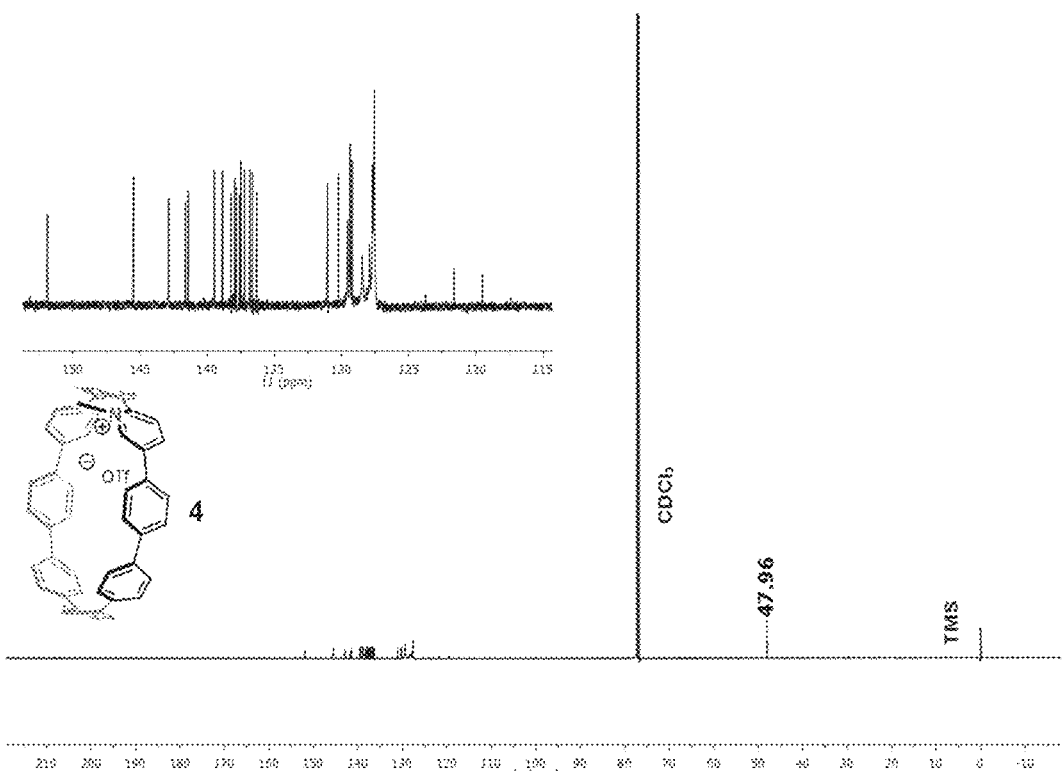

Aza[8]CPP 1 (0.0230 g, 0.0377 mmol, 1 equiv) was added to a flame dry flask charged under nitrogen. 20 mL of dry dichloromethane was added. Once all solids had dissolved methyl triflate (0.0200 mL, 0.189 mmol, 5 equiv) was added dropwise. This was allowed to stir for 18 hours during which the color turned from a bright fluorescent yellow to a dull orange. The reaction was quenched by addition of saturated ammonium chloride (20 mL). The aqueous layer was extracted with DCM (3×10 mL). The combined organic layers were washed with brine and dried over sodium sulfate. The solvent was removed under reduced pressure to yield a red/orange solid (0.0290 g, 99%). Single crystal was grown by slow liquid diffusion by layering toluene onto a concentrated dichloromethane solution of 4. mp 230° C. dec. $^1$H NMR (600 MHz, CDCl$_3$): δ 9.29 (s, 1H), 7.91 (d, J=9 Hz, 1H), 7.70 (d, J=9 Hz, 1H), 7.64-7.26 (m, 19H), 4.76 (s, 3H). $^{13}$C NMR (150 MHz, CDCl$_3$): δ 151.90, 145.48, 142.88, 141.61, 141.40, 139.48, 138.87, 138.23, 137.95, 137.82, 137.60, 137.50, 137.22, 136.81, 136.64, 136.30, 131.06, 130.24, 129.54, 129.37, 128.46, 127.92, 127.70, 127.57, 121.58 (q, J$_{C-F}$ 318 Hz), 47.96. ESI-MS (m/z): [M+Na]$^+$ calculated for C$_{49}$H$_{34}$NF$_3$NNaO$_3$S$^+$, 796.2109. found, 796.2096. IR (neat): 3025, 2923, 1585, 1486, 1260, 1165, 1029, 822, 730, 638 cm$^{-1}$. See FIGS. 24A and 24B.

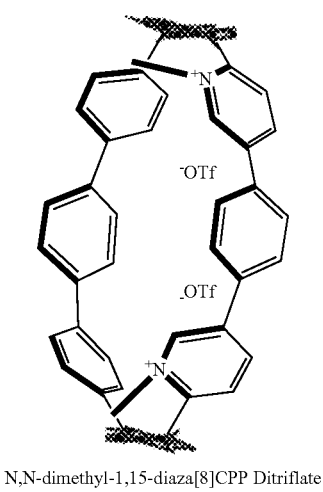

Figure 25A:
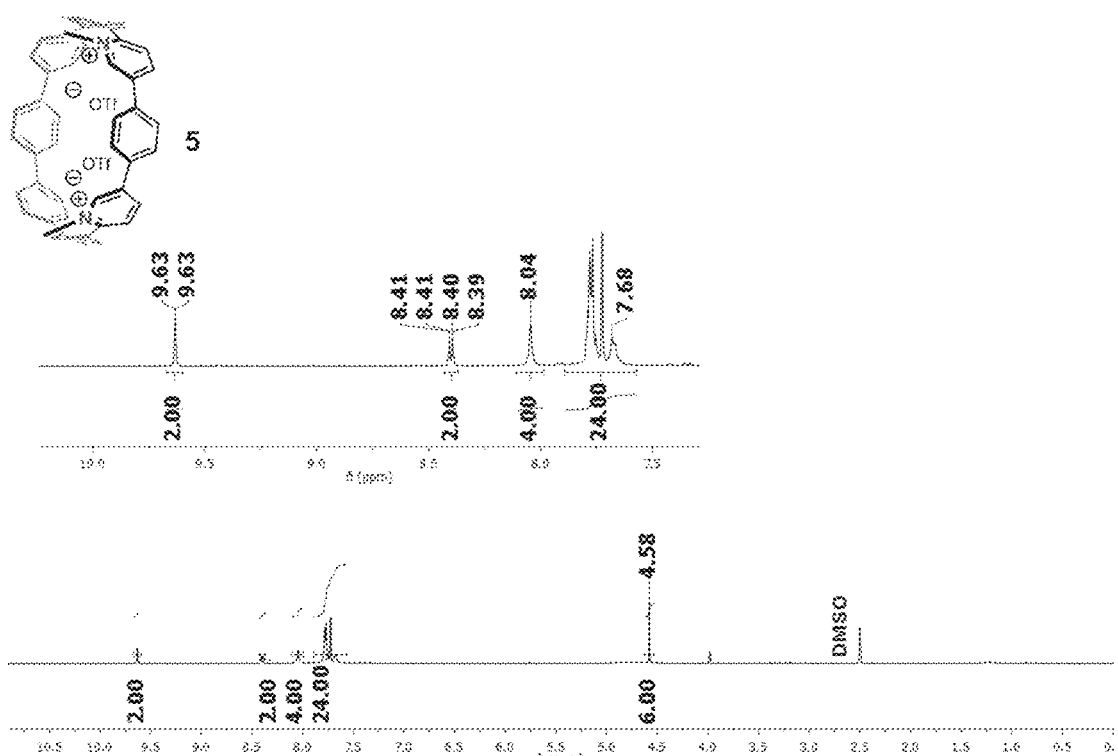
FIGS. 25A and 25B are $^1$H-NMR (FIG. 25A) and $^{13}$C-NMR (FIG. 25B) spectra of a representative nanohoop compound.
Figure 25B:
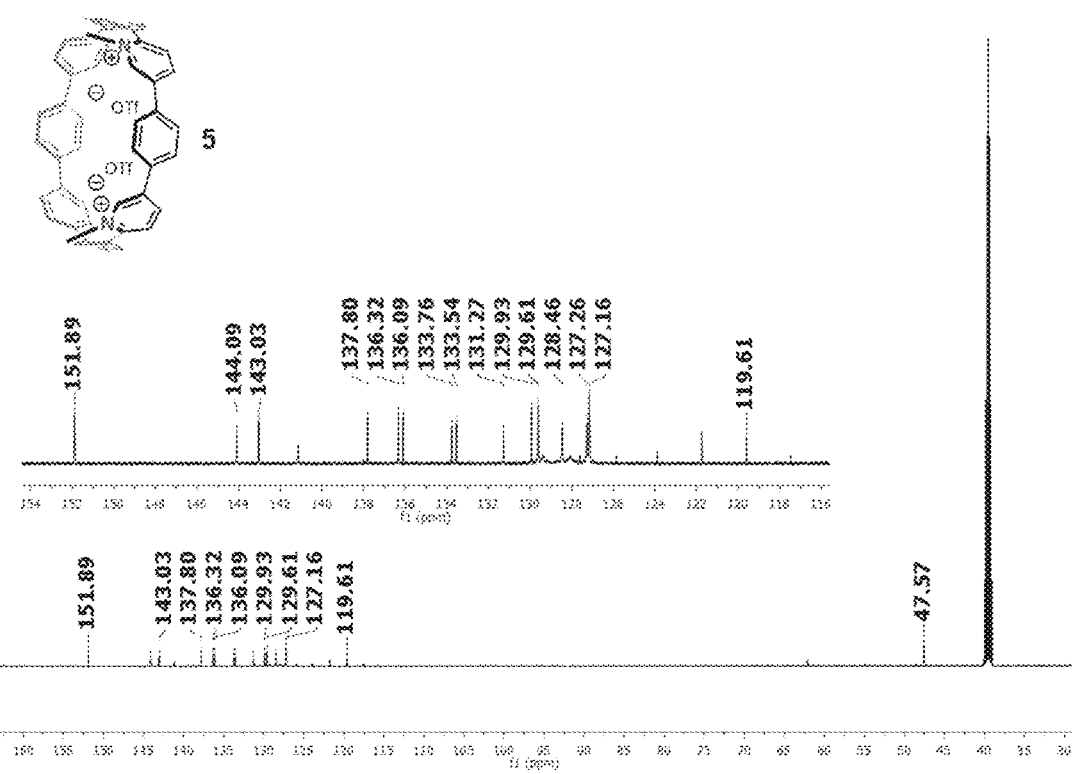

N,N-dimethyl-1,15-diaza[8]CPP Ditriflate 1,15-diaza[8]CPP2N 2 (0.0170 g, 0.0383 mmol, 1 equiv) was added to a flame dry flask charged under nitrogen. 20 mL of dry dichloromethane was added. Once all solids had dissolved methyl triflate (0.0280 mL, 0.283 mmol, 10 equiv) was added dropwise. This was allowed to stir for 18 hours during which the color turned from a bright fluorescent yellow to a dull orange. The reaction was quenched by addition of saturated ammonium chloride (20 mL). The aqueous layer was extracted with DCM (3×10 mL). The combined organic layers were washed with brine and dried over sodium sulfate. The solvent was removed under reduced pressure to yield a red/orange solid (0.0263 g, 99%). Single crystals were grown by slow evaporation of CDCl$_3$. mp 230° C. dec. $^1$H NMR (600 MHz, DMSO d6): δ 9.63 (s, 2H), 8.40 (d, J=9 Hz, 2H), 8.05 (s, 4H), 7.82-7.62 (m, 24H), 4.58 (s, 6H). $^{13}$C NMR (150 MHz, DMSO): δ 151.89, 144.09, 143.03, 141.14, 137.80, 136.32, 136.09, 133.76, 133.54, 131.27, 129.93, 129.61, 129.39, 128.46, 128.08, 127.26, 127.16, 120.68 (q, J$_{C-F}$=320 Hz), 47.57. ESI-MS (m/z): [M+Na]$^+$ calculated for C$_{50}$H$_{36}$F$_6$N$_2$NaO$_6$S$_2$, 961.1816. found, 961.1819. IR (neat): 3058, 2925, 2854, 1590, 1523, 1435, 1258, 1166, 1030, 825, 734, 638, 574 cm$^{-1}$. See FIGS. 25A and 25B and FIG. 26 (with reference to FIG. 26, "Cl"=chlorine; "F"=fluorine; "O=oxygen; "S"=sulfur; "N"=nitrogen; "C"=carbon).

Crystallographic Data

Crystallographic Data for FIG. 1: C$_{52}$H$_{44}$O$_2$S$_2$, M=6764.99, 0.05×0.04×0.02 mm, T=173(2) K, Monoclinic, space group P2$_1$/c, a=13.3179(5) Å, b=9.3373(4) Å, c=16.7050(8) Å, β=105.759(2)°, V=1999.24(15) Å3, Z=2, D$_c$=1.271 Mg/m3, μ(Mo)=1.526 mm-1, F(000)=808, 2θ$_{max}$=106.6°, 17195 reflections, 2315 independent reflections [R$_{int}$=0.0592], R1=0.0468, wR2=0.1139 and GOF=1.078 for 2317 reflections (253 parameters) with I>2σ(I), R1=0.0625, wR2=0.1228 and GOF=1.078 for all reflections, max/min residual electron density +0.332/−0.402 eÅ$^3$.

Figure 26:
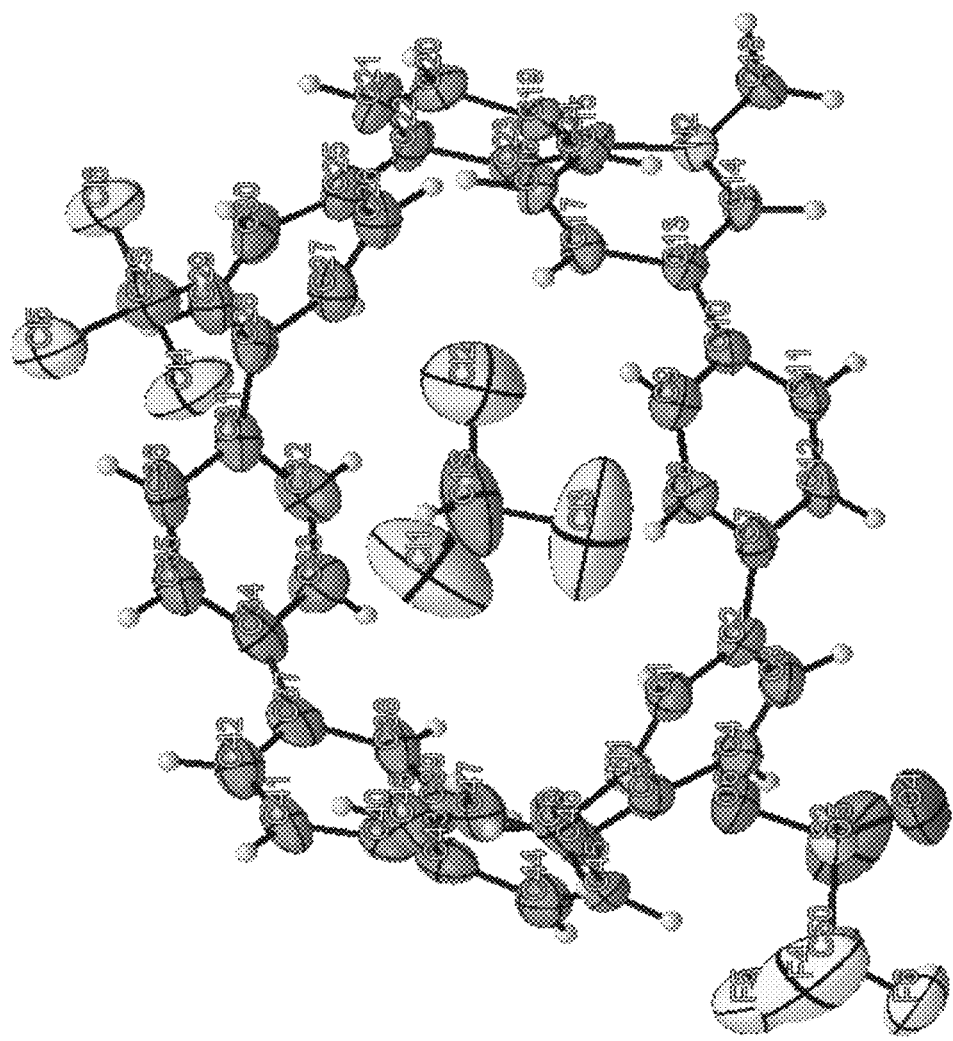
FIG. 26 is an ORTEP representation of the X-ray crystallographic structure of a representative functionalized nanohoop compound.
Figure 26:
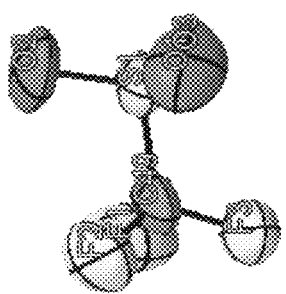

Crystallographic Data for FIG. 26: C$_{56}$H$_{42}$Cl$_{18}$F$_6$N$_2$O$_6$S$_2$, M=1655.13, 0.13×0.08×0.03 mm, T=200(2) K, Monoclinic, space group P2$_1$/c, a=24.745(12) Å, b=10.384(5) Å, c=27.866(13) Å, β=96.257(11)°, V=7117(6) Å3, Z=4, D$_c$=1.545 Mg/m3, μ(Mo)=7.445 mm-1, F(000)=3328, 2θ$_{max}$=135.3°, 29341 reflections, 7210 independent reflections [R$_{int}$=0.0828], R1=0.1035, wR2=0.3177 and GOF=1.036 for 7210 reflections (667 parameters) with I>2σ(I), R1=0.1285, wR2=0.3387 and GOF=1.036 for all reflections, max/min residual electron density +0.649/−0.497 eÅ$^3$.

Figure 27:
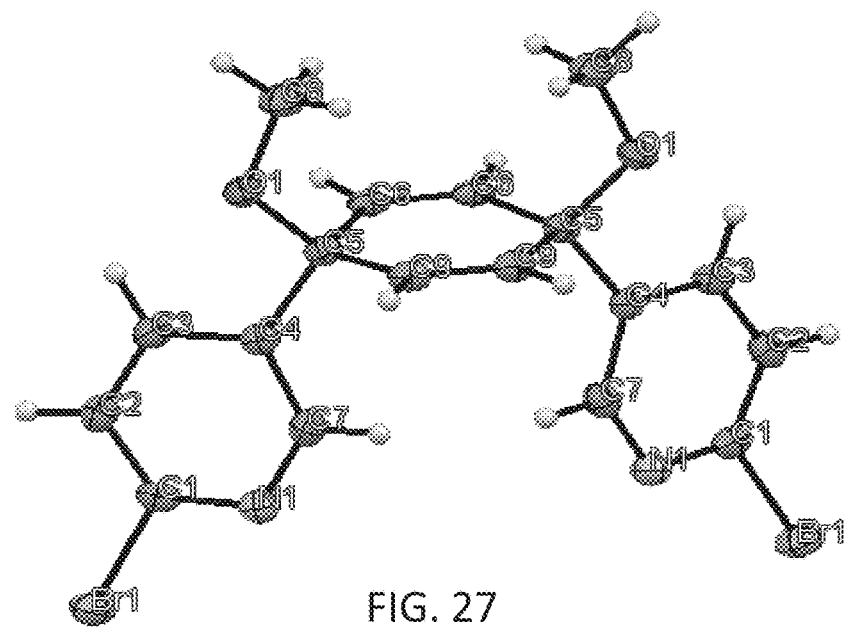
FIG. 27 is an ORTEP representation of the x-ray crystallographic structure of a representative compound used to make functionalized nanohoops.

Crystallographic Data for FIG. 27: C$_{18}$H$_{16}$Br$_2$N$_2$O$_2$, M=452.15, 0.22×0.08×0.03 mm, T=100 K, Orthorhombic, space group Pnma, a=12.562 (10) Å, b=20.755 (17) Å, c=6.453 (5) Å, V=1682.4 (2) Å3, Z=4, D$_c$=1.785 Mg/m3, μ(Cu)=6.23 mm-1, F(000)=896, 2θ$_{max}$=131.68°, 16796 reflections, 1497 independent reflections [R$_{int}$=0.0468], R1=0.0308, wR2=0.0806 and GOF=0.930 for 1497 reflections (110 parameters) with I>2σ(I), R1=0.0333, wR2=0.0806 and GOF=0.930 for all reflections, max/min residual electron density +0.89/−0.39 eÅ$^3$.

Cyclic Voltammetry Data

Cyclic voltammetry was conducted utilizing a platinum working electrode, platinum counter electrode, and a silver wire pseudoreference that was separated from the solution via a glass frit. Experiments were performed using a custom designed potentiostat at a scan rate of 50 mV/s. Analyte solutions were freeze-pump-thaw degassed three times and all experiments were conducted under airfree conditions. Analyte solutions were prepared using 0.1 M tetrabutylammonium tetrafluoroborate in THF, with analyte concentrations 1-5 mM. The Ag pseudoreference was calibrated versus the ferrocene/ferrocinium redox couple following the CV of each compound.

Computation Details

All calculations were carried out with Gaussian 09 package at B3LYP/6-31g* level of theory. Geometries were first optimized in the gas phase. Once optimized a single point calculation was carried out using the CPCM solvation model with acetonitrile as the solvent continuum to account for charged species. All excited state calculations (TD-DFT) were performed on fully optimized structures. The fully optimized structures were confirmed to be true minima by vibrational analysis. Structures were minimized with no symmetry restrictions.

SUPPLEMENTARY TABLE 1

Major electronic transitions for Aza[8]CPP 1 determined by TD-DFT method using B3LYP/6-31g*

| Energy (cm$^{-1}$) | Wavelength (nm) | Osc. Strength | Major contributions |
|---|---|---|---|
| 21813 | 458 | 0.0252 | HOMO->LUMO (97%) |
| 27563 | 363 | 0.2349 | H-1->LUMO (76%), HOMO->L + 1 (22%) |
| 27841 | 359 | 0.4107 | H-2->LUMO (37%), H-1->LUMO (14%), HOMO->L + 1 (44%) |
| 28068 | 356 | 1.4312 | H-2->LUMO (60%), HOMO->L + 1 (32%) |
| 28800 | 347 | 1.092 | HOMO->L + 2 (96%) |
| 31438 | 318 | 0.0443 | HOMO->L + 3 (81%) |
| 31728 | 315 | 0.0577 | H-2->L + 1 (14%), H-2->L + 2 (17%), H-1->L + 1 (59%) |
| 32008 | 312 | 0.0296 | H-2->L + 1 (44%), H-1->L + 1 (17%), H-1->L + 2 (26%) |
| 33290 | 300 | 0.0036 | H-5->LUMO (12%), HOMO->L + 4 (58%) |
| 33354 | 300 | 0.0187 | H-3->LUMO (36%), H-1->L + 2 (13%) |
| 33876 | 295 | 0.0021 | H-2->L + 1 (33%), H-1->L + 2 (48%) |
| 33996 | 294 | 0.0146 | H-2->L + 2 (65%), H-1->L + 1 (17%) |

SUPPLEMENTARY TABLE 2

Major electronic transitions for 1,15-diaza[8]CPP 2 determined by TD-DFT method using B3LYP/6-31g*

| Energy (cm$^{-1}$) | Wavelength (nm) | Osc. Strength | Major contributions |
|---|---|---|---|
| 21813 | 458 | 0.0252 | HOMO->LUMO (97%) |
| 27563 | 363 | 0.2349 | H-1->LUMO (76%), HOMO->L + 1 (22%) |
| 27841 | 359 | 0.4107 | H-2->LUMO (37%), H-1->LUMO (14%), HOMO->L + 1 (44%) |
| 28068 | 356 | 1.4312 | H-2->LUMO (60%), HOMO->L + 1 (32%) |
| 28800 | 347 | 1.092 | HOMO->L + 2 (96%) |
| 31438 | 318 | 0.0443 | HOMO->L + 3 (81%) |
| 31728 | 315 | 0.0577 | H-2->L + 1 (14%), H-2->L + 2 (17%), H-1->L + 1 (59%) |
| 32008 | 312 | 0.0296 | H-2->L + 1 (44%), H-1->L + 1 (17%), H-1->L + 2 (26%) |
| 33290 | 300 | 0.0036 | H-5->LUMO (12%), HOMO->L + 4 (58%) |
| 33354 | 300 | 0.0187 | H-3->LUMO (36%), H-1->L + 2 (13%) |
| 33876 | 295 | 0.0021 | H-2->L + 1 (33%), H-1->L + 2 (48%) |
| 33996 | 294 | 0.0146 | H-2->L + 2 (65%), H-1->L + 1 (17%) |

SUPPLEMENTARY TABLE 3

Major electronic transitions for 1,15,31-triaza[8]CPP 3 determined by TD-DFT method using B3LYP/6-31g*

| Energy (cm$^{-1}$) | Wavelength (nm) | Osc. Strength | Major contributions |
|---|---|---|---|
| 20895 | 479 | 0.0056 | HOMO->LUMO (97%) |
| 26474 | 378 | 0.3135 | H-1->LUMO (10%), HOMO->L + 1 (88%) |
| 26966 | 371 | 1.2147 | H-1->LUMO (87%) |
| 27332 | 366 | 0.6758 | H-2->LUMO (95%) |
| 28522 | 351 | 1.0314 | HOMO->L + 2 (97%) |
| 30548 | 327 | 0.0113 | H-1->L + 1 (84%) |
| 30865 | 324 | 0.018 | H-2->L + 1 (77%), H-1->L + 2 (19%) |
| 31323 | 319 | 0.0111 | HOMO->L + 3 (78%) |
| 31671 | 316 | 0.0148 | HOMO->L + 4 (77%) |
| 32907 | 304 | 0.0029 | HOMO->L + 5 (61%) |
| 32973 | 303 | 0.011 | H-5->LUMO (10%), H-3->LUMO (30%), HOMO->L + 5 (13%) |
| 33348 | 300 | 0.007 | H-2->L + 1 (14%), H-1->L + 2 (63%) |

SUPPLEMENTARY TABLE 4

Major electronic transitions for N-methylaza[8]CPP Triflate 4 determined by TD-DFT method using B3LYP/6-31g*

| Energy (cm$^{-1}$) | Wavelength (nm) | Osc. Strength | Major contributions |
|---|---|---|---|
| 17642 | 567 | 0.0211 | HOMO->LUMO (97%) |
| 22549 | 443 | 0.2872 | H-1->LUMO (96%) |
| 23135 | 432 | 0.0754 | HOMO->L + 1 (91%) |
| 24872 | 402 | 0.2284 | H-2->LUMO (86%) |
| 26530 | 377 | 0.9003 | HOMO->L + 2 (81%) |
| 26958 | 371 | 0.6285 | HOMO->L + 3 (92%) |
| 27713 | 361 | 0.3411 | H-1->L + 1 (96%) |
| 30261 | 330 | 0.1507 | H-2->L + 1 (90%) |
| 30575 | 327 | 0.0542 | H-3->LUMO (81%) |
| 30753 | 325 | 0.0062 | H-4->LUMO (76%) |
| 30829 | 324 | 0.3272 | H-1->L + 2 (80%) |
| 31115 | 321 | 0.0277 | H-1->L + 3 (80%) |

SUPPLEMENTARY TABLE 5

| Energy (cm$^{-1}$) | Wavelength (nm) | Osc. Strength | Major contributions |
|---|---|---|---|

Major electronic transitions for N,N-dimethylaza[8]CPP Ditriflate 5 determined by TD-DFT method using B3LYP/6-31g*

| Energy (cm$^{-1}$) | Wavelength (nm) | Osc. Strength | Major contributions |
|---|---|---|---|
| 17128.11 | 583.8356 | 0.021 | HOMO->LUMO (97%) |
| 20140.61 | 496.5093 | 0.3892 | HOMO->L + 1 (100%) |
| 23722.54 | 421.54 | 0.5499 | H-1->LUMO (96%) |
| 24537.17 | 407.545 | 0.027 | HOMO->L + 2 (86%) |
| 24910.61 | 401.4354 | 0.026 | H-2->LUMO (24%), H-1->L + 1 (49%), HOMO->L + 3 (11%) |
| 25917.19 | 385.8443 | 0.1648 | H-2->LUMO (57%), H-1->L + 1 (39%) |
| 26478.56 | 377.6641 | 0.7374 | HOMO->L + 3 (84%) |
| 27597.26 | 362.3549 | 0.5307 | HOMO->L + 4 (91%) |
| 27845.68 | 359.1222 | 0.2789 | H-2->L + 1 (94%) |
| 29147.47 | 343.083 | 0.0067 | H-3->LUMO (89%) |
| 29804.01 | 335.5254 | 0.0012 | H-4->LUMO (79%) |
| 30058.07 | 332.6893 | 0.0075 | H-1->L + 2 (95%) |

Major electronic transitions for N,N-Dimethyl-1,26-diaza[8]CPP determined by TD-DFT method using B3LYP/6-31g*

| Energy (cm$^{-1}$) | Wavelength (nm) | Osc. Strength | Major contributions |
|---|---|---|---|
| 20050.28 | 498.7463 | 0.0006 | HOMO->LUMO (96%) |
| 22248.15 | 449.4756 | 0.3873 | HOMO->L + 1 (98%) |
| 23544.29 | 424.7314 | 0.4828 | H-1->LUMO (97%) |
| 24300.04 | 411.522 | 0.001 | H-1->L + 1 (95%) |
| 26658.42 | 375.116 | 0.0032 | HOMO->L + 2 (92%) |
| 27455.3 | 364.2284 | 0.3974 | H-2->LUMO (89%) |

SUPPLEMENTARY TABLE 5-continued

| Energy (cm$^{-1}$) | Wavelength (nm) | Osc. Strength | Major contributions |
|---|---|---|---|
| 27720.66 | 360.7418 | 0.7907 | HOMO->L + 3 (91%) |
| 28378.81 | 352.3755 | 0.0047 | H-2->L + 1 (87%) |
| 29091.81 | 343.7393 | 0.3808 | H-1->L + 2 (95%) |
| 29895.15 | 334.5025 | 0.0001 | H-1->L + 3 (87%) |
| 30956.58 | 323.0331 | 0.0001 | H-3->LUMO (86%) |
| 31111.44 | 321.4252 | 0.0129 | H-4->LUMO (85%) |

SUPPLEMENTARY TABLE 6

Major electronic transitions for N,N-Dimethyl-1,21-diaza[8]CPP determined by TD-DFT method using B3LYP/6-31g*

| Energy (cm$^{-1}$) | Wavelength (nm) | Osc. Strength | Major contribs |
|---|---|---|---|
| 18031.46 | 554.5864 | 0.0182 | HOMO->LUMO (96%) |
| 20902 | 478.4231 | 0.2643 | HOMO->L + 1 (98%) |
| 23527.36 | 425.0371 | 0.1906 | H-1->LUMO (74%), HOMO->L + 2 (19%) |
| 24769.46 | 403.723 | 0.587 | H-1->LUMO (21%), HOMO->L + 2 (72%) |
| 25784.92 | 387.8236 | 0.5172 | H-2->LUMO (79%) |
| 25867.19 | 386.5902 | 0.146 | H-1->L + 1 (30%), HOMO->L + 3 (64%) |
| 26030.92 | 384.1586 | 0.389 | H-2->LUMO (16%), H-1->L + 1 (57%), HOMO->L + 3 (25%) |
| 27589.19 | 362.4608 | 0.0975 | H-2->L + 1 (86%) |
| 29068.42 | 344.0159 | 0.5039 | HOMO->L + 4 (90%) |
| 29570.91 | 338.1702 | 0.0016 | H-3->LUMO (91%) |
| 29945.96 | 333.9349 | 0.1504 | H-1->L + 2 (94%) |
| 30617.02 | 326.6157 | 0.0021 | H-4->LUMO (70%), H-3->L + 1 (14%) |

SUPPLEMENTARY TABLE 7

Major electronic transitions for N,N-Dimethyl-1,8-diaza[8]CPP determined by TD-DFT method using B3LYP/6-31g*

| Energy (cm$^{-1}$) | Wavelength (nm) | Osc. Strength | Major contribs |
|---|---|---|---|
| 10786.93 | 927.0475 | 0.0437 | HOMO->LUMO (99%) |
| 15746.47 | 635.0629 | 0.2011 | H-1->LUMO (99%) |
| 19117.09 | 523.0923 | 0.2372 | H-2->LUMO (91%) |
| 20606.8 | 485.2767 | 0.0869 | HOMO->L + 1 (98%) |
| 20860.87 | 479.3664 | 0.114 | HOMO->L + 2 (88%) |
| 23061.16 | 433.6295 | 0.4661 | HOMO->L + 3 (98%) |
| 23502.35 | 425.4893 | 0.002 | H-3->LUMO (95%) |
| 23957.25 | 417.4101 | 0.0031 | H-6->LUMO (11%), H-4->LUMO (87%) |
| 24416.18 | 409.5644 | 0.0037 | H-5->LUMO (91%) |
| 24540.39 | 407.4914 | 0.0351 | H-1->L + 1 (95%) |
| 24807.37 | 403.1061 | 0.0026 | H-6->LUMO (80%), H-4->LUMO (12%) |
| 25446.16 | 392.9866 | 0.189 | H-7->LUMO (45%), H-1->L + 2 (49%) |

In view of the many possible embodiments to which the principles of the present disclosure may be applied, it should be recognized that the illustrated embodiments are only preferred examples of the present disclosure and should not be taken as limiting the scope of the claimed invention.

We claim:
1. A compound having a structure satisfying a formula

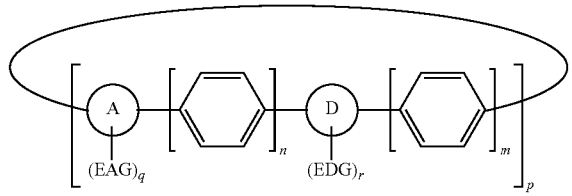

wherein each D ring independently is selected from phenyl, pyridinyl, benzo[1,2-b:4,5-b']dithiophenyl; benzo[1,2-b:4,5-b']difuranyl; or 1,5-dihydropyrrolo[2,3-f]indolyl; and each D ring is connected to other rings of the compound in a para-substitution pattern;
each A ring independently is phenyl, pyridinyl, pyridinyl comprising an aliphatic-substituted nitrogen atom, benzo[c][1,2,5]thiadiazolyl, benzo[c][1,2,5]oxadiazolyl, or 2H-benzo[d][1,2,3]triazolyl; and each A ring is connected to other rings of the compound in a para-substitution pattern;
each "EDG" independently is selected from alkoxy, thioether, amide, amine, hydroxyl, thiol, acyloxy, aliphatic, or aryl;
each "EAG" independently is selected from sulfonate; pyridinyl; alkyl halide; cyano; quaternary amine; nitro; aldehyde; ketone; carboxylic acid; —C(O)R$^b$, wherein R$^b$ is selected from alkyl, alkenyl, alkynyl, aryl, heteroalkyl, heteroalkenyl, heteroalkynyl, or heteroaryl; or acyl halide;
each q independently is an integer selected from 0, 1, or 2;
each r independently is an integer selected from 0, 1, or 2;
n is an integer selected from 0 to 18;
m is an integer selected from 0 to 18;
p is an integer selected from 1 to 10; provided that the compound comprises a total number of rings ranging from 6 to 20; and
wherein the compound is not, or is other than,

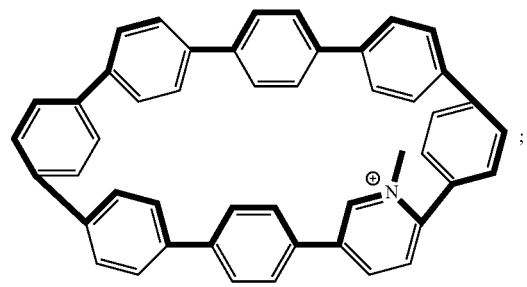

wherein the compound is not, or is other than, a non-functionalized nanohoop consisting of phenyl rings; and
wherein the compound is not, or is other than, a compound consisting of phenyl and pyridinyl rings, wherein any pyridinyl ring lacks N-substitution with an aliphatic group.
2. The compound of claim 1, wherein the D ring is phenyl.
3. The compound of claim 1, wherein each EAG independently is selected from cyano, alkyl halide, pyridinyl, or combinations thereof.

4. The compound of claim 1, wherein the compound has a structure satisfying any one or more of the following formulas:
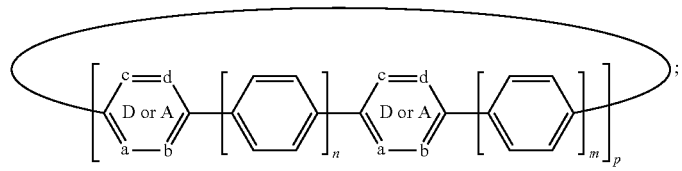
Formula IC
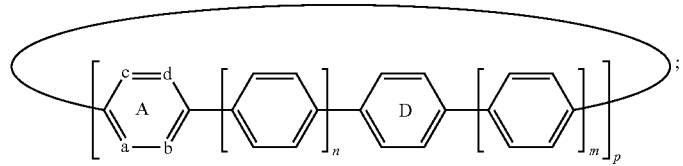
Formula ID
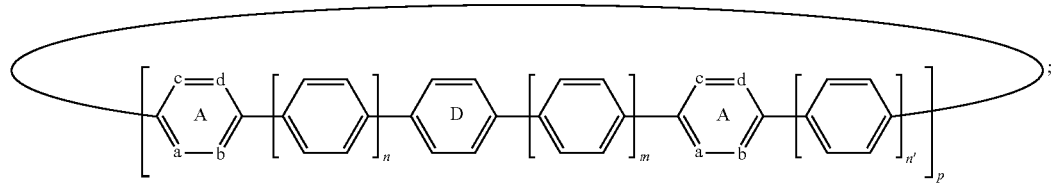
Formula IE
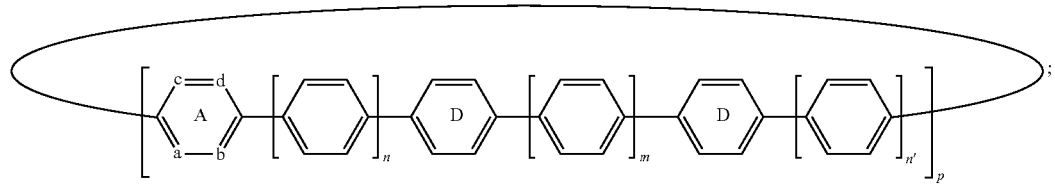
Formula IF
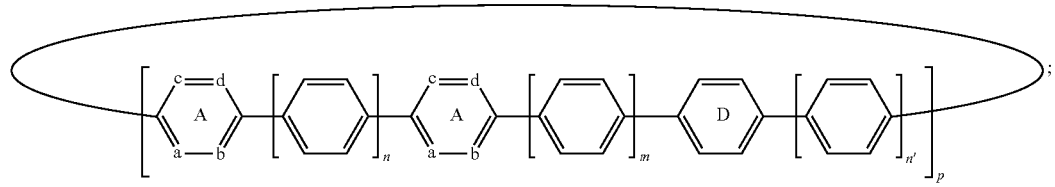
Formula IIB
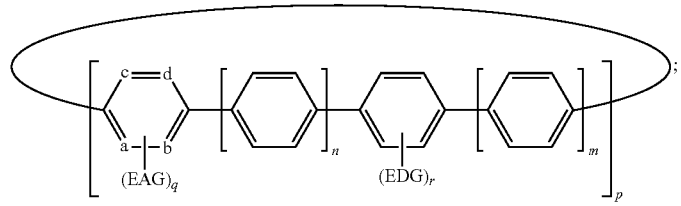
Formula IIC
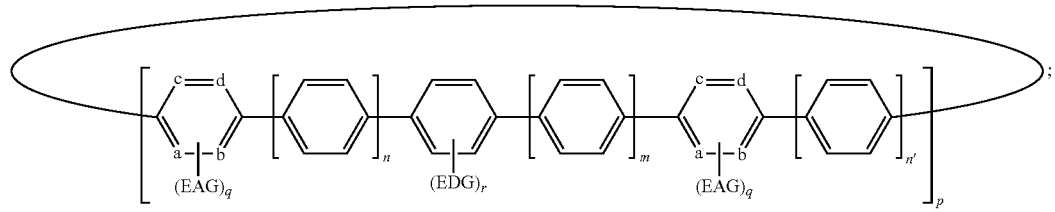

-continued

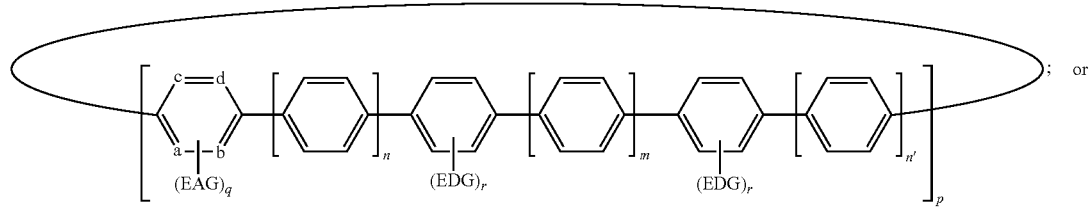

Formula IID

; or

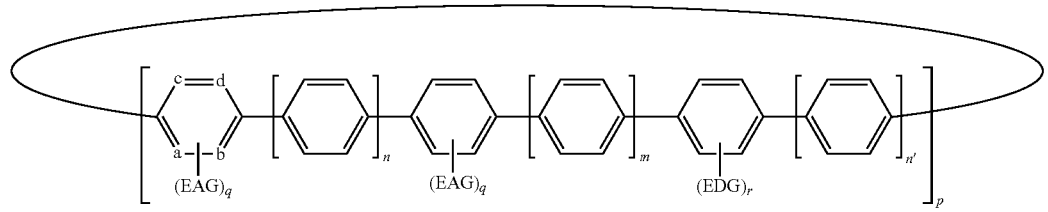

Formula IIE wherein
one of a, b, c, or d is carbon, nitrogen, or nitrogen comprising an aliphatic group and each other a, b, c, or d is carbon;

each n' independently is an integer selected from 1 to 18.

5. The compound of claim 1, wherein the compound has a structure satisfying a formula

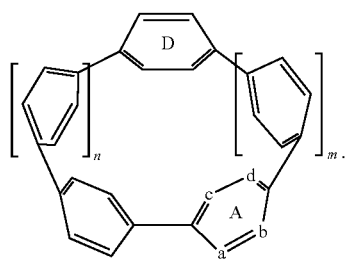

wherein (i) one of a, b, c, or d is carbon and further wherein the A ring comprises one or more electron-accepting groups selected from sulfonate; pyridinyl; alkyl halide; cyano; quaternary amine; nitro; aldehyde; ketone; carboxylic acid; —C(O)R$^b$, wherein R$^b$ is selected from akyl, alkenyl, alkynyl, aryl, heteroalkyl, heteroalkenyl, heteroalkynyl, or heteroaryl; or acyl halide; and each other a, b, c, or d is carbon; or (ii) one of a, b, c, or d is nitrogen comprising an aliphatic group and each other a, b, c, or d is carbon.

6. The compound of claim 1, wherein the compound has a structure satisfying a formula selected from

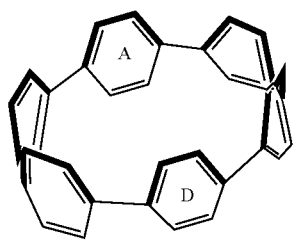

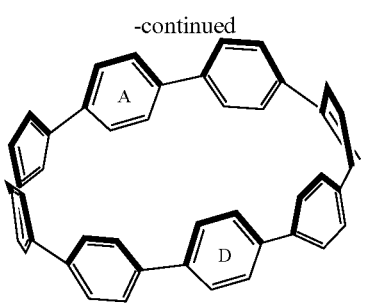

wherein the A phenyl ring comprises one or more electron-accepting groups selected from sulfonate; pyridinyl; alkyl halide; cyano; quaternary amine; nitro; aldehyde; ketone; carboxylic acid; —C(O)R$^b$, wherein R$^b$ is selected from alkyl, alkenyl, alkynyl, aryl, heteroalkyl, heteroalkenyl, heteroalkynyl, or heteroaryl; or acyl halide; and the D phenyl ring comprises one or two EDGs.

7. The compound of claim 1, wherein the compound is selected from

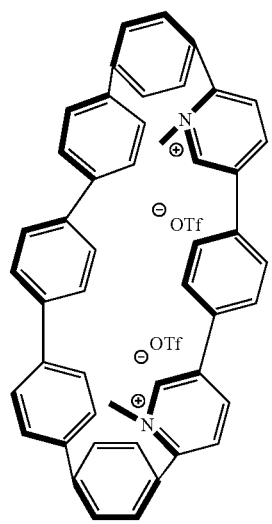

;

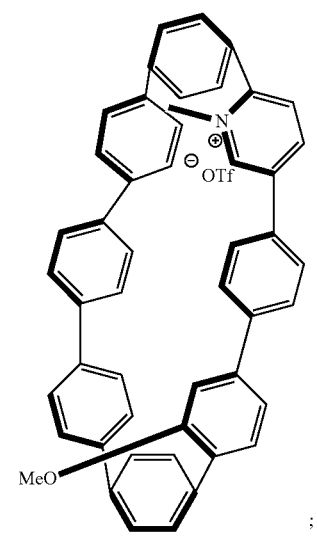
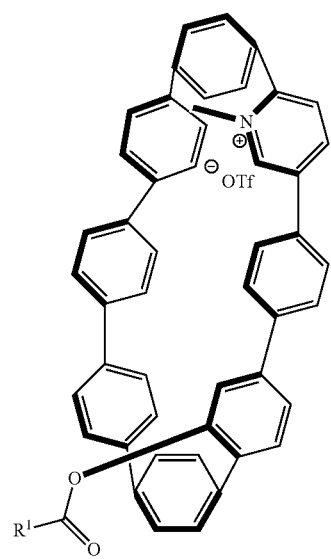
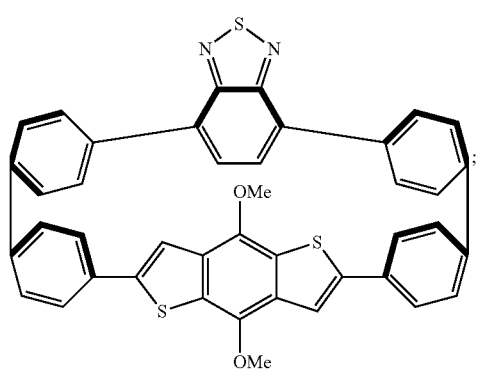
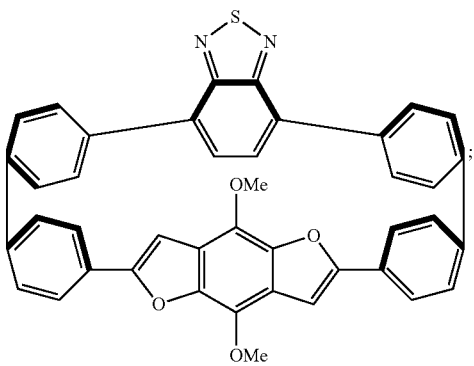
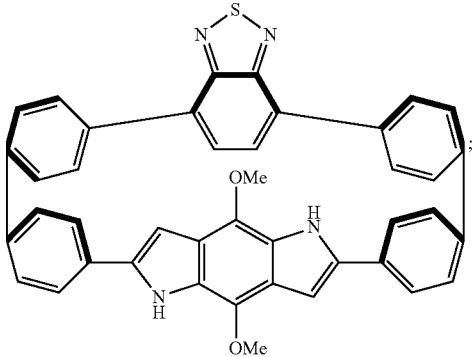
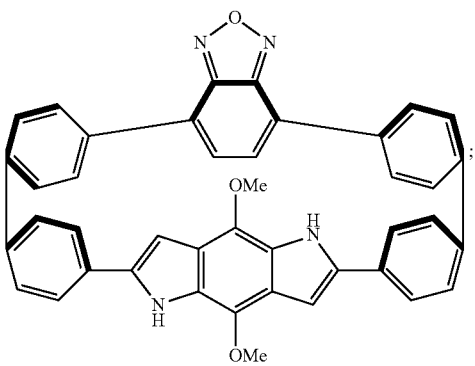
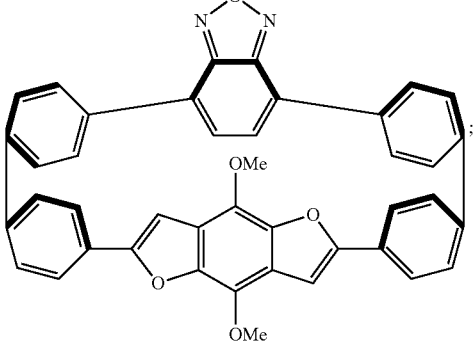

57
-continued
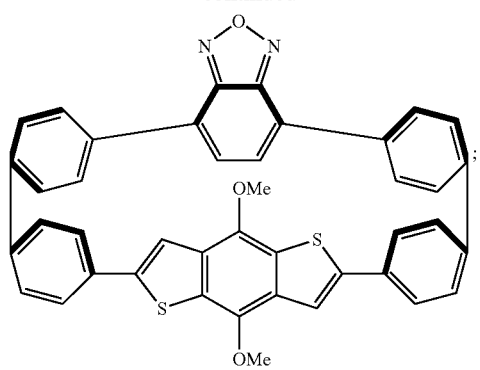
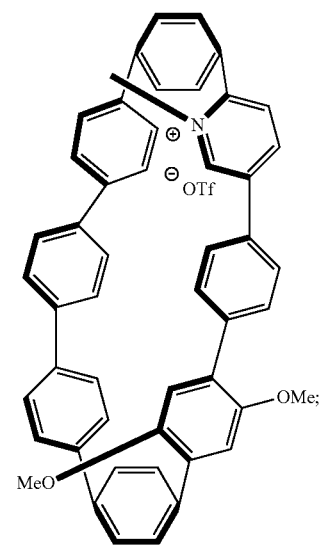
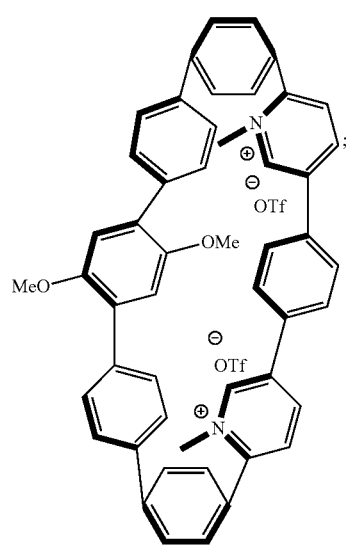
58
-continued
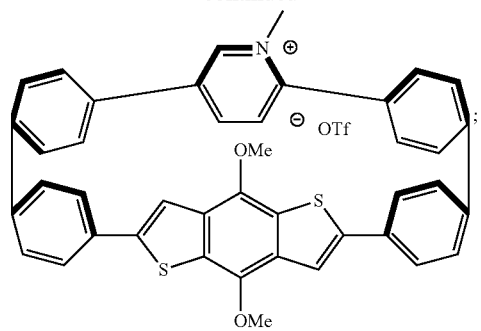
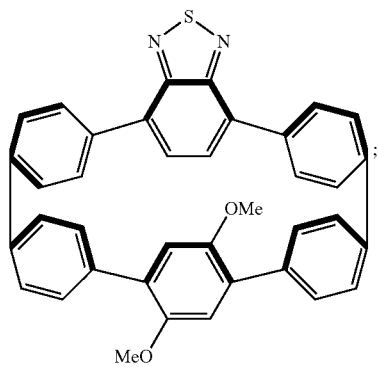
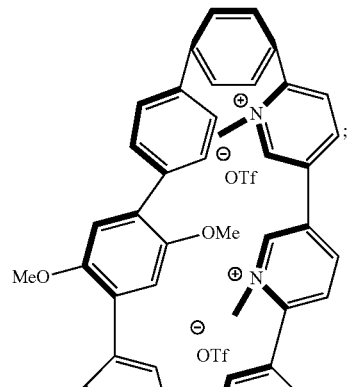
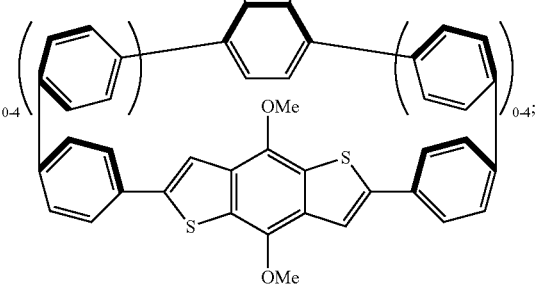

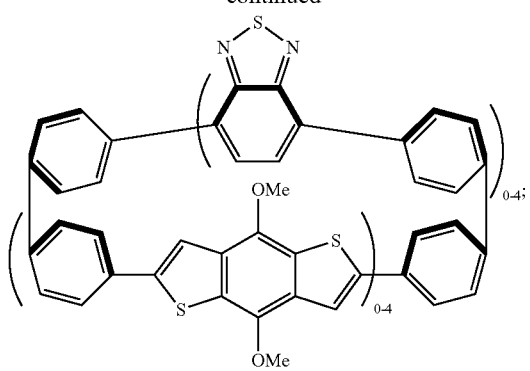
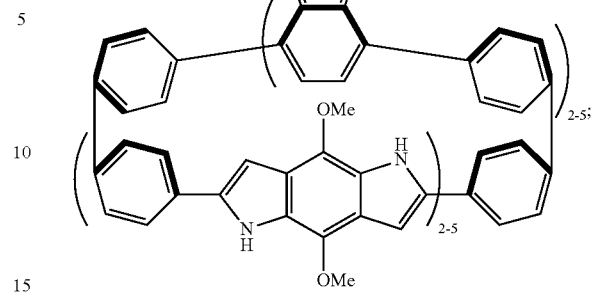
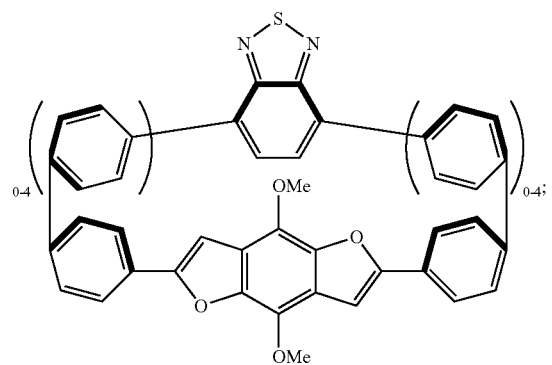
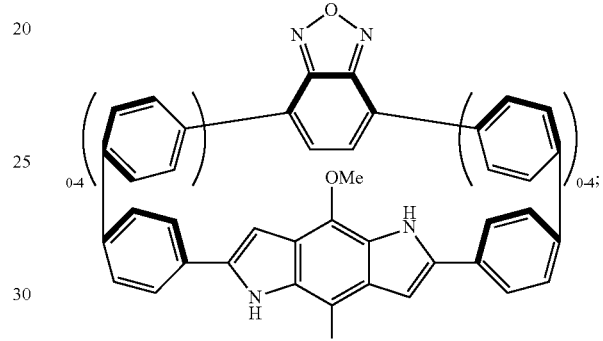
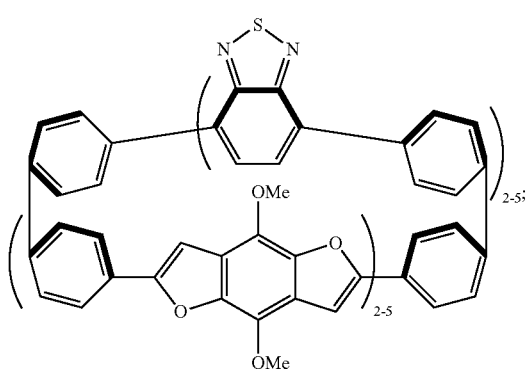
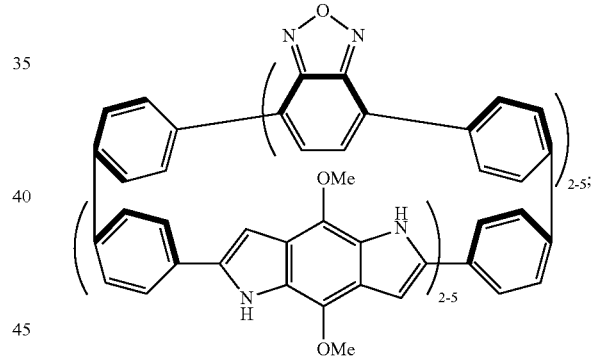
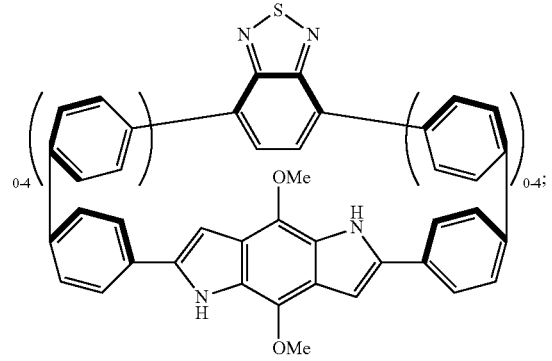
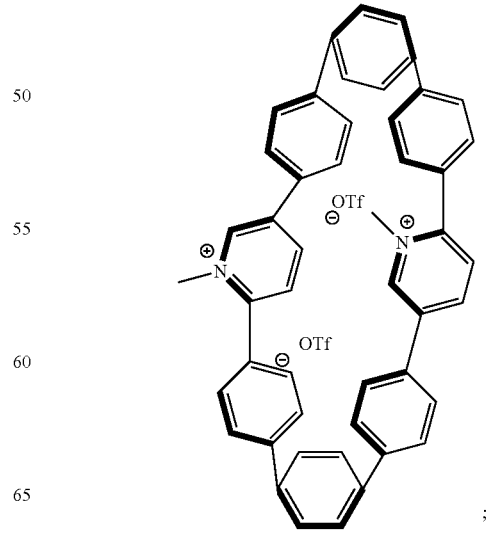

-continued

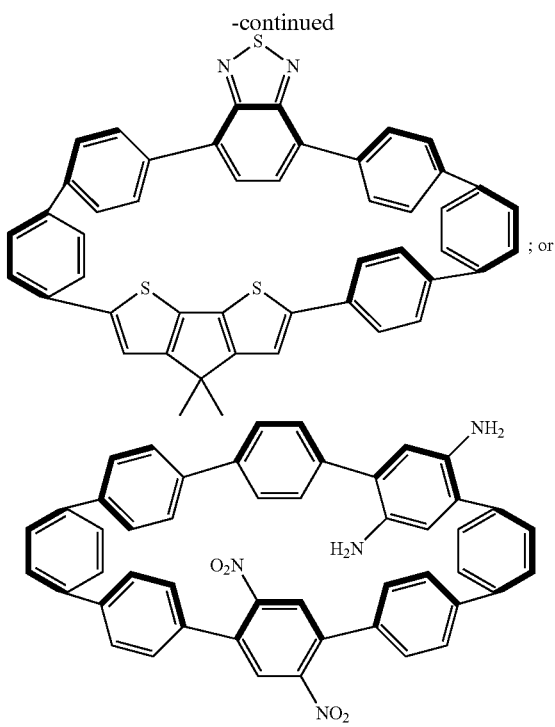

wherein R¹ is selected from alkyl, alkenyl, alkynyl, aryl, heteroalkyl, heteroalkenyl, heteroalkynyl, heteroaryl, or hydrogen.

8. The compound of claim 1, wherein the compound is a functionalized nanohoop compound that exhibits a LUMO energy level ranging from greater than −2.0 eV to −5 eV.

9. The compound of claim 1, wherein the compound is a functionalized nanohoop compound that exhibits a LUMO energy level ranging from −2.5 eV to −4.0 eV.

10. The compound of claim 1, wherein the compound is a functionalized nanohoop compound that exhibits a HOMO energy level ranging from −5.0 eV to −7 eV.

11. The compound of claim 1, wherein the compound is a functionalized nanohoop compound that exhibits a HOMO energy level ranging from −5.2 eV to −6.5 eV.

12. A device, comprising a compound according to claim 1, wherein the device is an organic photovoltaic device, an organic field effect transistor, a molecular wire, or an organic light emitting diode.

13. A method of making a compound of claim 1, comprising exposing a compound of a formula

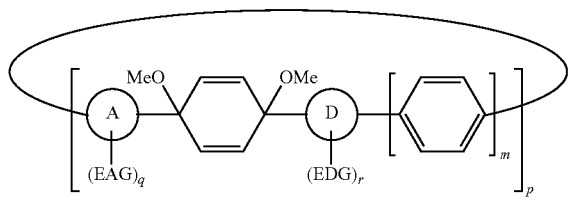

to a reducing agent to thereby produce the compound of claim 1.

14. The method of claim 13, wherein the reducing agent is an organic salt.

15. The method of claim 13, wherein the reducing agent is a metal naphthalenide.

16. The method of claim 13, wherein the reducing agent is sodium naphthalenide.

17. The compound of claim 1, wherein each D ring independently is phenyl, pyridinyl, benzo[1,2-b:4,5-b']dithiophenyl; benzo[1,2-b:4,5-b']difuranyl; or 1,5-dihydropyrrolo[2,3-f]indolyl; and each A ring independently is a phenyl ring comprising one or two EAGs, or pyridinyl comprising an aliphatic-substituted nitrogen atom.

18. The compound of claim 1, wherein:
each D ring independently is benzo[1,2-b:4,5-b']dithiophenyl; benzo[1,2-b:4,5-b']difuranyl; 1,5-dihydropyrrolo[2,3-f]indolyl; or 4,4-dimethyl-4H-cyclopenta[2,1-b:3,4-b']dithiophene; and
each A ring independently is benzo[c][1,2,5]thiadiazolyl, benzo[c][1,2,5]oxadiazolyl, or 2H-benzo[d][1,2,3]triazolyl.

19. The compound of claim 1, wherein:
each D ring independently is benzo[1,2-b:4,5-b']dithiophenyl; benzo[1,2-b:4,5-b']difuranyl; or 1,5-dihydropyrrolo[2,3-f]indolyl; and
each A ring independently is phenyl or pyridinyl comprising an aliphatic-substituted nitrogen atom; or wherein
each D ring independently is selected from phenyl, pyridinyl, benzo[1,2-b:4,5-b']dithiophenyl; benzo[1,2-b:4,5-b']difuranyl; or 1,5-dihydropyrrolo[2,3-f]indolyl; and
each A ring independently is benzo[c][1,2,5]thiadiazolyl, benzo[c][1,2,5]oxadiazolyl, or 2H-benzo[d][1,2,3]triazolyl.

20. A compound having a structure satisfying a formula

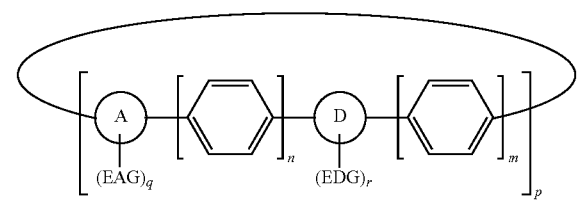

wherein each D ring independently is a phenyl ring and each D ring is connected to other rings of the compound in a para-substitution pattern;
each A ring independently is a pyridinyl ring comprising a nitrogen atom that is substituted with an aliphatic group and each A ring is connected to other rings of the compound in a para-substitution pattern;
each "EDG" independently is selected from alkoxy, thioether, amide, amine, hydroxyl, thiol, acyloxy, aliphatic, or aryl;
each "EAG" independently is selected from sulfonate; pyridinyl; alkyl halide; cyano; quaternary amine; nitro; aldehyde; ketone; carboxylic acid; —C(O)R$^b$, wherein R$^b$ is selected from alkyl, alkenyl, alkynyl, aryl, heteroalkyl, heteroalkenyl, heteroalkynyl, or heteroaryl; or acyl halide;
each q independently is an integer selected from 0, 1, or 2;
each r independently is an integer selected from 0, 1, or 2;
n is an integer selected from 0 to 18;
m is an integer selected from 0 to 18;

p is an integer selected from 1 to 10; provided that the compound comprises a total number of rings ranging from 6 to 20; and wherein the compound is not, or is other than,

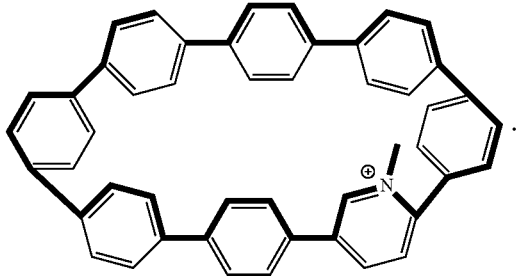

.

21. A compound having a structure satisfying a formula

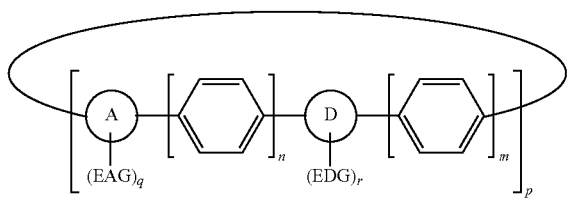

wherein each D ring independently is 4,4-dimethyl-4H-cyclopenta[2,1-b:3,4-b']dithiophene; and each D ring is connected to other rings of the compound in a para-substitution pattern;

each A ring independently is phenyl, pyridinyl, pyridinyl comprising an aliphatic-substituted nitrogen atom, benzo[c][1,2,5]thiadiazolyl, benzo[c][1,2,5]oxadiazolyl, or 2H-benzo[d][1,2,3]triazolyl; and each A ring is connected to other rings of the compound in a para-substitution pattern;

each "EDG" independently is selected from alkoxy, thioether, amide, amine, hydroxyl, thiol, acyloxy, aliphatic, or aryl;

each "EAG" independently is selected from sulfonate; pyridinyl; alkyl halide; cyano; quaternary amine; nitro; aldehyde; ketone; carboxylic acid; —C(O)$R^b$, wherein $R^b$ is selected from alkyl, alkenyl, alkynyl, aryl, heteroalkyl, heteroalkenyl, heteroalkynyl, or heteroaryl; or acyl halide;

each q independently is an integer selected from 0, 1, or 2;

each r independently is an integer selected from 0, 1, or 2;

n is an integer selected from 0 to 18;

m is an integer selected from 0 to 18; and p is an integer selected from 1 to 10; provided that the compound comprises a total number of rings ranging from 6 to 20.

* * * * *